United States Patent
Liang et al.

(12)

(10) Patent No.: US 12,421,549 B1
(45) Date of Patent: Sep. 23, 2025

(54) METHOD AND KIT FOR GENOTYPING OF MULTI-SYSTEM RED BLOOD CELL (RBC) BLOOD GROUP BASED ON NEXT-GENERATION SEQUENCING (NGS)

(71) Applicant: Shenzhen Blood Center, Guangdong (CN)

(72) Inventors: Shuang Liang, Guangdong (CN); Jinfeng Zeng, Guangdong (CN); Yanlian Liang, Guangdong (CN); Fan Wu, Guangdong (CN); Tong Liu, Guangdong (CN); Liyan Sun, Guangdong (CN)

(73) Assignee: Shenzhen Blood Center, Guangdong (CN)

( * ) Notice: Subject to any disclaimer, the term of this patent is extended or adjusted under 35 U.S.C. 154(b) by 0 days.

(21) Appl. No.: 19/014,935

(22) Filed: Jan. 9, 2025

(30) Foreign Application Priority Data

Apr. 10, 2024 (CN) .......................... 202410433057.4

(51) Int. Cl.
- *C12P 19/34* (2006.01)
- *C12Q 1/6874* (2018.01)
- *C12Q 1/6881* (2018.01)
- *C12Q 1/6806* (2018.01)

(52) U.S. Cl.
CPC ......... *C12Q 1/6881* (2013.01); *C12Q 1/6874* (2013.01); *C12Q 1/6806* (2013.01); *C12Q 2600/16* (2013.01)

(58) Field of Classification Search
CPC .................................................. C12Q 1/6881
See application file for complete search history.

(56) References Cited

U.S. PATENT DOCUMENTS

| | | | | |
|---|---|---|---|---|
| 2008/0261205 A1* | 10/2008 | Denomme | ............. | C07H 21/04 435/6.16 |
| 2009/0186340 A1* | 7/2009 | Olsson | ................. | C12Q 1/6883 435/6.12 |
| 2018/0305756 A1* | 10/2018 | Ochoa | .................. | C12Q 1/6881 |
| 2023/0235396 A1* | 7/2023 | Ye | ........................... | C12Q 1/686 435/6.11 |
| 2023/0272429 A1* | 8/2023 | Dowdle | ............... | A61K 35/545 424/93.21 |

\* cited by examiner

*Primary Examiner* — Kenneth R Horlick
(74) *Attorney, Agent, or Firm* — Renner, Kenner, Greive, Bobak, Taylor & Weber

(57) ABSTRACT

A method and a kit for genotyping of multi-system red blood cell (RBC) blood group based on next-generation sequencing (NGS) are provided. Multiplex PCR capture primer sets and amplification reaction conditions thereof can be designed using Illumina as a platform to simultaneously detect full-length coding regions and spliced flanking regions of 25 blood group genes in 17 RBC blood group systems among three reactions, thereby enabling rapid genotyping of the 17 RBC blood group systems and multiple key rare blood groups therein. The method and the kit are based on high-throughput sequencing and have a high detection efficiency and a low average cost; the method and the kit also break through a limitation of existing blood group gene detection technology that cannot distinguish haplotypes; moreover, variations including known mutation sites and unknown mutation sites can be detected to obtain comprehensive and accurate detection results.

8 Claims, 4 Drawing Sheets

Specification includes a Sequence Listing.

1-H07951D; 2-H07949D; 3-H07934D; 4-H07936D; 5- H07939D;
6-H07939D; 7-H07942D; 8-H07943D; 9-H07948D; 10-H07938D;
11-H07929D; 12-H07940D; 13-H07941D; 14-H07947D; 15-NC 1,7-H07939D; 2,8-H07938D; 3,9-H07929D; 4,10-H07940D;
5,11-H07941D; 6,12-H07947D; 13,14-NC

METHOD AND KIT FOR GENOTYPING OF MULTI-SYSTEM RED BLOOD CELL (RBC) BLOOD GROUP BASED ON NEXT-GENERATION SEQUENCING (NGS)

CROSS REFERENCE TO RELATED APPLICATION

This patent application claims the benefit and priority of Chinese Patent Application No. 2024104330574, filed with the China National Intellectual Property Administration on Apr. 10, 2024, the disclosure of which is incorporated by reference herein in its entirety as part of the present application.

REFERENCE TO SEQUENCE LISTING

A computer readable XML file entitled "Sequence Listing", that was created on Dec. 26, 2024, with a file size of 364, 120 bytes, contains the sequence listing for this application, has been filed with this application, and is hereby incorporated by reference in its entirety.

TECHNICAL FIELD

The present disclosure belongs to the technical field of blood group genotyping, and specifically relates to a method and a kit for genotyping of 25 coding genes in 17 red blood cell (RBC) blood group systems based on next-generation sequencing (NGS).

BACKGROUND

A human blood group system consists of red blood cell (RBC) surface antigens (proteins, glycoproteins, or glycolipids). The blood group system is inherited and controlled by a single gene or a gene cluster of two or three closely-linked homologous genes. As of July 2023, there are a total of 378 RBC blood group antigens recognized by the International Society of Blood Transfusion (ISBT), of which 360 belong to 45 blood group systems. Human RBCs selectively express antigens from different blood group systems, which constitute each person's unique blood group combination. In addition to ABO, there are 17 most clinically important RBC blood group systems in China, including H, RH (including RHD and RHCE), MNS, Kidd, Diego, Duffy, Lewis, Kell, P1Pk, GLOB, Lutheran, Yt, SC, DO, CO, LW, and JR.

To ensure the safety of clinical blood transfusion, a primary factor is that blood groups of the donor and the patient are consistent. There are two problems:

First, unconventional blood group systems cause adverse reactions to blood transfusions. Nowadays, ABO and RhD blood groups (conventional blood groups) are those that medical institutions conduct routine test and homotype transfusion; for blood group systems (non-conventional blood groups) other than the above two, routine test is omitted due to technical and cost limitations. Therefore, for patients with chronic blood transfusions, multiple transfusions of unconventional blood with an incompatible blood group may stimulate the immune system to produce blood group alloantibodies, triggering transfusion reactions that may even be life-threatening in severe cases. According to statistics from Serious Hazards of Transfusion (SHOT) in the UK, all hemolytic transfusion reactions in the past five years were caused by incompatible transfusions with unconventional blood group systems. A key to solving this problem lies in matching blood transfusions with unconventional blood group systems in patients with chronic blood transfusions.

Second, the supply of blood for rare blood groups should be guaranteed. A rare blood group does not refer to a specific blood group, but refers to a blood group whose frequency is less than one in a thousand among all people. For example, the above-mentioned 17 most clinically important blood group systems in China mainly include 31 key rare blood groups. Blood of rare blood groups is an extremely scarce resource. It is currently the only way to solve the problem of blood supply for clinical rare blood types by conducting large-scale screening among blood donors to find those with rare blood groups and freezing blood of the rare blood groups. However, the difficulty in screening rare blood groups is that there is no technology suitable for simultaneous detection of multiple blood group systems yet at home and abroad.

RBC blood group identification belongs to the field of in vitro diagnostics, and identification methods include serological test and genetic diagnosis. The serological test is the most traditional blood group identification method as well as a commonly used blood group identification method in clinical medical institutions. The RBC blood group is identified by specific reaction in vitro between serum (antibody reagent) containing known specific antibodies and the antigens on a RBC surface to be tested, showing the advantages of simple operation, rapidity, and easy interpretation. However, the serological test is limited by the availability of blood group antibody reagents, and most unconventional blood group systems do not have commercially available antibody reagents globally; a few commercially available reagents completely depend on imports, and are expensive and in short supply. This is a "bottleneck" faced by the current in vitro diagnostic industry of blood groups.

When the serological test was limited, RBC blood group genetic diagnosis based on PCR and sequencing came into being. There are 1,568 alleles listed in a blood group gene mutation database of the National Center for Biotechnology Information (NCBI). Blood type can be predicted by detecting the coding genes of blood group antigens and analyzing genetic polymorphism characteristics. The most significant advantage of genotyping to detect blood groups is to supplement and overcome the deficiencies of serology. For example, diseases, drugs, and treatments (especially recent blood transfusions) interfere with the serological test, making blood group results ambiguous; there are individuals with genetic mutations that result in reduced antigen expression or with unexpected antibodies. In addition, for rare blood groups for which serological test antibody reagents are not available, genotyping is the only way to predict the blood group.

The blood group genetic testing technologies currently widely used in clinical and blood collection and supply institutions in China are polymerase chain reaction-sequence specific primer (PCR-SSP) and first-generation sequencing (Sanger). A prerequisite for the PCR-SSP to identify blood group alleles is to clarify DNA sequences and single nucleotide polymorphisms (SNPs) in order to prepare corresponding primers or probes. Therefore, this technique is not suitable for detecting mutations of unknown sequences or blood group gene with high polymorphism. The Sanger is a gold standard for genetic testing, and can accurately obtain the nucleotide sequence of a target gene or a certain fragment and identify unknown mutations. However, this technique cannot directly distinguish between two haplotypes and may sometimes produce ambiguous typing results. Moreover, as low-to-medium-throughput genetic testing techniques, the PCR-SSP and Sanger are in a high cost and less efficient for screening rare blood groups. In this case, next-generation sequencing (NGS), also known as high-throughput sequencing, is more appropriate. The NGS determines a DNA sequence while synthesizing same by capturing newly synthesized end tags, and allows the detection of one single haplotype DNA sequence to avoid ambiguous typing results. In addition, the NGS has an extremely high detection throughput and can greatly increase the detection throughput, and is highly suitable for large-scale screening of rare blood groups.

SUMMARY

A purpose of the present disclosure is to provide a method and a kit for genotyping of 25 coding genes in 17 red blood cell (RBC) blood group systems based on next-generation sequencing (NGS). In the present disclosure, the method based on NGS and multiplex PCR effectively improves both accuracy and detection efficiency for the genotyping of RBC blood group, and can save the manpower in genotyping of the RBC blood group to a certain extent.

The present disclosure provides a primer set for simultaneously detecting genotyping of 17 RBC blood group systems, including primers with nucleotide sequences shown in SEQ ID NO: 1 to SEQ ID NO: 336.

Preferably, a first primer set includes the primers with the nucleotide sequences shown in SEQ ID NO: 1 to SEQ ID NO: 108;
  a second primer set includes the primers with the nucleotide sequences shown in SEQ ID NO: 109 to SEQ ID NO: 222; and
  a third primer set includes the primers with the nucleotide sequences shown in SEQ ID NO: 223 to SEQ ID NO: 336.

The present disclosure further provides a kit for simultaneously detecting genotyping of 17 RBC blood group systems, including the primer set and a PCR reaction solution.

Preferably, the first primer set, the second primer set, and the third primer set in the primer set are packaged independently.

The present disclosure further provides a method for simultaneously detecting genotyping of 17 RBC blood group systems, including the following steps: (1) subjecting three capture and amplification systems to first amplification separately to obtain three first amplification products, where the three capture and amplification systems are prepared by using a nucleic acid extracted from a sample as a template and a first primer set with nucleotide sequences shown in SEQ ID NO: 1 to SEQ ID NO: 108, a second primer set with nucleotide sequences shown in SEQ ID NO: 109 to SEQ ID NO: 222, and a third primer set with nucleotide sequences shown in SEQ ID NO: 223 to SEQ ID NO: 336, respectively;
  (2) purifying the three first amplification products separately, and subjecting three resulting purified first amplification products to second amplification with a sequencing universal adapter carrying an index separately to obtain three second amplification products; and
  (3) purifying and mixing the three second amplification products to allow sequencing to obtain the genotyping of the RBC blood group systems.

Preferably, the sample in step (1) is selected from the group consisting of a whole blood sample, a plasma sample, and a paraffin tissue sample.

Preferably, the three capture and amplification systems in step (1) each have a volume of 25 µL, and include 1 µL of a mixture of the first primer set or the second primer set or the third primer set, 3 µL of an enzyme mixture Pxp-1st-mix, 1 µL of the template, and nuclease-free water as a balance.

Preferably, a PCR reaction program of the first amplification in step (1) includes: initial denaturation at 98° C. for 20 min; 9 cycles of denaturation at 98° C. for 15 s, annealing at 62° C. for 20 min, extension at 68° C. for 60 s, and extension at 72° C. for 60 s; extension at 72° C. for 5 min; and heat preservation at 10° C.

Preferably, a system of the second amplification in step (2) has a volume of 12.5 µL, and includes 6.5 µL of an enzyme mixture Pxp-2nd-mix, 4 µL for one of the three purified first amplification products, 1 µL of a universal adapter N5XX, and 1 µL of a universal adapter A7XX.

Preferably, a PCR reaction program of the second amplification in step (2) includes: initial denaturation at 98° C. for 2 min; 23 cycles of denaturation at 98° C. for 15 s, extension at 68° C. for 60 s, and extension at 72° C. for 60 s; extension at 72° C. for 10 min; and heat preservation at 4° C.

Beneficial effects: the present disclosure provides a PCR primer set and a kit for genotyping and capturing 25 coding genes of 17 RBC blood group systems based on a MiSeq NGS platform of the Illumina platform. The primer and kit can simultaneously detect multiple samples and multiple genes, including hereditary mutations such as point mutations and short indels. The kit effectively improves detection efficiency and accuracy, while reducing costs, simplifying operating steps, and providing flexible packaging specifications.

In the present disclosure, a detection method for detecting 31 key rare blood groups of 17 RBC blood group systems is constructed based on the primer set or kit. High-throughput sequencing is conducted to simultaneously detect 17 RBC blood group system-related genes to improve detection efficiency and reduce costs. The high-throughput gene sequencing can break through the limitations of traditional detection technology and improve detection sensitivity. Meanwhile, variations including known mutation sites and unknown mutation sites can be detected to obtain comprehensive and accurate detection results. By sequencing 17 RBC blood group system-related genes and their mutation sites, specific gene sequence information can be obtained, thereby providing accurate and efficient detection for rare blood group detection.

DETAILED DESCRIPTION OF THE EMBODIMENTS

Figure 1:
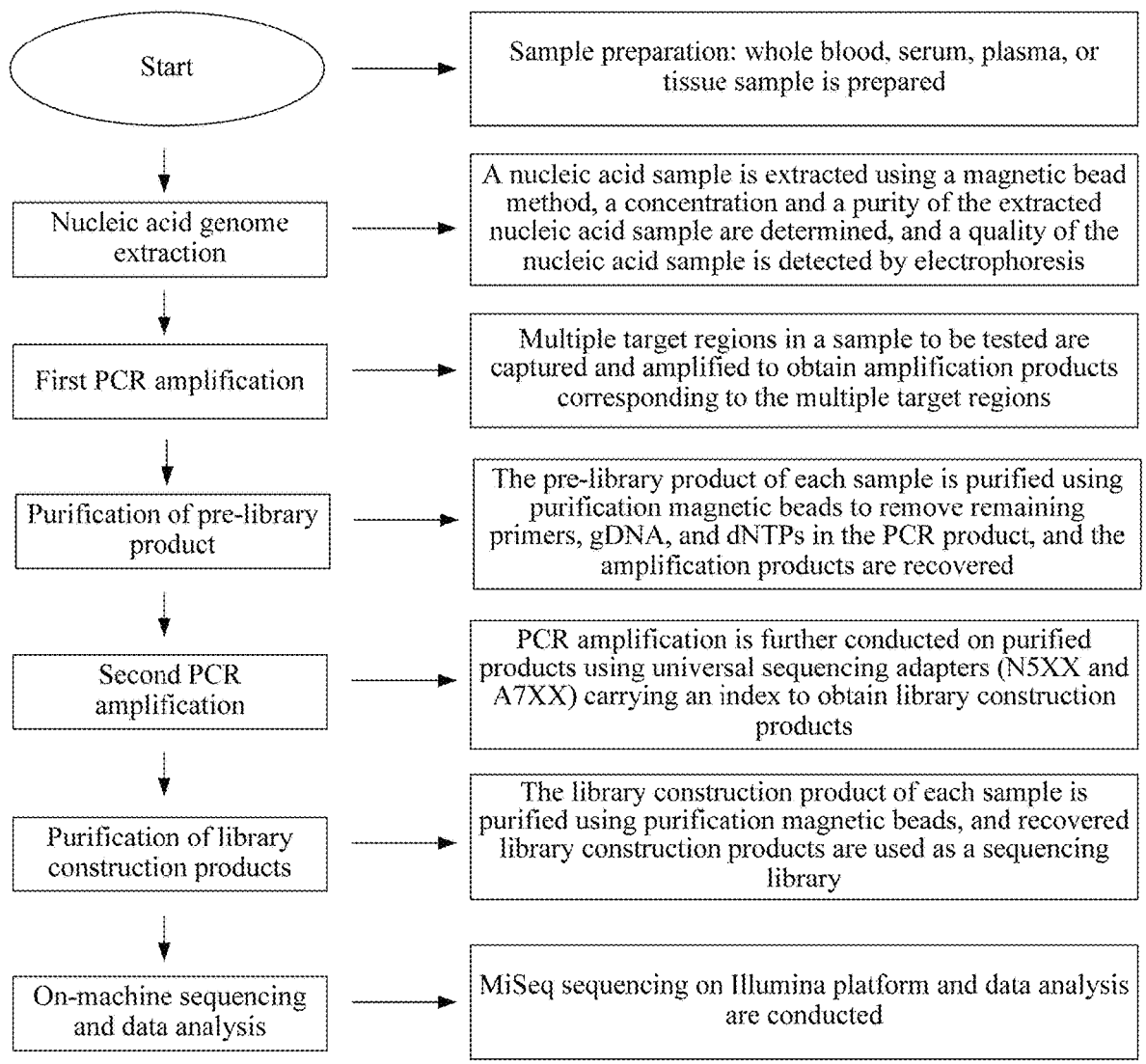
FIG. 1 shows a flow chart for RBC blood group identification using the primer set or kit of the present disclosure.

The present disclosure provides a primer set for simultaneously detecting genotyping of 17 RBC blood group systems, including primers with nucleotide sequences shown in SEQ ID NO: 1 to SEQ ID NO: 336.

In the present disclosure, the RBC blood group system and corresponding genetic information are shown in Table 1.

TABLE 1

Gene information of the 17 RBC blood group systems

| No. | ISBT No. | Blood group system | Coding gene | Chromosome | Number of sites | Number of types | Number of bases | Number of primer pairs |
|---|---|---|---|---|---|---|---|---|
| 1 | ISBT 018 | H | FUT1 | chr19 | 75 | 57 | 58 | 8 |
|   |   |   | FUT2 | chr19 | 31 | 37 | 32 | 6 |
|   |   |   | SLC35C1 | chr11 | 6 | 4 | 3 | 3 |
| 2 | ISBT 004 | RH | RhD | chr1 | 249 | 387 | 231 | 12 |
|   |   |   | RhCE | chr1 | 130 | 183 | 136 | 10 |
| 3 | ISBT 002 | MNS | GYPA | chr4 | 45 | 44 | 123 | 3 |
|   |   |   | GYPB | chr4 | 24 | 15 | 14 | 3 |
| 4 | ISBT 009 | Kidd | SLC14A1(JK) | chr18 | 29 | 32 | 49 | 7 |
| 5 | ISBT 010 | Diego | SLC4A1(DI) | chr17 | 39 | 40 | 19 | 5 |
| 6 | ISBT 008 | Duffy | ACKR1(FY) | chr1 | 21 | 24 | 229 | 6 |
| 7 | ISBT 007 | Lewis | FUT3 | chr19 | 42 | 60 | 38 | 6 |
|   |   |   | FUT6 | chr19 | 37 | 20 | 21 | 5 |
|   |   |   | FUT7 | chr9 | 2 | 2 | 1 | 1 |
| 8 | ISBT 006 | Kell | KEL | chr7 | 96 | 94 | 67 | 16 |
| 9 | ISBT 003 | P1Pk | A4GALT | chr22 | 39 | 41 | 198 | 7 |
| 10 | ISBT 028 | GLOB | B3GALNT1 | chr3 | 14 | 14 | 15 | 6 |
| 11 | ISBT 005 | Lutheran | BCAM(LU) | chr19 | 50 | 42 | 332 | 11 |
|   |   |   | KLF1 | chr19 | 58 | 56 | 148 | 9 |
|   |   |   | GATA1 | chrX | 1 | 1 | 1 | 1 |
| 12 | ISBT 011 | Yt | ACHE | chr7 | 4 | 4 | 4 | 2 |
| 13 | ISBT 013 | SC | ERMAP | chr1 | 7 | 6 | 8 | 3 |
| 14 | ISBT 014 | DO | ART4 | chr12 | 19 | 14 | 22 | 7 |
| 15 | ISBT 015 | CO | AQP1 | chr7 | 9 | 9 | 450 | 4 |
| 16 | ISBT 016 | LW | ICAM4 | chr19 | 2 | 2 | 11 | 1 |
| 17 | ISBT 032 | JR | ABCG2 | chr4 | 43 | 37 | 1946 | 26 |
| Total |   |   |   |   | 1072 | 1225 | 4156 | 168 |

The present disclosure is based on 1,072 blood group system typing sites of 25 genes shown in Table 1: H (ISBT 018), Rh (ISBT 004), MNS (ISBT 002), Kidd (JK, ISBT 009), Diego (DI, ISBT 010), Duffy (FY, ISBT 008), Lewis (ISBT 007), Kell (ISBT 006), P1Pk (ISBT 003), Globoside (GLOB, ISBT 028), Lutheran (LU, ISBT 005), YT (ISBT 011), Scianna (SC, ISBT 013), Dombrock (DO, ISBT 014), Colton (CO, ISBT 015), Landsteiner-Wiener (LW, ISBT 016), and Junior (JR, ISBT 032). The present disclosure develops a multiplex PCR-based RBC blood type NGS typing primer set, kit and method adapted to the Illumina sequencing platform. The primer set is designed based on the target region of the above gene. The target region preferably includes the full length of the coding region sequences of the 25 antigen-coding genes of the above-mentioned 17 blood group systems and the splicing flanking region within 100 bp to 150 bp. In the present disclosure, the 26 genes are preferably selected from the University of California Santa Cruz (UCSC) database; the typing sites have been disclosed in databases and literature, most of which are collected in the ISBT database, and a small number are derived from literature.

In the present disclosure, the specific primers in the primer set are completely complementary or partially complementary to the above-mentioned target region. Preferably, each pair of specific primers for the target region contains two parts, labeled as 3'-end Tag1 and 5'-end Tag2. A fragment sequence of the 3'-end Tag1 is completely complementary or partially complementary to the target region, and is preferably a nucleic acid molecule with a specific sequence, with an unlimited number of bases, preferably 20 to 40. The 5'-end Tag2 is used to combine with the universal primer during the amplification of the target region, thus completing the specific labeling of the amplification products of the target regions of different samples to be tested. The 5'-end Tag2 has preferably 3 to 20, more preferably 4 to 10 bases.

In the present disclosure, a total of 168 pairs of primers are designed based on the above genes and design principles. Each pair of primers contains mutation sites in the gene. The size of a target region amplified by each pair of primers is 150 bp to 300 bp, with wide coverage and multiple detection sites; the primers have a relatively uniform Tm value (57° C. to 63° C.); the primers show desirable specificity, stability, and uniformity during multiplex amplification, and have non-specific amplification. The primers preferably further include specific modifications, and the modified primers are not easily degraded by nucleases; specifically, the primer-specific modifications include one or more of thio modification, deoxyuracil modification, 5'-reverse dT modification, and 5'-amino modification. A thio-modified primer is a derivative in which the double-bonded oxygen atom on the oligonucleotide chain is replaced by a sulfur atom, and can resist the degradation of nuclease and enhance the stability of the primer. Each deoxythymine in the oligonucleotide sequence of a deoxyuracil-modified primer is replaced by deoxyuracil, and can increase the double-stranded dissolution temperature by 1.7° C., thereby increasing the stability of the double-stranded. The 5' end of the oligonucleotide sequence in a 5'-reverse dT-modified primer contains a reverse dT, thereby forming a cross-link, which can inhibit the degradation of exonucleases during the extension of DNA polymerase. The 5'-amino modification includes C6 amino modification and C12 amino modification. The former can be used to connect some compounds that do not affect its function even near the oligonucleotide, while the latter is used to ligate the affinity purification group and some fluorescent marks.

In the present disclosure, according to the nature of each primer, such as the amplification interval, Tm value, primer sequence, and actual expansion during the later test, the primer set is divided into 3 pools, which are specifically shown in Table 2. The number marked after the sequence in Table 2 is the number of SEQ ID NO. For example, (1) indicates that the nucleotide sequence of a sequence is serialized as SEQ ID NO: 1. The primer set 1 includes: RB_018, RB_023, RB_026, RB_029, RB_032, RB_034, RB_037, RB_039, RB_063, RB_016, RB_053, RB_055, RB_057, RB_048, RB_051, RB_070, RB_064, RB_066, RB_068, RB_118, RB_123, RB_106, RB_108, RB_110, RB_013, RB_003, RB_093, RB_097, RB_099, RB_101, RB_104, RB_042, RB_126, RB_077, RB_079, RB_082, RB_085, RB_087, RB_089, RB_091, RB_125, RB_130, RB_134, RB_137, RB_144, RB_146, RB_149, RB_153, RB_155, RB_157, RB_160, RB_167, RB_138, RB_140, and their nucleotide sequences are shown in SEQ ID NO: 1 to SEQ ID NO: 108 in sequence.

The primer set 2 includes: RB_020, RB_021, RB_022, RB_025, RB_027, RB_031, RB_035, RB_058, RB_060, RB_062, RB_015, RB_054, RB_046, RB_049, RB_052, RB_071, RB_072, RB_074, RB_065, RB_067, RB_069, RB_117, RB_120, RB_122, RB_105, RB_109, RB_112, RB_114, RB_010, RB_012, RB_002, RB_005, RB_007, RB_095, RB_098, RB_102, RB_041, RB_043, RB_045, RB_127, RB_081, RB_084, RB_088, RB_075, RB_131, RB_133, RB_136, RB_143, RB_147, RB_150, RB_152, RB_156, RB_158, RB_161, RB_163, RB_165, RB_141, and their nucleotide sequences are shown in SEQ ID NO: 109 to SEQ ID NO: 222 in sequence.

The primer set 3 includes: RB_019, RB_024, RB_028, RB_030, RB_033, RB_036, RB_038, RB_059, RB_061, RB_017, RB_056, RB_047, RB_050, RB_073, RB_116, RB_119, RB_121, RB_124, RB_107, RB_111, RB_113, RB_115, RB_009, RB_011, RB_014, RB_001, RB_004, RB_006, RB_008, RB_092, RB_094, RB_096, RB_100, RB_103, RB_040, RB_044, RB_076, RB_078, RB_080, RB_083, RB_086, RB_090, RB_128, RB_129, RB_132, RB_135, RB_142, RB_145, RB_148, RB_151, RB_154, RB_159, RB_162, RB_164, RB_166, RB_168, RB_139, and their nucleotide sequences are shown in SEQ ID NO: 223 to SEQ ID NO: 336 in sequence.

TABLE 2

Information of primer pairs

| Primer ID | Target gene fragment | Sequence of forward primer | Sequence of reverse primer |
| --- | --- | --- | --- |
| RB_001 | FUT1-1 | AGTCTCCCTGGCTCTCAAGG (SEQ ID NO: 273) | CGATGGACAGGAGGCTACAC (SEQ ID NO: 274) |
| RB_002 | FUT1-2 | CAGAGTCTGGCAGGGTGAAG (SEQ ID NO: 169) | TTTTCGTGGTCACCAGCAAC (SEQ ID NO: 170) |
| RB_003 | FUT1-3 | GTGTAGCCTCCTGTCCATCG (SEQ ID NO: 51) | GTGGGGACTATCTGCAGGTT (SEQ ID NO: 52) |
| RB_004 | FUT1-4 | TTGCTGGTGACCACGAAAAC (SEQ ID NO: 275) | CTTCCACCATCTCCGGGAAC (SEQ ID NO: 276) |
| RB_005 | FUT1-5 | CACACTCTGCGCCTCTTCC (SEQ ID NO: 171) | TTTATCCTGCCTGCCATGCA (SEQ ID NO: 172) |
| RB_006 | FUT1-6 | CTCAAGTCCGCGTACTCCTC (SEQ ID NO: 277) | CACCTGGACTGTCTACCCCA (SEQ ID NO: 278) |
| RB_007 | FUT1-7 | CGTGGCATACTGTCCCATCT (SEQ ID NO: 173) | CTGGCCTTCCTGCTAGTCTG (SEQ ID NO: 174) |
| RB_008 | FUT1-8 | CGGTCTGGACACAGGATCG (SEQ ID NO: 279) | CCTGGGACTAAGGAGTGCTG (SEQ ID NO: 280) |
| RB_009 | FUT2-1 | GCCTCCATCTCCCAGCTAAC (SEQ ID NO: 267) | AGGCGGCCTATTGCATTGAT (SEQ ID NO: 268) |
| RB_010 | FUT2-2 | CGATCAATGCAATAGGCCGC (SEQ ID NO: 165) | GGGATGTGGCGGTATTCCTC (SEQ ID NO: 166) |
| RB_011 | FUT2-3 | CCTGGCAGAACTACCACCTG (SEQ ID NO: 269) | ATAGTCCCCTCGGCGAACAT (SEQ ID NO: 270) |
| RB_012 | FUT2-4 | GAGGAGGCCCAGAAGTTCCT (SEQ ID NO: 167) | CAGCAAACACCACATCACCG (SEQ ID NO: 168) |
| RB_013 | FUT2-5 | TCGTGGTCACCAGTAATGGC (SEQ ID NO: 49) | GTCGGGGAGGGTGTAATTGG (SEQ ID NO: 50) |
| RB_014 | FUT2-6 | GCGGAGACACCATCTACCTG (SEQ ID NO: 271) | GAGGGAGGCAGAGAAGGAGA (SEQ ID NO: 272) |
| RB_015 | SLC35C1-1 | AACCTCTGCCTCAAGTACGTC (SEQ ID NO: 129) | TGACCACTCTATCCCCCGTG (SEQ ID NO: 130) |
| RB_016 | SLC35C1-2 | GAGGGCCGCAATACTCAGTC (SEQ ID NO: 19) | TTCGTGGTGTAGATGGCGTT (SEQ ID NO: 20) |
| RB_017 | SLC35C1-3 | CATCGGCTACGTGACAGGAC (SEQ ID NO: 241) | TCTTCTCGCTGTCTTTGGGG (SEQ ID NO: 242) |

TABLE 2 -continued

Information of primer pairs

| Primer ID | Target gene fragment | Sequence of forward primer | Sequence of reverse primer |
|---|---|---|---|
| RB_018 | RhD-1 | GCCCTCAAGTAGGTGTTGGA (SEQ ID NO: 1) | CCCTGCTATTTGCTCCTGTGA (SEQ ID NO: 2) |
| RB_019 | RhD-2 | AAATCTCGTCTGCTTCCCCC (SEQ ID NO: 223) | GATCCAGCCACCATCCCAAT (SEQ ID NO: 224) |
| RB_020 | RhD-3 | AAGATCTGACCGTGATGGCG (SEQ ID NO: 109) | GAACCTGTCCTTTCGGGGTC (SEQ ID NO: 110) |
| RB_021 | RhD-4 | TTCTCAGTCGTCCTGGCTCTC (SEQ ID NO: 111) | TTCAAAACCCTGGAAACCCCA (SEQ ID NO: 112) |
| RB_022 | RhD-5 | GAGGATGCCGACACTCACTG (SEQ ID NO: 113) | TCAGCCCAAGTAGGAGACCA (SEQ ID NO: 114) |
| RB_023 | RhD-6 | GACCTTTGGAGCAGGAGTGT (SEQ ID NO: 3) | GTCCTGTTAGACCCAAGTGCT (SEQ ID NO: 4) |
| RB_024 | RhD-7 | CTCGAGGCTCAGACCTTTGG (SEQ ID NO: 225) | TTAGACCCAAGTGCTGCCCA (SEQ ID NO: 226) |
| RB_025 | RhD-8 | GCTTCCTTTACCCACACGCT (SEQ ID NO: 115) | CCTTCAGCCAAAGCAGAGGA (SEQ ID NO: 116) |
| RB_026 | RhD-9 | GTCTCACCTGCCAATCTGCT (SEQ ID NO: 5) | CCCAGCTAAGGACTCTGCAC (SEQ ID NO: 6) |
| RB_027 | RhD-10 | CTGATGCCCAAGTGACCACC (SEQ ID NO: 117) | AGGAGATGGGGCACATAGAC (SEQ ID NO: 118) |
| RB_028 | RhD-11 | TGAGATTAAAAATCCTGTGCTCCA (SEQ ID NO: 227) | GTTCCTCCTGCAATGCTCCT (SEQ ID NO: 228) |
| RB_029 | RhD-12 | GGCTGTTTCAAGAGATCAAGCC (SEQ ID NO: 7) | TTCTCTGACTCCAGTGCCTG (SEQ ID NO: 8) |
| RB_030 | RhCE-13 | TCTGTCTCTGACCTTGTTTCAT (SEQ ID NO: 229) | GGCTGTTTCAAGAGATCAAGCC (SEQ ID NO: 230) |
| RB_031 | RhCE-14 | GAAAGGTGGCCTCACACTGA (SEQ ID NO: 119) | CCTGGCAATGGCACTACTGA (SEQ ID NO: 120) |
| RB_032 | RhCE-15 | CCCAGCTAAGGACTCTGCAC (SEQ ID NO: 9) | GTCTCACCTGCCAATCTGCT (SEQ ID NO: 10) |
| RB_033 | RhCE-16 | CTTCAGCCAAAGCAGAGAGC (SEQ ID NO: 231) | GCTGGTCACTTGCAGCAAGA (SEQ ID NO: 232) |
| RB_034 | RhCE-17 | TTAGACCCAAGTGCTGCCCA (SEQ ID NO: 11) | CTCGAGGCTCAGACCTTTGG (SEQ ID NO: 12) |
| RB_035 | RhCE-18 | CTCAGCCCAAGTATGAGACCA (SEQ ID NO: 121) | TTTCTCCAAGGACCATCAGGG (SEQ ID NO: 122) |
| RB_036 | RhCE-19 | AATGGAGCTTTTGGCCCTTTTC (SEQ ID NO: 233) | TCAGTCATCCTGGCTCTCCTTC (SEQ ID NO: 234) |
| RB_037 | RhCE-20 | GAACCTGTCCTTTCGGGGTC (SEQ ID NO: 13) | AAGATCTGACCGTGATGGCG (SEQ ID NO: 14) |
| RB_038 | RhCE-21 | GATCCAGCCACCATCCCAAT (SEQ ID NO: 235) | AAATCTCGTCTGCTTCCCCC (SEQ ID NO: 236) |
| RB_039 | RhCE-22 | CCTGCTATTTGCTCCTGTGA (SEQ ID NO: 15) | CTCAAGCCCTCAAGTAGGTGT (SEQ ID NO: 16) |
| RB_040 | GYPA-1 | TGGTGTACAACATGATGGTTTGA (SEQ ID NO: 291) | TGTACAACAGGGTGAATGGAGT (SEQ ID NO: 292) |
| RB_041 | GYPA-2 | CTCCTAGAGCTGTTCACACTGG (SEQ ID NO: 181) | AGGCAAGGTGATGTTATGCTGA (SEQ ID NO: 182) |
| RB_042 | GYPA-3 | AGGCATTTGAAACAAGCAATGGA (SEQ ID NO: 63) | AAGGAAACCCGCAGAACAGT (SEQ ID NO: 64) |

TABLE 2 -continued

Information of primer pairs

| Primer ID | Target gene fragment | Sequence of forward primer | Sequence of reverse primer |
|---|---|---|---|
| RB_043 | GYPA-4 | GCAGTGACAGGTCCCCTAAA (SEQ ID NO: 183) | CTGCTCAGTCACCTCGTTCT (SEQ ID NO: 184) |
| RB_044 | GYPA-5 | TGTCACGAAAGCTTGAGAACTG (SEQ ID NO: 293) | GCTCTATGTCCACGCAGTCA (SEQ ID NO: 294) |
| RB_045 | GYPA-6 | GCAGTGACAGGTCCCCTAAA (SEQ ID NO: 185) | TTATGGTCCGCTCAGTCACC (SEQ ID NO: 186) |
| RB_046 | JK-1 | TGGCTAATCTGGAGGGCTCT (SEQ ID NO: 133) | ACCTTTAAGCTGGTTGGCAAG (SEQ ID NO: 134) |
| RB_047 | JK-2 | CTTCCAGACAAACCCGTGGT (SEQ ID NO: 245) | TGCCCACAGTAACTGGTCAG (SEQ ID NO: 246) |
| RB_048 | JK-3 | GCAAGTGCAACCAAAGCTCA (SEQ ID NO: 27) | GGCATTTTGAAAACCAATTGTAACT (SEQ ID NO: 28) |
| RB_049 | JK-4 | CAGCCTGCTTTGTCACATGC (SEQ ID NO: 135) | GCGAATGTGAGAAGCCAGTG (SEQ ID NO: 136) |
| RB_050 | JK-5 | ACCAGTGGGAGTTGGTCAGA (SEQ ID NO: 247) | CCCATTGGTCCCTAGGAAGC (SEQ ID NO: 248) |
| RB_051 | JK-6 | CCTGAGTTCTGACCCCTCCT (SEQ ID NO: 29) | CAGAACCCTGGCCCTGATTT (SEQ ID NO: 30) |
| RB_052 | JK-7 | GTAATCAGGGCACTGTGCATTC (SEQ ID NO: 137) | TGGACTTCAGGAGCATTTCCC (SEQ ID NO: 138) |
| RB_053 | DI-1 | GCCACTCACACACTGAAGCTC (SEQ ID NO: 21) | TGGGGTGTGATAGGCACTGAC (SEQ ID NO: 22) |
| RB_054 | DI-2 | ATGAAGACCAGCAGAGCAGG (SEQ ID NO: 131) | AGTTCCCAAGTGCCTCCAAC (SEQ ID NO: 132) |
| RB_055 | DI-3 | GCTGTTCTTGAACTTGCGCA (SEQ ID NO: 23) | GGTATTTTCCAGCCCAAGCC (SEQ ID NO: 24) |
| RB_056 | DI-4 | CAACACCACCAGCAGGATGA (SEQ ID NO: 243) | CCCTGCTGGTGTTTGAGGAA (SEQ ID NO: 244) |
| RB_057 | DI-5 | TGCACTGCAGTGGAGATCAG (SEQ ID NO: 25) | ACTCTTGCCTCTGACCCTCT (SEQ ID NO: 26) |
| RB_058 | FY-1 | CCATCCTGGTCTCTTGGTGC (SEQ ID NO: 123) | AGGCCATCAGAGTTACACCG (SEQ ID NO: 124) |
| RB_059 | FY-2 | ATGGCCTCCTCTGGGTATGT (SEQ ID NO: 237) | AGCATGAAGAGGACAGTGCT (SEQ ID NO: 238) |
| RB_060 | FY-3 | GCACTGCCCTTCTTCATCCT (SEQ ID NO: 125) | GCTGAGCCATACCAGACACA (SEQ ID NO: 126) |
| RB_061 | FY-4 | TCTTCCGCTGGCAGCTCT (SEQ ID NO: 239) | CCACTCCCCAAAATTCCCACA (SEQ ID NO: 240) |
| RB_062 | FY-5 | CACTGTAGCCTGTCTTGCCA (SEQ ID NO: 127) | AAAATTGCCAGGGCTTCTGC (SEQ ID NO: 128) |
| RB_063 | FY-6 | TTGTCAACATGTCTGGCCCA (SEQ ID NO: 17) | AAGAAACCACCCGCTTCACA (SEQ ID NO: 18) |
| RB_064 | FUT3-1 | GAGAGAGGGTTGGCCACAAA (SEQ ID NO: 33) | AGGAGCTGGACAAGGACCA (SEQ ID NO: 34) |
| RB_065 | FUT3-2 | TGGTCCTTGTCCAGCTCCT (SEQ ID NO: 145) | CCAAGGGGACCATGATGGAG (SEQ ID NO: 146) |
| RB_066 | FUT3-3 | ACAGCGTCTCCATCATGGTC (SEQ ID NO: 35) | CAGCGACTCCGACATCTTCA (SEQ ID NO: 36) |
| RB_067 | FUT3-4 | CTGAGTCCGGCTTCCAGTTG (SEQ ID NO: 147) | CCAACCCTAAGTCACGCCTC (SEQ ID NO: 148) |

TABLE 2 -continued

Information of primer pairs

| Primer ID | Target gene fragment | Sequence of forward primer | Sequence of reverse primer |
|---|---|---|---|
| RB_068 | FUT3-5 | GCGTGACTTAGGGTTGGACA (SEQ ID NO: 37) | TTCTCCTACCTGCGTGTGTC (SEQ ID NO: 38) |
| RB_069 | FUT3-6 | TGGAAAGGCCATGTCCGTAG (SEQ ID NO: 149) | ACTCTGACCCATGGATCCCC (SEQ ID NO: 150) |
| RB_070 | FUT6-1 | GCGTGTCTGGTACCTGGATT (SEQ ID NO: 31) | CCCAGCAGAAGCAACTACGA (SEQ ID NO: 32) |
| RB_071 | FUT6-2 | TCGTAGTTGCTTCTGCTGGG (SEQ ID NO: 139) | GGAACCATGATGGAGACGCT (SEQ ID NO: 140) |
| RB_072 | FUT6-3 | GTCTTGGCCGAGAGGTTGAG (SEQ ID NO: 141) | TCATGTACAACCCCAGTGCC (SEQ ID NO: 142) |
| RB_073 | FUT6-4 | TTGGGGACTCCATGCTGAAC (SEQ ID NO: 249) | ACAAACCCATAGCTCTGCCC (SEQ ID NO: 250) |
| RB_074 | FUT6-5 | ATGGGTTTGTTAAAAGGCCACG (SEQ ID NO: 143) | TCTCCCCACTTCCCAGATACT (SEQ ID NO: 144) |
| RB_075 | FUT7-7 | GTGGGTGTGGCTAGGAGACT (SEQ ID NO: 195) | TCACCATCCTTGTCTGGCAC (SEQ ID NO: 196) |
| RB_076 | KEL-1 | ACAGCGGAAATACCTGGCAA (SEQ ID NO: 295) | CACTTGATCCCCTGGTTCCC (SEQ ID NO: 296) |
| RB_077 | KEL-2 | GGGACTTCCATGAGCTTCAGT (SEQ ID NO: 67) | GGGTTTTGGGTACTGTGTGGA (SEQ ID NO: 68) |
| RB_078 | KEL-3 | CCAACGTCTGCAGCATTCTCT (SEQ ID NO: 297) | ATGCTCCTGGGAGCTGATTC (SEQ ID NO: 298) |
| RB_079 | KEL-4 | CTCCCTTGTGGTCTTCCCTT (SEQ ID NO: 69) | CTCCCTTGTGGTCTTCCCTT (SEQ ID NO: 70) |
| RB_080 | KEL-5 | ATCATAACACCTGTCGGCCC (SEQ ID NO: 299) | GGGAGGGACTGTGTAGGTCT (SEQ ID NO: 300) |
| RB_081 | KEL-6 | CATACCTGTGTTGGGGGTGA (SEQ ID NO: 189) | TGGTCCCATTGGTGTTTGTCA (SEQ ID NO: 190) |
| RB_082 | KEL-7 | GGAGGGTCAGAGAAGTGACGA (SEQ ID NO: 71) | GCCACTGGGCTGTATACTCA (SEQ ID NO: 72) |
| RB_083 | KEL-8 | ATCCCCATCTCGCTTGTTCC (SEQ ID NO: 301) | AGCCCTTTTCCAAGGGTCAG (SEQ ID NO: 302) |
| RB_084 | KEL-9 | TGCCCAATTCCCCAATCACA (SEQ ID NO: 191) | TCCTGAACAGGAGCCACTCA (SEQ ID NO: 192) |
| RB_085 | KEL-10 | AATACACCCGCTCCTCTCCT (SEQ ID NO: 73) | GGAGCTGCCTTCACGAGTAT (SEQ ID NO: 74) |
| RB_086 | KEL-11 | GCGGCGAACCTCTGCTTTAG (SEQ ID NO: 303) | ATCCCCTCCCCCAGTTAGC (SEQ ID NO: 304) |
| RB_087 | KEL-12 | GAGAGGAAGATCCCCATGCC (SEQ ID NO: 75) | CCTTCCTCCAGATCTTTCGGG (SEQ ID NO: 76) |
| RB_088 | KEL-13 | GTCTCCTCCCAGCAAGGTTC (SEQ ID NO: 193) | CCAGTCTCTCTTGTGCCCAG (SEQ ID NO: 194) |
| RB_089 | KEL-14 | GTCCAACTGTGTCTTCGCCA (SEQ ID NO: 77) | AGAGCCGATCCAGACAATGG (SEQ ID NO: 78) |
| RB_090 | KEL-15 | AGCATCTTCCACCCTGCTTT (SEQ ID NO: 305) | AGCCCTTGTCTTTTTGCCTCT (SEQ ID NO: 306) |
| RB_091 | KEL-16 | GGCTGACTAGGTTAGGGGGT (SEQ ID NO: 79) | TCACCTCTTGGTTCCTCCCA (SEQ ID NO: 80) |
| RB_092 | A4GALT-1 | GGGCCCCTCACAAGTACATT (SEQ ID NO: 281) | CTGAGGCCTTCTACCCCATC (SEQ ID NO: 282) |

TABLE 2 -continued

Information of primer pairs

| Primer ID | Target gene fragment | Sequence of forward primer | Sequence of reverse primer |
|---|---|---|---|
| RB_093 | A4GALT-2 | ATGGGGTAGAAGGCCTCAGG (SEQ ID NO: 53) | TCTCAAGAACCTGCGGAACC (SEQ ID NO: 54) |
| RB_094 | A4GALT-3 | CCGTTGTAGTGGTCCACGAA (SEQ ID NO: 283) | CTGGGAGCCCTACCTGCT (SEQ ID NO: 284) |
| RB_095 | A4GALT-4 | CATGAGTGCGATCCTGGAGG (SEQ ID NO: 175) | TTCATGTGCTCGGTGGAGTC (SEQ ID NO: 176) |
| RB_096 | A4GALT-5 | CGGAAGCCCTTTCATCAGGA (SEQ ID NO: 285) | ATCTACTGGCACGTTGTGGG (SEQ ID NO: 286) |
| RB_097 | A4GALT-6 | CCCACAACGTGCCAGTAGAT (SEQ ID NO: 55) | TTGGCTCTGGCTGATGTTCA (SEQ ID NO: 56) |
| RB_098 | A4GALT-7 | CCTCCTCCCCACTGCGAG (SEQ ID NO: 177) | CGCAAGGGCTCTGGGGAC (SEQ ID NO: 178) |
| RB_099 | B3GALNT1-1 | GTAAGCCAGCACACTGACCT (SEQ ID NO: 57) | GCAGCCCATGGCTTTTCTTC (SEQ ID NO: 58) |
| RB_100 | B3GALNT1-2 | GGGCTGCAATCACACGTCTC (SEQ ID NO: 287) | TCCTTTCAAGGTGTTCCCTCC (SEQ ID NO: 288) |
| RB_101 | B3GALNT1-3 | TCCTTGGCACCAAATCTCTGG (SEQ ID NO: 59) | GCCCCAATGCCAAGTACGTA (SEQ ID NO: 60) |
| RB_102 | B3GALNT1-4 | TCAGTGTCTGTCTTCATTACGT (SEQ ID NO: 179) | CCAGGCAGGCCATTAGAGTT (SEQ ID NO: 180) |
| RB_103 | B3GALNT1-5 | GGCATTGGGGCAAAACTCAG (SEQ ID NO: 289) | TGACCTCCCACCCTTCAGAT (SEQ ID NO: 290) |
| RB_104 | B3GALNT1-6 | ATCTGAAGGGTGGGAGGTCA (SEQ ID NO: 61) | TCTCTGGACTGTCCTTCCGA (SEQ ID NO: 62) |
| RB_105 | LU-1 | AGCTCAGTTGCTCTCTTGCA (SEQ ID NO: 157) | AACAAGGAGTGTGGCTTGGT (SEQ ID NO: 158) |
| RB_106 | LU-2 | AGCTGCAGAGAGAAAGGACC (SEQ ID NO: 43) | CACACGTAGTCTCGCTCGTC (SEQ ID NO: 44) |
| RB_107 | LU-3 | CTGAGATGCAGGGCTCTGAG (SEQ ID NO: 259) | GGATGCCCGAGGACACTTAC (SEQ ID NO: 260) |
| RB_108 | LU-4 | CGTGTTTGGTAAGTGTCCTCG (SEQ ID NO: 45) | CTGTCCCTCCTCCTCCAG (SEQ ID NO: 46) |
| RB_109 | LU-5 | CGACTTCAGAGTCCCAGCTC (SEQ ID NO: 159) | GCTGCTCACCTGGGTTCAT (SEQ ID NO: 160) |
| RB_110 | LU-6 | CGATCTCTCCCAGAGGGCTA (SEQ ID NO: 47) | CTCATGAGGTGTGGAGCCTG (SEQ ID NO: 48) |
| RB_111 | LU-7 | CCTTAGATCCCACGGAGCAC (SEQ ID NO: 261) | CAGATCAGGTGGCTGCCTAA (SEQ ID NO: 262) |
| RB_112 | LU-8 | CCATGCTGTCGCTCAGTTCT (SEQ ID NO: 161) | CGAGCAGAAGATGGAGTCCC (SEQ ID NO: 162) |
| RB_113 | LU-9 | CTGGACAAACAGGACGAGTTC (SEQ ID NO: 263) | CTCCAGCTGAGTTTGGGGTC (SEQ ID NO: 264) |
| RB_114 | LU-10 | CTGATCGGAGCCTCCATAGC (SEQ ID NO: 163) | CTCACTGCAGGGACAGGATG (SEQ ID NO: 164) |
| RB_115 | LU-11 | GCACCGGTGAGTGACTGAG (SEQ ID NO: 265) | TCATTGCAGATAGCAGGCCAC (SEQ ID NO: 266) |
| RB_116 | KLF1-1 | CCCATCCCCAGTCACTAGGA (SEQ ID NO: 251) | GGACATGACTGGGCAGACAG (SEQ ID NO: 252) |
| RB_117 | KLF1-2 | CCTCTGCAACCCTTCTTCCC (SEQ ID NO: 151) | GACTGCAGAGGATCCAGGTG (SEQ ID NO: 152) |

TABLE 2 -continued

Information of primer pairs

| Primer ID | Target gene fragment | Sequence of forward primer | Sequence of reverse primer |
|---|---|---|---|
| RB_118 | KLF1-3 | TCTCGGCTATCACACCTGGA (SEQ ID NO: 39) | GCTCCTCGGGTGGCTACTTC (SEQ ID NO: 40) |
| RB_119 | KLF1-4 | TACCCGGACAGTAGCCCGTA (SEQ ID NO: 253) | GGCTTTTGGGTTCGGAGGAT (SEQ ID NO: 254) |
| RB_120 | KLF1-5 | GGAAGTAGCCACCCGAGGAG (SEQ ID NO: 153) | CGAGACTCTGGGCGCATATG (SEQ ID NO: 154) |
| RB_121 | KLF1-6 | ATCCTCCGAACCCAAAAGCC (SEQ ID NO: 255) | CCCTCCACGTGAAGTCTGAG (SEQ ID NO: 256) |
| RB_122 | KLF1-7 | GAGGAGATCCAGGTCCCAGG (SEQ ID NO: 155) | GACAGGCAAACAAGACCCCT (SEQ ID NO: 156) |
| RB_123 | KLF1-8 | CCCCAAGATCTGTGACTGTGG (SEQ ID NO: 41) | CCCTCGAAGGGGCTATCACA (SEQ ID NO: 42) |
| RB_124 | KLF1-9 | GGTCCAGGTGCTGGGTAAAA (SEQ ID NO: 257) | TGATAGCAGCCTCCAACGTC (SEQ ID NO: 258) |
| RB_125 | GATA1-1 | CCTTTCCCTGGACCCCTACT (SEQ ID NO: 81) | ACACACCCACAATTTCAGGACT (SEQ ID NO: 82) |
| RB_126 | YT-1 | TAGACCCATGGTGGCTTTCC (SEQ ID NO: 65) | CCTTCGTGCCTGTGGTAGAT (SEQ ID NO: 66) |
| RB_127 | YT-2 | ACACTCTGGAAGGTTGTAGCG (SEQ ID NO: 187) | TCCTTCTCCTCCTCCTCTGG (SEQ ID NO: 188) |
| RB_128 | ERMAP-1 | TGCTTGGCAGGCAGTATCTT (SEQ ID NO: 307) | CCCTGACAGCCTTTTCCAGT (SEQ ID NO: 308) |
| RB_129 | ERMAP-2 | CTCCCAGTTGGCCTTGTCTC (SEQ ID NO: 309) | TCTCTCACTAGCACCGTCCT (SEQ ID NO: 310) |
| RB_130 | ERMAP-3 | GGATGGGAAGGACCAGGATG (SEQ ID NO: 83) | TTGCCACAAAATGACCCTGGG (SEQ ID NO: 84) |
| RB_131 | ART4-1 | TGCTCAGGTTCCCAGTTGAC (SEQ ID NO: 197) | CTACACAGGGGCCACCATTC (SEQ ID NO: 198) |
| RB_132 | ART4-2 | GAATGGTGGCCCCTGTGTAG (SEQ ID NO: 311) | TAGAGCCATGGCCTCTGTTG (SEQ ID NO: 312) |
| RB_133 | ART4-3 | AGCTGGATTGCTGAGGTGAG (SEQ ID NO: 199) | AAAAGCCCACTTAGCCTGGC (SEQ ID NO: 200) |
| RB_134 | ART4-4 | GGCCATGGCTCTAGTAAAGTCA (SEQ ID NO: 85) | TCGACTTCGACTTCGCACC (SEQ ID NO: 86) |
| RB_135 | ART4-5 | TTAAGCCAGGCTAAGTGGGC (SEQ ID NO: 313) | AAATCTGCAACCACATTCACCA (SEQ ID NO: 314) |
| RB_136 | ART4-6 | CGGGTGAATGCTCTGTTGGA (SEQ ID NO: 201) | TCAGGATGAAGCTGCAAGGG (SEQ ID NO: 202) |
| RB_137 | ART4-7 | TCAGTCTCATCCGTAACCGT (SEQ ID NO: 87) | GACTTCGGCATTCCCCTGAA (SEQ ID NO: 88) |
| RB_138 | AQP1-1 | CCGGCCCTATAAATAGGCCC (SEQ ID NO: 105) | CGACACCTTCACGTTGTCCT (SEQ ID NO: 106) |
| RB_139 | AQP1-2 | GGGCTTCAAATACCCGGTGG (SEQ ID NO: 335) | GGTGATGCCTGAGAGGATGG (SEQ ID NO: 336) |
| RB_140 | AQP1-3 | CCGTGCCCTCATGTACATCA (SEQ ID NO: 107) | TCTCTACGTGACCTCCAGCA (SEQ ID NO: 108) |
| RB_141 | AQP1-4 | TTCTCCCTCCAACCTCTCCC (SEQ ID NO: 221) | GGTCAGGCTTACCATGGGAC (SEQ ID NO: 222) |
| RB_142 | ICAM4-1 | GCTCAATTGCAGCAACAGCT (SEQ ID NO: 315) | GCCCCTGTCCCTCACTGTA (SEQ ID NO: 316) |

TABLE 2 -continued

Information of primer pairs

| Primer ID | Target gene fragment | Sequence of forward primer | Sequence of reverse primer |
|---|---|---|---|
| RB_143 | ABCG2-1 | CACCTGCATTCCTTGGCTCT (SEQ ID NO: 203) | CTGACCTCGTAATCCACCCG (SEQ ID NO: 204) |
| RB_144 | ABCG2-2 | CGGCCTCCCAAAGTACTAGG (SEQ ID NO: 89) | CGAGCAAAAGGGGAAAAGCC (SEQ ID NO: 90) |
| RB_145 | ABCG2-3 | GCGGGTTCAAGCGATTCTAC (SEQ ID NO: 317) | CCTAGTACTTTGGGAGGCCG (SEQ ID NO: 318) |
| RB_146 | ABCG2-4 | GCTCAGGATCTCAGGATGCG (SEQ ID NO: 91) | GTGCTGTGCCCACTCAAAAG (SEQ ID NO: 92) |
| RB_147 | ABCG2-5 | GTTTGCACCAGGGCATCATT (SEQ ID NO: 205) | GCCTTTGGTTAAGACCGAGC (SEQ ID NO: 206) |
| RB_148 | ABCG2-6 | TCTCTAGGACTGAGAAGGGAGT (SEQ ID NO: 319) | AACCCACTGAGCACAGAAGT (SEQ ID NO: 320) |
| RB_149 | ABCG2-7 | TGGCAGTGCAGGTTTCTCTC (SEQ ID NO: 93) | GTTTCATGTTGGCCAGGCTG (SEQ ID NO: 94) |
| RB_150 | ABCG2-8 | ATCTTTTGGCTTCCCTGGGC (SEQ ID NO: 207) | CTTGTCCAACGTGCATGTGG (SEQ ID NO: 208) |
| RB_151 | ABCG2-9 | TGGAGTTGCACTCTACCTCA (SEQ ID NO: 321) | TGAAAGCCCATGGATCAACCT (SEQ ID NO: 322) |
| RB_152 | ABCG2-10 | CGGGGAAGCCATTGGTGTTT (SEQ ID NO: 209) | AGTTGTGCCTGTCTTCCCAT (SEQ ID NO: 210) |
| RB_153 | ABCG2-11 | AGGCCACGTGATTCTTCCAC (SEQ ID NO: 95) | AGGCTCCTTTAAGGAACAGTGG (SEQ ID NO: 96) |
| RB_154 | ABCG2-12 | CATTCGCGCACAACTCACTT (SEQ ID NO: 323) | TGTTTACCTTGCCCTGCTCC (SEQ ID NO: 324) |
| RB_155 | ABCG2-13 | AGCTTGGGAATGCAGTCACA (SEQ ID NO: 97) | TGGTAGGGACTTGAAGAGGGT (SEQ ID NO: 98) |
| RB_156 | ABCG2-14 | GCAAACACAGTTCAGACTCACC (SEQ ID NO: 211) | TCCCAAACATACGGTGACCT (SEQ ID NO: 212) |
| RB_157 | ABCG2-15 | CTCTGACCTGCTGCTATGGC (SEQ ID NO: 99) | ACAACATTGGAGACCGAGGG (SEQ ID NO: 100) |
| RB_158 | ABCG2-16 | GGTGCAACTGACTTCACCCA (SEQ ID NO: 213) | AACAGACAAGTCTAGCCTGCC (SEQ ID NO: 214) |
| RB_159 | ABCG2-17 | GAGCTATAGAGGCCTGGGGA (SEQ ID NO: 325) | ATCCACTGATTGCAAAGCCAC (SEQ ID NO: 326) |
| RB_160 | ABCG2-18 | AGCCACCACATTGCTAAACT (SEQ ID NO: 101) | TAGCCTTACCTCCCTCACCC (SEQ ID NO: 102) |
| RB_161 | ABCG2-19 | AGTATCCCAAGGCCTCCTGA (SEQ ID NO: 215) | CAAAGTCAGGCTGAACTAGAGC (SEQ ID NO: 216) |
| RB_162 | ABCG2-20 | TCAGGAGCAAAAGGACAGCA (SEQ ID NO: 327) | TCTTACAGGACTGGCACACG (SEQ ID NO: 328) |
| RB_163 | ABCG2-21 | ACCTTGGAGTCTGCCACTTT (SEQ ID NO: 217) | AAGGATGATGTTGTGATGGGCA (SEQ ID NO: 218) |
| RB_164 | ABCG2-22 | GTTGTTGCAAGCCGAAGAGC (SEQ ID NO: 329) | CAGGCTTTGCAGACATCTATGG (SEQ ID NO: 330) |
| RB_165 | ABCG2-23 | TCAGCCAAAGCACTTACCCA (SEQ ID NO: 219) | TATAGCATGTGTTGGAGGGAAA (SEQ ID NO: 220) |
| RB_166 | ABCG2-24 | AGAACCAGACCTGACATGCG (SEQ ID NO: 331) | CATGAAACCTGGTCTCAACGC (SEQ ID NO: 332) |
| RB_167 | ABCG2-25 | GCCAGTTTCTTGGAAATAGCCA (SEQ ID NO: 103) | GGAAACACCAATGGCTTCCC (SEQ ID NO: 104) |

TABLE 2 -continued

Information of primer pairs

| Primer ID | Target gene fragment | Sequence of forward primer | Sequence of reverse primer |
|---|---|---|---|
| RB_168 | ABCG2-26 | CGGGGAAGCCATTGGTGTTT (SEQ ID NO: 333) | AGTTGTGCCTGTCTTCCCAT (SEQ ID NO: 334) |

The present disclosure further provides a kit for simultaneously detecting genotyping of 17 RBC blood group systems, including the primer set, and a PCR reaction solution and a quality control.

In the present disclosure, the first primer set, the second primer set, and the third primer set in the primer set are packaged independently. The PCR reaction solution is preferably PCR Buffer, high-fidelity DNA polymerase, and nuclease-free water. In the examples, enzyme mixtures Pxp-1st-mix and Pxp-2nd-mix that mix the PCR Buffer with the high-fidelity DNA polymerase are selected, and the enzyme mixtures Pxp-1st-mix and Pxp-2nd-mix each preferably include commercial ingredients, such as main components in the enzyme mixture: high-fidelity enzyme and 5×HF PCR Buffer: Thermo Fisher scientific's "Phusion Hot Start II DNA Polymerase (2 U/μL)", F565L; dNTP (dATP, dTTP, dCTP, dGTP): Sangon (BBI) A620046, A670046, A640046, 660046.

In the present disclosure, the quality control is preferably a human normal genomic DNA.

The present disclosure further provides a method for detecting genotyping of 17 RBC blood group systems, including the following steps as shown in FIG. 1: (1) subjecting three capture and amplification systems to first amplification separately to obtain three first amplification products, where the three capture and amplification systems are prepared by using a nucleic acid extracted from a sample as a template and a first primer set, a second primer set, and a third primer set, respectively;

(2) purifying the three first amplification products separately, and subjecting three resulting purified first amplification products to second amplification with a sequencing universal adapter carrying an index separately to obtain three second amplification products; and (3) purifying and mixing the three second amplification products to allow sequencing to obtain the genotyping of the RBC blood group systems.

In the present disclosure, three capture and amplification systems are subjected to first amplification separately to obtain three first amplification products, where the three capture and amplification systems are prepared by using a nucleic acid extracted from a sample as a template and a first primer set, a second primer set, and a third primer set, respectively. Preferably, the sample is extracted using magnetic beads, the concentration and purity are measured, and the nucleic acid is quantitatively diluted. Since nano-scale superparamagnetic carboxyl magnetic beads can reversibly adsorb nucleic acid molecules under different salt concentrations and hydrophobic environments, the nucleic acid molecules can be specifically adsorbed based on this. High-purity nucleic acid samples can be obtained through subsequent washing and elution. Concentration and purity are measured using Qubit or NanoDrop. According to a measured nucleic acid sample concentration, the nucleic acid sample is diluted to 50-250 ng/μL with 10 mM Tris-HCl, preferably 100-200 ng/μL serves as a starting concentration for amplification and library construction.

In the examples of the present disclosure, a quality of the diluted nucleic acid is preferably further evaluated by 1.5% agarose gel electrophoresis at 150 V for 30 min. The quality of the extracted nucleic acid is determined based on the uniformity and integrity of the agarose gel electrophoresis results. High integrity or slight degradation of the nucleic acid does not affect the library construction. The extracted nucleic acids are grouped and labeled separately after passing the concentration measurement, purity measurement, and agarose gel electrophoresis test. The sample is selected from the group consisting of a whole blood sample, a plasma sample, and a paraffin tissue sample. Nucleic acids are extracted from the above samples and diluted to the starting concentration for amplification and library construction. 3 tubes of capture and amplification system are constructed according to the grouping of the pools, where a primer pair of each pool is regarded as 1 tube. The three capture and amplification systems each have a volume of 25 L, and include preferably 1 μL of a mixture of the first primer set or the second primer set or the third primer set, 3 μL of an enzyme mixture Pxp-1st-mix, 1 μL of the template, and nuclease-free water as a balance. In the mixture of each pool primer set, 26 μL of Tris-HCl and 124 μL of primer set are preferably used to form a pool 1 primer with a total volume of 150 μL and a final concentration of 200 nM; except that the primers GATA1_001, KLF1_004, KLF1_008, and LU_004 are all 2 μL, and the primer Rh_020 is 5 μL, the other primers are all 1 μL. 32 μL of Tris-HCl and 168 μL of primer set are used to form a pool 2 primer with a total volume of 200 μL and a final concentration of 150 nM; except that the primer A4GALT_007 is 6 μL, the primers ABCG2_019, ABCG2_023, FUT_007, KLF1_005, KLF1_007, LU_001, LU_005, LU_008, MNS_002, and Rh_018 are 2 μL, the primer YT_002 is 3 μL, and the primer Rh_010 is 11 μL, the other primers are all 1 μL. 8 μL of Tris-HCl and 142 μL of primer set are used to form a pool 3 primer with a total volume of 150 μL and a final concentration of 200 nM; except that the primers A4GALT_005, ABCG2_006, ABCG2_024, KLF1_003, KLF1_006, LU_007, MNS_001, Rh_011, Rh_013, and SLC35C1_003 are 2 μL, the primer Rh_021 is 5 μL, the other primers are all 1 μL. When constructing each pool primer solution, each primer in each pool primer set has a concentration of 30 μM.

In the present disclosure, the three capture and amplification systems are preferably subjected to first amplification to obtain three first amplification products (pre-library products). Preferably, a PCR reaction program of the first amplification includes: initial denaturation at 98° C. for 20 min; 9 cycles of denaturation at 98° C. for 15 s, annealing at 62° C. for 20 min, extension at 68° C. for 60 s, and extension at 72° C. for 60 s; extension at 72° C. for 5 min; and heat preservation at 10° C.

In the present disclosure, the three first amplification products are purified separately, and three resulting purified pre-library products are subjected to second amplification with a sequencing universal adapter carrying an index separately to obtain three second amplification products (library construction products). The purification preferably includes purifying the PCR amplification products (pre-library products) of each sample using purification magnetic beads, removing the remaining primers, gDNA, and dNTPs in the PCR products and recovering the amplification products.

In the present disclosure, after the purification is completed, sequencing universal adapters (N5XX and A7XX) carrying an index are used to further PCR-amplify the purified products. A reaction system of the PCR amplification is calculated as 12.5 μL, and preferably includes: enzyme mixture Pxp-2nd-mix 6.5 μL; pre-library product 4 μL; universal adapter N5XX 1 μL, universal adapter A7XX 1 μL, with a total volume of 12.5 μL. The same sample includes 3 pre-library products, which are added to 3 tubes of PCR master mix containing the same universal adapter. The PCR reaction program is preferably: initial denaturation at 98° C. for 2 min; 23 cycles of denaturation at 98° C. for 15 s, extension at 68° C. for 60 s, and extension at 72° C. for 60 s; extension at 72° C. for 10 min; and heat preservation at 4° C.

In the present disclosure, after the PCR products are obtained, the library construction products of each sample are preferably separately purified using purification magnetic beads. The remaining primers and dNTPs are removed from the PCR product and the amplification products are recovered; the concentration and purity are measured, and the sample quality is tested by 1.5% agarose gel electrophoresis. After passing the test, the sample is diluted and mixed at equal concentrations, and then sequenced uniformly. The RBC blood group is determined based on sequencing results (Table 3). The mixed sample refers to mixing the products of the same sample amplified and purified in the first step using three sets of primers, and the purified products amplified in the second step using adapters carrying the same index. The sample mixing requirements: different samples are amplified in the second step using adapters carrying different indexes; 3 pools of the same sample are amplified in the second step using adapters with the same index.

TABLE 3

Polymorphisms of each gene

| Gene | Nucleotide change | Initiation site | Termination site | Gene | Nucleotide change | Initiation site | Termination site |
|---|---|---|---|---|---|---|---|
| RHD | c.1G | 25272548 | 25272548 | GYPB | 270 + 5T | 143997545 | 143997545 |
| RHD | c.3A | 25272550 | 25272550 | GYPB | 270 + 5A | 143997545 | 143997545 |
| RHD | c.8G | 25272555 | 25272555 | GYPB | c.251G | 143997559 | 143997559 |
| RHD | c.17T | 25272564 | 25272564 | GYPB | c.236G | 143997574 | 143997574 |
| RHD | c.19T | 25272566 | 25272566 | GYPB | c.230T | 143997580 | 143997580 |
| RHD | c.26A | 25272573 | 25272573 | GYPB | c.208T | 143997602 | 143997602 |
| RHD | c.28T | 25272575 | 25272575 | GYPB | c.173C | 143999413 | 143999413 |
| RHD | c.29A | 25272576 | 25272576 | GYPB | c.173G | 143999413 | 143999413 |
| RHD | c.29C | 25272576 | 25272576 | GYPB | c.161G | 143999425 | 143999425 |
| RHD | c.41G | 25272588 | 25272588 | GYPB | c.161A | 143999425 | 143999425 |
| RHD | c.41T | 25272588 | 25272588 | GYPB | c.143T | 143999443 | 143999443 |
| RHD | c.48C | 25272595 | 25272595 | GYPB | c.143C | 143999443 | 143999443 |
| RHD | c.52G | 25272599 | 25272599 | GYPB | c.72G | 144001249 | 144001249 |
| RHD | c.53C | 25272600 | 25272600 | GYPB | c.72T | 144001249 | 144001249 |
| RHD | c.62C | 25272609 | 25272609 | GYPB | c.71A | 144001250 | 144001250 |
| RHD | c.65A | 25272612 | 25272612 | GYPB | c.71G | 144001250 | 144001250 |
| RHD | c.67C | 25272614 | 25272614 | GYPB | c.67A | 144001254 | 144001254 |
| RHD | c.67T | 25272614 | 25272614 | GYPB | c.67T | 144001254 | 144001254 |
| RHD | c.68A | 25272615 | 25272615 | GYPB | c.65C | 144001256 | 144001256 |
| RHD | c.73T | 25272620 | 25272620 | GYPB | c.65G | 144001256 | 144001256 |
| RHD | c.91A | 25272638 | 25272638 | GYPB | c.60A | 144001261 | 144001261 |
| RHD | c.92C | 25272639 | 25272639 | GYPB | c.60G | 144001261 | 144001261 |
| RHD | c.93_94insT | 25272640 | 25272641 | GYPB | c.59T | 144001262 | 144001262 |
| RHD | c.120A | 25272667 | 25272667 | GYPB | c.59G | 144001262 | 144001262 |
| RHD | c.130_132delCTC | 25272677 | 25272679 | FUT3 | c.1067A | 5843773 | 5843773 |
| | | | | FUT3 | c.1060G | 5843780 | 5843780 |
| RHD | c.147del | 25272694 | 25272694 | FUT3 | c.1029G | 5843811 | 5843811 |
| RHD | 148 + 1a | 25272696 | 25272696 | FUT3 | c.980A | 5843860 | 5843860 |
| RHD | 148 + 5c | 25272700 | 25272700 | FUT3 | c.975A | 5843865 | 5843865 |
| RHD | c.150C | 25284574 | 25284574 | FUT3 | c.974T | 5843866 | 5843866 |
| RHD | c.157T | 25284581 | 25284581 | FUT3 | c.968C | 5843872 | 5843872 |
| RHD | c.161C | 25284585 | 25284585 | FUT3 | c.962A | 5843878 | 5843878 |
| RHD | c.163C | 25284587 | 25284587 | FUT3 | c.882T | 5843958 | 5843958 |
| RHD | c.173T | 25284597 | 25284597 | FUT3 | c.858G | 5843982 | 5843982 |
| RHD | c.176A | 25284600 | 25284600 | FUT3 | c.808G | 5844032 | 5844032 |
| RHD | c.178C | 25284602 | 25284602 | FUT3 | c.808A | 5844032 | 5844032 |
| RHD | c.182C | 25284606 | 25284606 | FUT3 | c.760A | 5844080 | 5844080 |
| RHD | c.182T | 25284606 | 25284606 | FUT3 | c.735C | 5844105 | 5844105 |
| RHD | c.186G | 25284610 | 25284610 | FUT3 | c.732T | 5844108 | 5844108 |
| RHD | c.186T | 25284610 | 25284610 | FUT3 | c.667A | 5844173 | 5844173 |
| RHD | c.200G | 25284624 | 25284624 | FUT3 | c.655A | 5844185 | 5844185 |
| RHD | c.201A | 25284625 | 25284625 | FUT3 | c.612G | 5844228 | 5844228 |
| RHD | c.203A | 25284627 | 25284627 | FUT3 | c.571A | 5844269 | 5844269 |
| RHD | c.203C | 25284627 | 25284627 | FUT3 | c.560T | 5844280 | 5844280 |
| RHD | c.208T | 25284632 | 25284632 | FUT3 | c.548T | 5844292 | 5844292 |
| RHD | c.209A | 25284633 | 25284633 | FUT3 | c.522A | 5844318 | 5844318 |
| RHD | c.220G | 25284644 | 25284644 | FUT3 | c.508A | 5844332 | 5844332 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| RHD | c.223T | 25284647 | 25284647 | FUT3 | c.484G | 5844356 | 5844356 |
| RHD | c.227A | 25284651 | 25284651 | FUT3 | c.484A | 5844356 | 5844356 |
| RHD | c.242C | 25284666 | 25284666 | FUT3 | c.478T | 5844362 | 5844362 |
| RHD | c.251C | 25284675 | 25284675 | FUT3 | c.451G | 5844389 | 5844389 |
| RHD | c.254G | 25284678 | 25284678 | FUT3 | c.370G | 5844470 | 5844470 |
| RHD | c.254T | 25284678 | 25284678 | FUT3 | c.314T | 5844526 | 5844526 |
| RHD | c.260A | 25284684 | 25284684 | FUT3 | c.304A | 5844536 | 5844536 |
| RHD | c.287A | 25284711 | 25284711 | FUT3 | c.258T | 5844582 | 5844582 |
| RHD | c.301A | 25284725 | 25284725 | FUT3 | c.202C | 5844638 | 5844638 |
| RHD | c.307C | 25284731 | 25284731 | FUT3 | c.179G | 5844661 | 5844661 |
| RHD | c.329C | 25284753 | 25284753 | FUT3 | c.179A | 5844661 | 5844661 |
| RHD | c.329T | 25284753 | 25284753 | FUT3 | c.104A | 5844736 | 5844736 |
| RHD | 336 − 2del | 25290639 | 25290639 | FUT3 | c.61T | 5844779 | 5844779 |
| RHD | c.340G | 25290645 | 25290645 | FUT3 | c.59G | 5844781 | 5844781 |
| RHD | c.340T | 25290645 | 25290645 | FUT3 | c.55A | 5844785 | 5844785 |
| RHD | c.341A | 25290646 | 25290646 | FUT3 | c.47C | 5844793 | 5844793 |
| RHD | c.346A | 25290651 | 25290651 | FUT3 | c.41A | 5844799 | 5844799 |
| RHD | c.346C | 25290651 | 25290651 | FUT3 | c.13G | 5844827 | 5844827 |
| RHD | c.347T | 25290652 | 25290652 | FUT3 | c.13A | 5844827 | 5844827 |
| RHD | c.359A | 25290664 | 25290664 | FUT6 | c.1002C | 5831566 | 5831566 |
| RHD | c.365T | 25290670 | 25290670 | FUT6 | c.1002G | 5831566 | 5831566 |
| RHD | c.374A | 25290679 | 25290679 | FUT6 | c.977G | 5831591 | 5831591 |
| RHD | c.376C | 25290681 | 25290681 | FUT6 | c.977A | 5831591 | 5831591 |
| RHD | c.379T | 25290684 | 25290684 | FUT6 | c.971C | 5831597 | 5831597 |
| RHD | c.394A | 25290699 | 25290699 | FUT6 | c.971T | 5831597 | 5831597 |
| RHD | c.395A | 25290700 | 25290700 | FUT6 | c.945C | 5831623 | 5831623 |
| RHD | c.399T | 25290704 | 25290704 | FUT6 | c.945A | 5831623 | 5831623 |
| RHD | c.410A | 25290715 | 25290715 | FUT6 | c.907C | 5831661 | 5831661 |
| RHD | c.410C | 25290715 | 25290715 | FUT6 | c.907G | 5831661 | 5831661 |
| RHD | c.410T | 25290715 | 25290715 | FUT6 | c.879C | 5831689 | 5831689 |
| RHD | c.413G | 25290718 | 25290718 | FUT6 | c.879T | 5831689 | 5831689 |
| RHD | c.446A | 25290751 | 25290751 | FUT6 | c.855G | 5831713 | 5831713 |
| RHD | c.455A | 25290760 | 25290760 | FUT6 | c.855A | 5831713 | 5831713 |
| RHD | c.455C | 25290760 | 25290760 | FUT6 | c.739G | 5831829 | 5831829 |
| RHD | c.458C | 25290763 | 25290763 | FUT6 | c.739A | 5831829 | 5831829 |
| RHD | c.485G | 25290790 | 25290790 | FUT6 | c.738C | 5831830 | 5831830 |
| RHD | 486 + 1a | 25290792 | 25290792 | FUT6 | c.738T | 5831830 | 5831830 |
| RHD | 486 + 2a | 25290793 | 25290793 | FUT6 | c.730C | 5831838 | 5831838 |
| RHD | c.490A | 25300949 | 25300949 | FUT6 | c.730G | 5831838 | 5831838 |
| RHD | c.492A | 25300951 | 25300951 | FUT6 | c.729T | 5831839 | 5831839 |
| RHD | c.494G | 25300953 | 25300953 | FUT6 | c.729C | 5831839 | 5831839 |
| RHD | c.497C | 25300956 | 25300956 | FUT6 | c.527G | 5832041 | 5832041 |
| RHD | c.505C | 25300964 | 25300964 | FUT6 | c.527T | 5832041 | 5832041 |
| RHD | c.509C | 25300968 | 25300968 | FUT6 | c.499_501insC | 5832067 | 5832069 |
| RHD | c.509G | 25300968 | 25300968 | FUT6 | c.376C | 5832192 | 5832192 |
| RHD | c.510A | 25300969 | 25300969 | FUT6 | c.376T | 5832192 | 5832192 |
| RHD | c.510T | 25300969 | 25300969 | FUT6 | c.370C | 5832198 | 5832198 |
| RHD | c.513A | 25300972 | 25300972 | FUT6 | c.370T | 5832198 | 5832198 |
| RHD | c.514T | 25300973 | 25300973 | FUT6 | c.336C | 5832232 | 5832232 |
| RHD | c.520A | 25300979 | 25300979 | FUT6 | c.336A | 5832232 | 5832232 |
| RHD | c.525A | 25300984 | 25300984 | FUT6 | c.172G | 5832396 | 5832396 |
| RHD | c.535C | 25300994 | 25300994 | FUT6 | c.172A | 5832396 | 5832396 |
| RHD | c.539A | 25300998 | 25300998 | FUT6 | c.63G | 5832505 | 5832505 |
| RHD | c.539C | 25300998 | 25300998 | FUT6 | c.63A | 5832505 | 5832505 |
| RHD | c.542C | 25301001 | 25301001 | FUT6 | c.18G | 5832550 | 5832550 |
| RHD | c.544A | 25301003 | 25301003 | FUT6 | c.18A | 5832550 | 5832550 |
| RHD | c.560C | 25301019 | 25301019 | FUT7 | c.329G | 137031410 | 137031410 |
| RHD | c.579C | 25301038 | 25301038 | FUT7 | c.329A | 137031410 | 137031410 |
| RHD | c.594T | 25301053 | 25301053 | KEL | c.2107A | 142941344 | 142941344 |
| RHD | c.602G | 25301061 | 25301061 | KEL | c.2030G | 142942441 | 142942441 |
| RHD | c.605T | 25301064 | 2530106 | KEL | c.2027A | 142942444 | 142942444 |
| RHD | c.607G | 25301066 | 25301066 | KEL | c.2024G | 142942447 | 142942447 |
| RHD | c.611C | 25301070 | 25301070 | KEL | c.2024A | 142942447 | 142942447 |
| RHD | c.621C | 25301080 | 25301080 | KEL | c.2023T | 142942448 | 142942448 |
| RHD | c.634A | 25301093 | 25301093 | KEL | c.1975del | 142942496 | 142942496 |
| RHD | c.634C | 25301093 | 25301093 | KEL | c.1947G | 142942524 | 142942524 |
| RHD | c.634T | 25301093 | 25301093 | KEL | c.1868G | 142942948 | 142942948 |
| RHD | 634 + 5t | 25301098 | 25301098 | KEL | c.1868A | 142942948 | 142942948 |
| RHD | 635 − 2c | 25301518 | 25301518 | KEL | c.1790C | 142943026 | 142943026 |
| RHD | 635 − 2g | 25301518 | 25301518 | KEL | c.1790T | 142943026 | 142943026 |
| RHD | c.635A | 25301520 | 25301520 | KEL | c.1763G | 142943284 | 142943284 |
| RHD | c.640T | 25301525 | 25301525 | KEL | c.1757G | 142943290 | 142943290 |
| RHD | c.658C | 25301543 | 25301543 | KEL | c.1719T | 142943328 | 142943328 |
| RHD | c.661A | 25301546 | 25301546 | KEL | c.1678G | 142943511 | 142943511 |
| RHD | c.661T | 25301546 | 25301546 | KEL | c.1664A | 142943525 | 142943525 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| RHD | c.667G | 25301552 | 25301552 | KEL | c.1643A | 142943546 | 142943546 |
| RHD | c.668C | 25301553 | 25301553 | KEL | c.1643G | 142943546 | 142943546 |
| RHD | c.671G | 25301556 | 25301556 | KEL | c.1596A | 142943593 | 142943593 |
| RHD | c.674T | 25301559 | 25301559 | KEL | c.1546T | 142943829 | 142943829 |
| RHD | c.676C | 25301561 | 25301561 | KEL | c.1490T | 142944324 | 142944324 |
| RHD | c.677A | 25301562 | 25301562 | KEL | c.1481T | 142944333 | 142944333 |
| RHD | c.680C | 25301565 | 25301565 | KEL | c.1481A | 142944333 | 142944333 |
| RHD | c.684_686del | 25301569 | 25301571 | KEL | c.1477T | 142944337 | 142944337 |
| RHD | c.686A | 25301571 | 25301571 | KEL | c.1475G | 142944339 | 142944339 |
| RHD | c.689T | 25301574 | 25301574 | KEL | c.1475A | 142944339 | 142944339 |
| RHD | c.697A | 25301582 | 25301582 | KEL | c.1420T | 142944394 | 142944394 |
| RHD | c.697C | 25301582 | 25301582 | KEL | c.1391C | 142944665 | 142944665 |
| RHD | c.700T | 25301585 | 25301585 | KEL | c.1391T | 142944665 | 142944665 |
| RHD | c.704C | 25301589 | 25301589 | KEL | c.1377A | 142944679 | 142944679 |
| RHD | c.705_707del | 25301590 | 25301592 | KEL | c.1298T | 142946223 | 142946223 |
| RHD | c.712A | 25301597 | 25301597 | KEL | c.1283G | 142946238 | 142946238 |
| RHD | c.722T | 25301607 | 25301607 | KEL | c.1283T | 142946238 | 142946238 |
| RHD | c.727A | 25301612 | 25301612 | KEL | c.1271C | 142946250 | 142946250 |
| RHD | c.728G | 25301613 | 25301613 | KEL | c.1271T | 142946250 | 142946250 |
| RHD | c.730C | 25301615 | 25301615 | KEL | c.1268T | 142946253 | 142946253 |
| RHD | c.731T | 25301616 | 25301616 | KEL | c.1217G | 142946304 | 142946304 |
| RHD | c.733C | 25301618 | 25301618 | KEL | c.1217A | 142946304 | 142946304 |
| RHD | c.739C | 25301624 | 25301624 | KEL | c.1216T | 142946305 | 142946305 |
| RHD | c.740G | 25301625 | 25301625 | KEL | c.1145G | 142952567 | 142952567 |
| RHD | c.744T | 25301629 | 25301629 | KEL | c.1145A | 142952567 | 142952567 |
| RHD | c.751C | 25301636 | 25301636 | KEL | c.1088A | 142952624 | 142952624 |
| RHD | c.758A | 25301643 | 25301643 | KEL | c.1042T | 142953839 | 142953839 |
| RHD | c.766C | 25301651 | 25301651 | KEL | c.986T | 142953895 | 142953895 |
| RHD | c.770T | 25301655 | 25301655 | KEL | c.986C | 142953895 | 142953895 |
| RHD | c.780A | 25301665 | 25301665 | KEL | c.965C | 142953916 | 142953916 |
| RHD | c.785del | 25301670 | 25301670 | KEL | c.965T | 142953916 | 142953916 |
| RHD | c.787A | 25301672 | 25301672 | KEL | c.948A | 142953933 | 142953933 |
| RHD | c.809A | 25303329 | 25303329 | KEL | 924 + 1a | 142954184 | 142954184 |
| RHD | c.809G | 25303329 | 25303329 | KEL | 924 + 1t | 142954184 | 142954184 |
| RHD | c.818A | 25303338 | 25303338 | KEL | c.913G | 142954195 | 142954195 |
| RHD | c.818T | 25303338 | 25303338 | KEL | c.913A | 142954195 | 142954195 |
| RHD | c.819A | 25303339 | 25303339 | KEL | c.905T | 142954203 | 142954203 |
| RHD | c.826C | 25303346 | 25303346 | KEL | c.905C | 142954203 | 142954203 |
| RHD | c.830A | 25303350 | 25303350 | KEL | c.903del | 142954205 | 142954205 |
| RHD | c.833A | 25303353 | 25303353 | KEL | c.877C | 142954231 | 142954231 |
| RHD | c.835A | 25303355 | 25303355 | KEL | c.877T | 142954231 | 142954231 |
| RHD | c.838A | 25303358 | 25303358 | KEL | c.875A | 142954233 | 142954233 |
| RHD | c.842G | 25303362 | 25303362 | KEL | c.875G | 142954233 | 142954233 |
| RHD | c.845A | 25303365 | 25303365 | KEL | c.842A | 142954266 | 142954266 |
| RHD | c.848T | 25303368 | 25303368 | KEL | c.841T | 142954267 | 142954267 |
| RHD | c.851T | 25303371 | 25303371 | KEL | c.841C | 142954267 | 142954267 |
| RHD | c.854A | 25303374 | 25303374 | KEL | c.787A | 142954321 | 142954321 |
| RHD | c.871T | 25303391 | 25303391 | KEL | c.780G | 142954328 | 142954328 |
| RHD | c.872G | 25303392 | 25303392 | KEL | c.780T | 142954328 | 142954328 |
| RHD | c.874C | 25303394 | 25303394 | KEL | c.758A | 142954350 | 142954350 |
| RHD | c.880C | 25303400 | 25303400 | KEL | c.758G | 142954350 | 142954350 |
| RHD | c.881T | 25303401 | 25303401 | KEL | c.745G | 142954363 | 142954363 |
| RHD | c.884A | 25303404 | 25303404 | KEL | c.745A | 142954363 | 142954363 |
| RHD | c.884C | 25303404 | 25303404 | KEL | c.743A | 142954365 | 142954365 |
| RHD | c.885T | 25303405 | 25303405 | KEL | c.743G | 142954365 | 142954365 |
| RHD | c.895G | 25303415 | 25303415 | KEL | c.742C | 142954366 | 142954366 |
| RHD | c.916A | 25303436 | 25303436 | KEL | c.742T | 142954366 | 142954366 |
| RHD | c.919A | 25303439 | 25303439 | KEL | 736 − 1c | 142954371 | 142954371 |
| RHD | c.922T | 25303442 | 25303442 | KEL | c.730del | 142954470 | 142954470 |
| RHD | c.932G | 25303452 | 25303452 | KEL | c.715T | 142954485 | 142954485 |
| RHD | c.938T | 25303458 | 25303458 | KEL | c.578T | 142957921 | 142957921 |
| RHD | c.953A | 25306609 | 25306609 | KEL | c.578C | 142957921 | 142957921 |
| RHD | c.957A | 25306613 | 25306613 | KEL | c.578G | 142957921 | 142957921 |
| RHD | c.968T | 25306624 | 25306624 | KEL | c.574T | 142957925 | 142957925 |
| RHD | c.983A | 25306639 | 25306639 | KEL | c.539G | 142957960 | 142957960 |
| RHD | c.993delC | 25306649 | 25306649 | KEL | c.539A | 142957960 | 142957960 |
| RHD | c.993G | 25306649 | 25306649 | KEL | c.539C | 142957960 | 142957960 |
| RHD | c.998A | 25306654 | 25306654 | KEL | c.538T | 142957961 | 142957961 |
| RHD | c.1006C | 25306662 | 25306662 | KEL | 526 − 2g | 142957975 | 142957975 |
| RHD | c.1012G | 25306668 | 25306668 | KEL | c.389G | 142960939 | 142960939 |
| RHD | c.1013C | 25306669 | 25306669 | KEL | c.389A | 142960939 | 142960939 |
| RHD | c.1015A | 25306671 | 25306671 | KEL | c.388C | 142960940 | 142960940 |
| RHD | c.1016A | 25306672 | 25306672 | KEL | c.388T | 142960940 | 142960940 |
| RHD | c.1018A | 25306674 | 25306674 | KEL | c.382T | 142960946 | 142960946 |
| RHD | c.1019T | 25306675 | 25306675 | KEL | c.306A | 142961022 | 142961022 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| RHD | c.1025C | 25306681 | 25306681 | KEL | c.246A | 142961082 | 142961082 |
| RHD | c.1034A | 25306690 | 25306690 | KEL | c.230T | 142961098 | 142961098 |
| RHD | c.1048C | 25306704 | 25306704 | KEL | 223 + 1a | 142961359 | 142961359 |
| RHD | c.1048G | 25306704 | 25306704 | KEL | c.184_185insT | 142961398 | 142961399 |
| RHD | c.1057A | 25306713 | 25306713 | A4GALT | c.631G | 42693321 | 42693321 |
| RHD | c.1059G | 25306715 | 25306715 | A4GALT | c.631C | 42693321 | 42693321 |
| RHD | c.1060A | 25306716 | 25306716 | A4GALT | c.241_243del | 42693709 | 42693711 |
| RHD | c.1061A | 25306717 | 25306717 | A4GALT | c.903G | 42693049 | 42693049 |
| RHD | c.1063A | 25306719 | 25306719 | A4GALT | c.903C | 42693049 | 42693049 |
| RHD | c.1070A | 25306726 | 25306726 | A4GALT | c.287A | 42693665 | 42693665 |
| RHD | c.1073C | 25306729 | 25306729 | A4GALT | c.299T | 42693653 | 42693653 |
| RHD | c.1107C | 25317033 | 25317033 | A4GALT | c.301del | 42693651 | 42693651 |
| RHD | c.1121A | 25317047 | 25317047 | A4GALT | c.418_428delins | 42693524 | 42693534 |
| RHD | c.1132G | 25317058 | 25317058 | A4GALT | c.470_496delins | 42693456 | 42693482 |
| RHD | c.1136T | 25317062 | 25317062 | A4GALT | c.473A | 42693479 | 42693479 |
| RHD | c.1145C | 25317071 | 25317071 | A4GALT | c.504dupC | 42693447 | 42693449 |
| RHD | c.1148C | 25317074 | 25317074 | A4GALT | c.914T | 42693038 | 42693038 |
| RHD | c.1152C | 25317078 | 25317078 | A4GALT | c.548A | 42693404 | 42693404 |
| RHD | 1154 − 8a | 25321881 | 25321881 | A4GALT | c.987G | 42692965 | 42692965 |
| RHD | c.1154C | 25321889 | 25321889 | A4GALT | c.987A | 42692965 | 42692965 |
| RHD | c.1168G | 25321903 | 25321903 | A4GALT | c.559C | 42693393 | 42693393 |
| RHD | c.1169C | 25321904 | 25321904 | A4GALT | c.560A | 42693392 | 42693392 |
| RHD | c.1170C | 25321905 | 25321905 | A4GALT | c.656T | 42693296 | 42693296 |
| RHD | c.1177C | 25321912 | 25321912 | A4GALT | c.657del | 42693295 | 42693295 |
| RHD | c.1184T | 25321919 | 25321919 | A4GALT | c.732dupG | 42693219 | 42693221 |
| RHD | c.1187G | 25321922 | 25321922 | A4GALT | c.751T | 42693201 | 42693201 |
| RHD | c.1193T | 25321928 | 25321928 | A4GALT | c.752T | 42693200 | 42693200 |
| RHD | c.1194C | 25321929 | 25321929 | A4GALT | c.796del | 42693156 | 42693156 |
| RHD | c.1195A | 25321930 | 25321930 | A4GALT | c.783A | 42693169 | 42693169 |
| RHD | c.1199C | 25321934 | 25321934 | A4GALT | c.972_997del | 42692955 | 42692980 |
| RHD | c.1199T | 25321934 | 25321934 | A4GALT | c.1029dupC | 42692922 | 42692924 |
| RHD | c.1200T | 25321935 | 25321935 | A4GALT | c.201dupC | 42693750 | 42693752 |
| RHD | c.1203A | 25321938 | 25321938 | A4GALT | c.418T | 42693534 | 42693534 |
| RHD | c.1207T | 25321942 | 25321942 | A4GALT | c.498A | 42693454 | 42693454 |
| RHD | c.1208T | 25321943 | 25321943 | A4GALT | c.68dupT | 42693883 | 42693885 |
| RHD | c.1210C | 25321945 | 25321945 | A4GALT | c.290T | 42693662 | 42693662 |
| RHD | c.1212A | 25321947 | 25321947 | A4GALT | c.902del | 42693050 | 42693050 |
| RHD | c.1213G | 25321948 | 25321948 | A4GALT | c.388dupA | 42693563 | 42693565 |
| RHD | c.1215C | 25321950 | 25321950 | A4GALT | c.367C | 42693585 | 42693585 |
| RHD | c.1219_1224del | 25321954 | 25321959 | A4GALT | c.547_548del | 42693404 | 42693405 |
| RHD | c.1221A | 25321956 | 25321956 | A4GALT | c.480_495dupGGCCGTGCAGGGGCGC | 42693457 | 42693472 |
| RHD | c.1222C | 25321957 | 25321957 | | | | |
| RHD | c.1224C | 25321959 | 25321959 | A4GALT | Exon 1 Deletion | 42720797 | 42720870 |
| RHD | c.1226T | 25321961 | 25321961 | B3GALNT1 | c.376G | 161086379 | 161086379 |
| RHD | c.1227A | 25321962 | 25321962 | B3GALNT1 | c.376A | 161086379 | 161086379 |
| RHD | c.1228G | 25328898 | 25328898 | B3GALNT1 | c.202T | 161086553 | 161086553 |
| RHD | c.1229C | 25328899 | 25328899 | B3GALNT1 | c.292_293insA | 161086462 | 161086463 |
| RHD | c.1238G | 25328908 | 25328908 | B3GALNT1 | c.433T | 161086322 | 161086322 |
| RHD | c.1241T | 25328911 | 25328911 | B3GALNT1 | c.537_538insA | 161086217 | 161086218 |
| RHD | c.1248_1249insG | 25328918 | 25328919 | B3GALNT1 | c.648C | 161086107 | 161086107 |
| | | | | B3GALNT1 | c.797C | 161085958 | 161085958 |
| RHD | c.1250C | 25328920 | 25328920 | B3GALNT1 | c.811A | 161085944 | 161085944 |
| RHD | c.1252_1253insT | 25328922 | 25328923 | B3GALNT1 | c.959A | 161085796 | 161085796 |
| | | | | B3GALNT1 | c.203del | 161086552 | 161086552 |
| RHD | c.1252A | 25328922 | 25328922 | B3GALNT1 | c.456G | 161086299 | 161086299 |
| RHCE | c.1254C | 25362427 | 25362427 | B3GALNT1 | c.449G | 161086306 | 161086306 |
| RHCE | 1228 − 2g | 25362455 | 25362455 | B3GALNT1 | c.598del | 161086157 | 161086157 |
| RHCE | c.1154C | 25362527 | 25362527 | LU | c.99_104del | 44811241 | 44811246 |
| RHCE | c.1132C | 25375370 | 25375370 | LU | c.123insGG | 44811265 | 44811267 |
| RHCE | c.1132G | 25375370 | 25375370 | LU | Exons 3 Deletion | 44812163 | 44812391 |
| RHCE | c.1130T | 25375372 | 25375372 | | | | |
| RHCE | c.1118T | 25375384 | 25375384 | LU | c.212G | 44812170 | 44812170 |
| RHCE | 1074 − 2g | 25375428 | 25375428 | LU | c.212A | 44812170 | 44812170 |
| RHCE | c.1044_1050dupGCTTCAT | 25385740 | 25385747 | LU | c.223C | 44812181 | 44812181 |
| | | | | LU | c.223T | 44812181 | 44812181 |
| RHCE | c.1025T | 25385759 | 25385759 | LU | c.230A | 44812188 | 44812188 |
| RHCE | c.1007A | 25385777 | 25385777 | LU | c.230G | 44812188 | 44812188 |
| RHCE | c.1007T | 25385777 | 25385777 | LU | c.282C | 44812240 | 44812240 |
| RHCE | c.1006G | 25385778 | 25385778 | LU | c.282G | 44812240 | 44812240 |
| RHCE | c.1006T | 25385778 | 25385778 | LU | c.326G | 44812284 | 44812284 |
| RHCE | c.966_968delinsC | 25385816 | 25385818 | LU | c.326A | 44812284 | 44812284 |
| | | | | LU | c.340G | 44812298 | 44812298 |
| RHCE | c.963del | 25385821 | 25385821 | LU | c.340A | 44812298 | 44812298 |
| RHCE | c.941C | 25385843 | 25385843 | LU | c.361T | 44812319 | 44812319 |
| RHCE | c.938delC | 25388977 | 25388977 | LU | c.419A | 44812377 | 44812377 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| RHCE | c.919A | 25388996 | 25388996 | LU | Exons 4 Deletion | 44812478 | 44812548 |
| RHCE | c.916G | 25388999 | 25388999 | | | | |
| RHCE | c.908A | 25389007 | 25389007 | LU | c.469G | 44812513 | 44812513 |
| RHCE | c.907del | 25389008 | 25389008 | LU | c.469A | 44812513 | 44812513 |
| RHCE | c.890C | 25389025 | 25389025 | LU | c.524G | 44813269 | 44813269 |
| RHCE | c.872T | 25389043 | 25389043 | LU | c.524A | 44813269 | 44813269 |
| RHCE | c.827A | 25389088 | 25389088 | LU | c.524T | 44813269 | 44813269 |
| RHCE | c.818C | 25389097 | 25389097 | LU | c.611T | 44813544 | 44813544 |
| RHCE | c.818T | 25389097 | 25389097 | LU | c.611A | 44813544 | 44813544 |
| RHCE | c.807A | 25389108 | 25389108 | LU | c.662C | 44813595 | 44813595 |
| RHCE | 801 + 1a | 25390748 | 25390748 | LU | c.662T | 44813595 | 44813595 |
| RHCE | c.800A | 25390750 | 25390750 | LU | c.679C | 44813612 | 44813612 |
| RHCE | c.787G | 25390763 | 25390763 | LU | c.679T | 44813612 | 44813612 |
| RHCE | c.774A | 25390776 | 25390776 | LU | c.691T | 44813624 | 44813624 |
| RHCE | c.748A | 25390802 | 25390802 | LU | c.711C | 44813644 | 44813644 |
| RHCE | c.744C | 25390806 | 25390806 | LU | c.711T | 44813644 | 44813644 |
| RHCE | c.744T | 25390806 | 25390806 | LU | c.711A | 44813644 | 44813644 |
| RHCE | c.734C | 25390816 | 25390816 | LU | c.714C | 44813647 | 44813647 |
| RHCE | c.733C | 25390817 | 25390817 | LU | c.714T | 44813647 | 44813647 |
| RHCE | c.733G | 25390817 | 25390817 | LU | c.824C | 44814191 | 44814191 |
| RHCE | c.730A | 25390820 | 25390820 | LU | c.824T | 44814191 | 44814191 |
| RHCE | c.728G | 25390822 | 25390822 | LU | c.905C | 44814272 | 44814272 |
| RHCE | c.722T | 25390828 | 25390828 | LU | c.905T | 44814272 | 44814272 |
| RHCE | c.712A | 25390838 | 25390838 | LU | c.1274A | 44818820 | 44818820 |
| RHCE | c.712G | 25390838 | 25390838 | LU | c.1274C | 44818820 | 44818820 |
| RHCE | c.697C | 25390853 | 25390853 | LU | c.1289C | 44818835 | 44818835 |
| RHCE | c.697G | 25390853 | 25390853 | LU | c.1289T | 44818835 | 44818835 |
| RHCE | c.695C | 25390855 | 25390855 | LU | c.1340C | 44819059 | 44819059 |
| RHCE | c.689C | 25390861 | 25390861 | LU | c.1340T | 44819059 | 44819059 |
| RHCE | c.685_687del | 25390863 | 25390865 | LU | c.1495C | 44819367 | 44819367 |
| RHCE | c.679_683del | 25390867 | 25390871 | LU | c.1495T | 44819367 | 44819367 |
| RHCE | c.676C | 25390874 | 25390874 | LU | c.1615A | 44819487 | 44819487 |
| RHCE | c.676del | 25390874 | 25390874 | LU | c.1615G | 44819487 | 44819487 |
| RHCE | c.676G | 25390874 | 25390874 | LU | c.1742A | 44819705 | 44819705 |
| RHCE | c.674G | 25390876 | 25390876 | LU | c.1742T | 44819705 | 44819705 |
| RHCE | c.667T | 25390883 | 25390883 | KLF1 | c.1071A | 12884903 | 12884903 |
| RHCE | c.662C | 25390888 | 25390888 | KLF1 | c.1048T | 12884926 | 12884926 |
| RHCE | c.662G | 25390888 | 25390888 | KLF1 | c.1045del | 12884929 | 12884929 |
| RHCE | c.659A | 25390891 | 25390891 | KLF1 | c.1040A | 12884934 | 12884934 |
| RHCE | c.649C | 25390901 | 25390901 | KLF1 | c.1022A | 12884952 | 12884952 |
| RHCE | 634 + 1t | 25391993 | 25391993 | KLF1 | c.1004C | 12884970 | 12884970 |
| RHCE | c.602C | 25392026 | 25392026 | KLF1 | c.1002del | 12884972 | 12884972 |
| RHCE | c.554A | 25392074 | 25392074 | KLF1 | c.1001T | 12884973 | 12884973 |
| RHCE | c.538C | 25392090 | 25392090 | KLF1 | c.994G | 12884980 | 12884980 |
| RHCE | c.527T | 25392101 | 25392101 | KLF1 | c.991G | 12884983 | 12884983 |
| RHCE | c.526A | 25392102 | 25392102 | KLF1 | c.991T | 12884983 | 12884983 |
| RHCE | c.520A | 25392108 | 25392108 | KLF1 | c.983T | 12884991 | 12884991 |
| RHCE | c.512G | 25392116 | 25392116 | KLF1 | c.983A | 12884991 | 12884991 |
| RHCE | c.506A | 25392122 | 25392122 | KLF1 | c.977C | 12884997 | 12884997 |
| RHCE | c.506C | 25392122 | 25392122 | KLF1 | c.973A | 12885001 | 12885001 |
| RHCE | c.501A | 25392127 | 25392127 | KLF1 | c.968G | 12885006 | 12885006 |
| RHCE | c.500A | 25392128 | 25392128 | KLF1 | c.954dupG | 12885019 | 12885021 |
| RHCE | c.500T | 25392128 | 25392128 | KLF1 | c.948del | 12885026 | 12885026 |
| RHCE | c.497T | 25392131 | 25392131 | KLF1 | c.947A | 12885027 | 12885027 |
| RHCE | c.494C | 25392134 | 25392134 | KLF1 | c.946A | 12885028 | 12885028 |
| RHCE | c.491G | 25392137 | 25392137 | KLF1 | c.939A | 12885035 | 12885035 |
| RHCE | 487 − 5g | 25392146 | 25392146 | KLF1 | 914 − 1c | 12885061 | 12885061 |
| RHCE | 486 + 5a | 25402591 | 25402591 | KLF1 | c.902ins T | 12885327 | 12885329 |
| RHCE | 486 + 1a | 25402595 | 25402595 | KLF1 | c.899C | 12885331 | 12885331 |
| RHCE | c.473A | 25402609 | 25402609 | KLF1 | c.895T | 12885335 | 12885335 |
| RHCE | c.464G | 25402618 | 25402618 | KLF1 | c.887C | 12885343 | 12885343 |
| RHCE | c.461C | 25402621 | 25402621 | KLF1 | c.874T | 12885356 | 12885356 |
| RHCE | 460G | 25402622 | 25402622 | KLF1 | c.868C | 12885362 | 12885362 |
| RHCE | c.455A | 25402627 | 25402627 | KLF1 | c.826G | 12885404 | 12885404 |
| RHCE | c.380T | 25402702 | 25402702 | KLF1 | c.826T | 12885404 | 12885404 |
| RHCE | c.377G | 25402705 | 25402705 | KLF1 | c.809A | 12885421 | 12885421 |
| RHCE | c.375G | 25402707 | 25402707 | KLF1 | c.802T | 12885428 | 12885428 |
| RHCE | c.374A | 25402708 | 25402708 | KLF1 | c.796T | 12885434 | 12885434 |
| RHCE | c.365C | 25402717 | 25402717 | KLF1 | c.663del | 12885567 | 12885567 |
| RHCE | c.365T | 25402717 | 25402717 | KLF1 | c.637T | 12885593 | 12885593 |
| RHCE | c.364C | 25402718 | 25402718 | KLF1 | c.621G | 12885609 | 12885609 |
| RHCE | c.361T | 25402721 | 25402721 | KLF1 | c.569del | 12885661 | 12885661 |
| RHCE | c.350_358del | 25402724 | 25402732 | KLF1 | c.551_556delinsA | 12885674 | 12885679 |
| RHCE | c.356A | 25402726 | 25402726 | | | | |
| RHCE | c.344C | 25402738 | 25402738 | KLF1 | c.533A | 12885697 | 12885697 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| RHCE | c.344G | 25402738 | 25402738 | KLF1 | c.519_525dupCGGCGCC | 12885699 | 12885716 |
| RHCE | c.341A | 25402741 | 25402741 | | | | |
| RHCE | c.340C | 25402742 | 25402742 | KLF1 | c.519_520insC | 12885709 | 12885712 |
| RHCE | c.340T | 25402742 | 25402742 | KLF1 | c.519G | 12885711 | 12885711 |
| RHCE | 335 + 3t | 25408680 | 25408680 | KLF1 | c.517del | 12885713 | 12885713 |
| RHCE | c.308T | 25408710 | 25408710 | KLF1 | c.472del | 12885758 | 12885758 |
| RHCE | c.307C | 25408711 | 25408711 | KLF1 | c.384insC | 12885845 | 12885847 |
| RHCE | c.307T | 25408711 | 25408711 | KLF1 | c.380A | 12885850 | 12885850 |
| RHCE | c.286A | 25408732 | 25408732 | KLF1 | c.310_311insG | 12885918 | 12885920 |
| RHCE | c.286G | 25408732 | 25408732 | KLF1 | c.262_284dup | 12885924 | 12885990 |
| RHCE | c.254C | 25408764 | 25408764 | KLF1 | c.304C | 12885926 | 12885926 |
| RHCE | c.254G | 25408764 | 25408764 | KLF1 | c.298T | 12885932 | 12885932 |
| RHCE | c.221A | 25408797 | 25408797 | KLF1 | c.204del | 12886026 | 12886026 |
| RHCE | c.208T | 25408810 | 25408810 | KLF1 | c.196T | 12886034 | 12886034 |
| RHCE | c.203G | 25408815 | 25408815 | KLF1 | c.151del | 12886079 | 12886079 |
| RHCE | c.202G | 25408816 | 25408816 | KLF1 | c.114del | 12886116 | 12886116 |
| RHCE | c.201G | 25408817 | 25408817 | KLF1 | c.109T | 12886121 | 12886121 |
| RHCE | c.187C | 25408831 | 25408831 | KLF1 | c.90A | 12886140 | 12886140 |
| RHCE | c.178A | 25408840 | 25408840 | KLF1 | c.86G | 12887055 | 12887055 |
| RHCE | c.150T | 25408868 | 25408868 | KLF1 | promoter | 12887479 | 12887479 |
| RHCE | 149 − 1a | 25408870 | 25408870 | GATA1 | c.1240C | 48794162 | 48794162 |
| RHCE | 148 + 5a | 25420634 | 25420634 | ACHE | c.1057C > A | 100893176 | 100893176 |
| RHCE | c.122A | 25420665 | 25420665 | ACHE | c.266G > A | 100893967 | 100893967 |
| RHCE | c.122G | 25420665 | 25420665 | ACHE | c.169G > A | 100894064 | 100894064 |
| RHCE | c.106A | 25420681 | 25420681 | ACHE | c.101G > A | 100894132 | 100894132 |
| RHCE | c.106G | 25420681 | 25420681 | ERMAP | c.169G > A | 42830851 | 42830851 |
| RHCE | c.105T | 25420682 | 25420682 | ERMAP | c.178C > G | 42830860 | 42830860 |
| RHCE | c.98C | 25420689 | 25420689 | ERMAP | c.139C > A | 42830821 | 42830821 |
| RHCE | c.93_94insT | 25420693 | 25420694 | ERMAP | c.242G > A | 42830924 | 42830924 |
| RHCE | c.94G | 25420693 | 25420693 | ERMAP | c.103G > A | 42830785 | 42830785 |
| RHCE | c.80_84del | 25420703 | 25420707 | ERMAP | c.307_308delGA | 42830989 | 42830990 |
| RHCE | c.84A | 25420703 | 25420703 | ERMAP | c.994C > T | 42829761 | 42829761 |
| RHCE | c.79_81del | 25420706 | 25420708 | ART4 | c.144 + 2T > C | 14842968 | 14842968 |
| RHCE | c.48C | 25420739 | 25420739 | ART4 | c.145 − 2A > G | 14841155 | 14841155 |
| RHCE | c.48G | 25420739 | 25420739 | ART4 | c.185T > C | 14841113 | 14841113 |
| RHCE | c.28T | 25420759 | 25420759 | ART4 | c.268C > T | 14841030 | 14841030 |
| RHCE | 1 − 10t | 25420796 | 25420796 | ART4 | c.323G > A | 14840975 | 14840975 |
| FUT1 | c.1047C | 48750235 | 48750235 | ART4 | c.343_350del | 14840948 | 14840955 |
| FUT1 | c.1047G | 48750235 | 48750235 | ART4 | c.350C > T | 14840948 | 14840948 |
| FUT1 | c.991A | 48750291 | 48750291 | ART4 | c.405C > A | 14840893 | 14840893 |
| FUT1 | c.990del | 48750292 | 48750292 | ART4 | c.431C > A | 14840867 | 14840867 |
| FUT1 | c.980A | 48750302 | 48750302 | ART4 | c.432C > A | 14840866 | 14840866 |
| FUT1 | c.980C | 48750302 | 48750302 | ART4 | c.442C > T | 14840856 | 14840856 |
| FUT1 | c.958A | 48750324 | 48750324 | ART4 | c.547T > G | 14840749 | 14840749 |
| FUT1 | c.948C | 48750334 | 48750334 | ART4 | c.566C > T | 14840732 | 14840732 |
| FUT1 | c.948G | 48750334 | 48750334 | ART4 | c.674T > A | 14843243 | 14843243 |
| FUT1 | c.944C | 48750338 | 48750338 | ART4 | c.793A > G | 14840505 | 14840505 |
| FUT1 | c.944T | 48750338 | 48750338 | ART4 | c.793A > G | 14840505 | 14840505 |
| FUT1 | c.917T | 48750365 | 48750365 | ART4 | c.793A > G | 14840505 | 14840505 |
| FUT1 | c.903_904insAAC | 48750379 | 48750380 | ART4 | c.793A > G | 14840505 | 14840505 |
| | | | | ART4 | c.793A > G | 14840505 | 14840505 |
| FUT1 | c.896C | 48750386 | 48750386 | AQP1 | del all or part exon 1 | 30911853 | 30912293 |
| FUT1 | c.881_882del | 48750400 | 48750401 | | | | |
| FUT1 | c.882T | 48750400 | 48750400 | AQP1 | c.112C > T | 30912021 | 30912021 |
| FUT1 | c.881T | 48750401 | 48750401 | AQP1 | c.113C > T | 30912022 | 30912022 |
| FUT1 | c.880T | 48750402 | 48750402 | AQP1 | c.134C > T | 30912043 | 30912043 |
| FUT1 | c.832A | 48750450 | 48750450 | AQP1 | c.140A > G | 30912049 | 30912049 |
| FUT1 | c.826C | 48750456 | 48750456 | AQP1 | c.232delG | 30912141 | 30912141 |
| FUT1 | c.826T | 48750456 | 48750456 | AQP1 | c.308_309insT | 30912217 | 30912218 |
| FUT1 | c.801C | 48750481 | 48750481 | AQP1 | c.576C > A | 30922590 | 30922590 |
| FUT1 | c.801T | 48750481 | 48750481 | AQP1 | c.601delG | 30922614 | 30922614 |
| FUT1 | c.786C | 48750496 | 48750496 | ICAM4 | c.299A > G | 10287311 | 10287311 |
| FUT1 | c.785A | 48750497 | 48750497 | ICAM4 | c.346_355del | 10287358 | 10287367 |
| FUT1 | c.785G | 48750497 | 48750497 | ABCG2 | c.2T > C | 88139994 | 88139994 |
| FUT1 | c.776A | 48750506 | 48750506 | ABCG2 | c.34G > A | 88139962 | 88139962 |
| FUT1 | c.776T | 48750506 | 48750506 | ABCG2 | c.34G > A | 88139962 | 88139962 |
| FUT1 | c.768del | 48750514 | 48750514 | ABCG2 | c.34G > A | 88139962 | 88139962 |
| FUT1 | c.748T | 48750534 | 48750534 | ABCG2 | 187_197delATATTATCGAA | 88139799 | 88139809 |
| FUT1 | c.725G | 48750557 | 48750557 | ABCG2 | c.244_245insC | 88132594 | 88132595 |
| FUT1 | c.725T | 48750557 | 48750557 | ABCG2 | c.263 + 1G > A | 88132575 | 88132575 |
| FUT1 | c.721C | 48750561 | 48750561 | ABCG2 | c.289A > T | 88131892 | 88131892 |
| FUT1 | c.695A | 48750587 | 48750587 | ABCG2 | c.337C > T | 88131844 | 88131844 |
| FUT1 | c.695G | 48750587 | 48750587 | ABCG2 | c.376C > T | 88131805 | 88131805 |
| FUT1 | c.694C | 48750588 | 48750588 | ABCG2 | c.420_421insA | 88131171 | 88131172 |
| FUT1 | c.694T | 48750588 | 48750588 | ABCG2 | c.421C > A | 88131171 | 88131171 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| FUT1 | c.689C | 48750593 | 48750593 | ABCG2 | c.421C > A | 88131171 | 88131171 |
| FUT1 | c.684A | 48750598 | 48750598 | ABCG2 | c.421C > A | 88131171 | 88131171 |
| FUT1 | c.684G | 48750598 | 48750598 | ABCG2 | c.421C > A | 88131171 | 88131171 |
| FUT1 | c.682G | 48750600 | 48750600 | ABCG2 | c.439C > T | 88131153 | 88131153 |
| FUT1 | c.661T | 48750621 | 48750621 | ABCG2 | c.440G > A | 88131152 | 88131152 |
| FUT1 | c.659A | 48750623 | 48750623 | ABCG2 | c.455T > C | 88131137 | 88131137 |
| FUT1 | c.658T | 48750624 | 48750624 | ABCG2 | c.458C > T | 88131134 | 88131134 |
| FUT1 | c.655C | 48750627 | 48750627 | ABCG2 | c.542_543insA | 88121782 | 88121782 |
| FUT1 | c.649T | 48750633 | 48750633 | ABCG2 | c.565_566del | 88121758 | 88121759 |
| FUT1 | c.586C | 48750696 | 48750696 | ABCG2 | c.706C > T | 88118244 | 88118244 |
| FUT1 | c.586T | 48750696 | 48750696 | ABCG2 | c.706C > T | 88118244 | 88118244 |
| FUT1 | c.551_552del | 48750730 | 48750731 | ABCG2 | c.730C > T | 88118220 | 88118220 |
| FUT1 | c.548G | 48750734 | 48750734 | ABCG2 | c.736C > T | 88118214 | 88118214 |
| FUT1 | c.547A | 48750735 | 48750735 | ABCG2 | c.784G > T | 88118166 | 88118166 |
| FUT1 | c.545A | 48750737 | 48750737 | ABCG2 | c.791_792delTT | 88118158 | 88118159 |
| FUT1 | c.538C | 48750744 | 48750744 | ABCG2 | c.875_878dupACTT | 88115022 | 88115025 |
| FUT1 | c.538T | 48750744 | 48750744 | ABCG2 | c.986_987delTA | 88113510 | 88113511 |
| FUT1 | c.522A | 48750760 | 48750760 | ABCG2 | c.1017_1019delCTC | 88113478 | 88113480 |
| FUT1 | c.513C | 48750769 | 48750769 | ABCG2 | c.1111_1112delAC | 88113385 | 88113386 |
| FUT1 | c.513G | 48750769 | 48750769 | ABCG2 | c.1384G > A | 88099432 | 88099432 |
| FUT1 | c.491A | 48750791 | 48750791 | ABCG2 | c.1515del | 88097585 | 88097585 |
| FUT1 | c.462A | 48750820 | 48750820 | ABCG2 | c.1515del | 88097585 | 88097585 |
| FUTI | c.462C | 48750820 | 48750820 | ABCG2 | c.1591C > T | 88097509 | 88097509 |
| FUTI | c.461A | 48750821 | 48750821 | ABCG2 | c.1714A > C | 88095543 | 88095543 |
| FUT1 | c.461G | 48750821 | 48750821 | ABCG2 | c.1723C > T | 88095534 | 88095534 |
| FUT1 | c.460C | 48750822 | 48750822 | ABCG2 | c.1789_1790insT | 88094607 | 88094608 |
| FUT1 | c.442T | 48750840 | 48750840 | ABCG2 | c.1819T > C | 88094578 | 88094578 |
| FUT1 | c.424T | 48750858 | 48750858 | ABCG2 | c.1819T > C | 88094578 | 88094578 |
| FUT1 | c.423A | 48750859 | 48750859 | ABCG2 | c.1820 + 1g > a | 88094576 | 88094576 |
| FUT1 | c.422A | 48750860 | 48750860 | ABCG2 | c.1841T > G | 88092361 | 88092361 |
| FUT1 | c.422G | 48750860 | 48750860 | ABCG2 | c.1858G > A | 88092344 | 88092344 |
| FUT1 | c.371G | 48750911 | 48750911 | ABCG2 | 27-kb deletion | 88165417 | 88165645 |
| FUT1 | c.349T | 48750933 | 48750933 | ABCG2 | 27-kb deletion | 88164336 | 88164501 |
| FUT1 | c.328A | 48750954 | 48750954 | ABCG2 | 27-kb deletion | 88164178 | 88164315 |
| FUT1 | c.293T | 48750989 | 48750989 | ABCG2 | 27-kb deletion | 88158437 | 88158666 |
| FUT1 | c.269T | 48751013 | 48751013 | ABCG2 | 27-kb deletion | 88158199 | 88158398 |
| FUT1 | c.235C | 48751047 | 48751047 | ABCG2 | 27-kb deletion | 88157873 | 88158062 |
| FUT1 | c.35T | 48751247 | 48751247 | ABCG2 | 27-kb deletion | 88156758 | 88156907 |
| FUT2 | c.4A | 48702960 | 48702960 | ABCG2 | 27-kb deletion | 88150594 | 88150739 |
| FUT2 | c.40G | 48702996 | 48702996 | ABCG2 | 27-kb deletion | 88145144 | 88145356 |
| FUT2 | c.113T | 48703069 | 48703069 | ABCG2 | 27-kb deletion | 88139952 | 88140181 |
| FUT2 | c.244A | 48703200 | 48703200 | FY | c.125G | 159205564 | 159205564 |
| FUT2 | c.244G | 48703200 | 48703200 | FY | c.265T | 159205704 | 159205704 |
| FUT2 | c.278T | 48703234 | 48703234 | FY | c.298A | 159205737 | 159205737 |
| FUT2 | c.302T | 48703258 | 48703258 | FY | c.680A | 159206119 | 159206119 |
| FUT2 | c.379T | 48703335 | 48703335 | FY | c.125A | 159205564 | 159205564 |
| FUT2 | c.385A | 48703341 | 48703341 | FY | c.145T | 159205584 | 159205584 |
| FUT2 | c.385T | 48703341 | 48703341 | FY | c.266A | 159205705 | 159205705 |
| FUT2 | c.400A | 48703356 | 48703356 | FY | c.901T | 159206340 | 159206340 |
| FUT2 | c.412A | 48703368 | 48703368 | FY | c.281_295del | 159205720 | 159205734 |
| FUT2 | c.428A | 48703384 | 48703384 | FY | c.408A | 159205847 | 159205847 |
| FUT2 | c.481A | 48703437 | 48703437 | FY | c.287A | 159205726 | 159205726 |
| FUT2 | c.569A | 48703525 | 48703525 | FY | c.327del | 159205766 | 159205766 |
| FUT2 | c.571T | 48703527 | 48703527 | FY | c.395A | 159205834 | 159205834 |
| FUT2 | c.628T | 48703584 | 48703584 | FY | c.719del | 159206158 | 159206158 |
| FUT2 | c.658T | 48703614 | 48703614 | FY | −69C | 159205371 | 159205371 |
| FUT2 | c.664T | 48703620 | 48703620 | FY | c.296 496delinsAGGCCACTG | 159205735 | 159205935 |
| FUT2 | c.665A | 48703621 | 48703621 | | | | |
| FUT2 | c.685_686del | 48703641 | 48703642 | FY | c.407A | 159205846 | 159205846 |
| FUT2 | c.685A | 48703641 | 48703641 | FY | c.781A | 159206220 | 159206220 |
| FUT2 | c.688_690del | 48703644 | 48703646 | FY | c.179_180del | 159205618 | 159205619 |
| FUT2 | c.716A | 48703672 | 48703672 | FY | c.895A | 159206334 | 159206334 |
| FUT2 | c.747_748insGTG | 48703703 | 48703704 | FY | c.151del | 159205590 | 159205590 |
| | | | | GYPA | c.250G | 114118735 | 114118735 |
| FUT2 | c.778del | 48703734 | 48703734 | GYPA | c.250C | 114118735 | 114118735 |
| FUT2 | c.818A | 48703774 | 48703774 | GYPA | c.244C | 114118741 | 114118741 |
| FUT2 | c.849A | 48703805 | 48703805 | GYPA | c.244A | 114118741 | 114118741 |
| FUT2 | c.853A | 48703809 | 48703809 | GYPA | c.242T | 114118743 | 114118743 |
| FUT2 | c.868A | 48703824 | 48703824 | GYPA | c.242G | 114118743 | 114118743 |
| FUT2 | c.950T | 48703906 | 48703906 | GYPA | c.240G | 114118745 | 114118745 |
| JK | c.130A | 45730450 | 45730450 | GYPA | c.240T | 114118745 | 114118745 |
| JK | c.838G | 45739554 | 45739554 | GYPA | c.239T | 114118746 | 114118746 |
| JK | c.511C | 45736496 | 45736496 | GYPA | c.239C | 114118746 | 114118746 |
| JK | c.28A | 45730348 | 45730348 | GYPA | c.232G | 144119686 | 144119686 |
| JK | c.226A | 45731089 | 45731089 | GYPA | c.232A | 144119686 | 144119686 |

TABLE 3-continued

Polymorphisms of each gene

| Gene | Nucleotide change | Initiation site | Termination site | Gene | Nucleotide change | Initiation site | Termination site |
|---|---|---|---|---|---|---|---|
| JK | c.742A | 45739241 | 45739241 | GYPA | GYP del exon 3 | 144119686 | 144119781 |
| JK | c.838A | 45739554 | 45739554 | GYPA | c.230C | 144119688 | 144119688 |
| JK | c.548T | 45736533 | 45736533 | GYPA | c.230T | 144119688 | 144119688 |
| JK | c.718A | 45739217 | 45739217 | GYPA | c.226G | 144119692 | 144119692 |
| JK | c.202T | 45731065 | 45731065 | GYPA | c.226A | 144119692 | 144119692 |
| JK | c.582G | 45736567 | 45736567 | GYPA | c.217C | 144119701 | 144119701 |
| JK | c.956T | 45748385 | 45748385 | GYPA | c.217T | 144119701 | 144119701 |
| JK | c.561A | 45736546 | 45736546 | GYPA | c.212C | 144119706 | 144119706 |
| JK | 342 − 1a | 45734273 | 45734273 | GYPA | c.203C | 144119715 | 144119715 |
| JK | c.723del | 45739222 | 45739222 | GYPA | c.197C | 144119721 | 144119721 |
| JK | c.866G | 45739582 | 45739582 | GYPA | c.197A | 144119721 | 144119721 |
| JK | c.27_50del | 45730347 | 45730370 | GYPA | c.191A | 144119727 | 144119727 |
| JK | 811 + 5A | 45739315 | 45739315 | GYPA | c.164_166del | 144119752 | 144119754 |
| JK | 342 − 1c | 45734273 | 45734273 | GYPA | c.160C | 144119758 | 144119758 |
| JK | c.222A | 45731085 | 45731085 | GYPA | c.148C | 144119770 | 144119770 |
| JK | c.499G | 45736484 | 45736484 | GYPA | c.148T | 144119770 | 144119770 |
| JK | 663 + 1t | 45736649 | 45736649 | GYPA | c.140T | 144119778 | 144119778 |
| JK | c.871C | 45739587 | 45739587 | GYPA | c.140A | 144119778 | 144119778 |
| JK | c.896A | 45739612 | 45739612 | GYPA | c.140C | 144119778 | 144119778 |
| JK | c.191A | 45731054 | 45731054 | GYPA | c.138T | 144119780 | 144119780 |
| JK | c.194A | 45731057 | 45731057 | GYPA | c.138A | 144119780 | 144119780 |
| JK | c.512A | 45736497 | 45736497 | GYPA | c.107C | 144120519 | 144120519 |
| JK | c.437C | 45734369 | 45734369 | GYPA | c.107A | 144120519 | 144120519 |
| JK | c.536G | 45736521 | 45736521 | GYPA | c.72T | 144120554 | 144120554 |
| DI | c.2561T | 44251253 | 44251253 | GYPA | c.72G | 144120554 | 144120554 |
| DI | c.2561C | 44251253 | 44251253 | GYPA | c.71G | 144120555 | 144120555 |
| DI | c.1972A | 44254581 | 44254581 | GYPA | c.71A | 144120555 | 144120555 |
| DI | c.1972G | 44254581 | 44254581 | GYPA | c.68A | 144120558 | 144120558 |
| DI | c.1669A | 44255804 | 44255804 | GYPA | c.68C | 144120558 | 144120558 |
| DI | c.1669G | 44255804 | 44255804 | GYPA | c.67T | 144120559 | 144120559 |
| DI | c.1643T | 44255830 | 44255830 | GYPA | c.59C | 144120567 | 144120567 |
| DI | c.1643C | 44255830 | 44255830 | GYPA | c.59T | 144120567 | 144120567 |
| DI | c.1654T | 44255819 | 44255819 | GYPA | c.58T | 144120568 | 144120568 |
| DI | c.1654A | 44255819 | 44255819 | SLC35C1 | c.439C | 45806240 | 45806240 |
| DI | c.1294T | 44257796 | 44257796 | SLC35C1 | c.588G | 45810828 | 45810828 |
| DI | c.1294C | 44257796 | 44257796 | SLC35C1 | c.923C | 45811163 | 45811163 |
| DI | c.1694C | 44255779 | 44255779 | SLC35C1 | c.439T | 45806240 | 45806240 |
| DI | c.1694G | 44255779 | 44255779 | SLC35C1 | c.923G | 45811163 | 45811163 |
| DI | c.1707A | 44255766 | 44255766 | SLC35C1 | c.588del | 45810828 | 45810828 |
| DI | c.1707C | 44255766 | 44255766 | | | | |
| DI | c.1967A | 44254586 | 44254586 | | | | |
| DI | c.1967G | 44254586 | 44254586 | | | | |
| DI | c.1966T | 44254587 | 44254587 | | | | |
| DI | c.1966C | 44254587 | 44254587 | | | | |
| DI | c.1663C | 44255810 | 44255810 | | | | |
| DI | c.1663T | 44255810 | 44255810 | | | | |
| DI | c.1937A | 44254616 | 44254616 | | | | |
| DI | c.1936T | 44254617 | 44254617 | | | | |
| DI | c.1936C | 44254617 | 44254617 | | | | |
| DI | c.1937G | 44254616 | 44254616 | | | | |
| DI | c.1681T | 44255792 | 44255792 | | | | |
| DI | c.1681C | 44255792 | 44255792 | | | | |
| DI | c.1287T | 44257803 | 44257803 | | | | |
| DI | c.1681G | 44255792 | 44255792 | | | | |
| DI | c.1287A | 44257803 | 44257803 | | | | |
| DI | c.1696T | 44255777 | 44255777 | | | | |
| DI | c.1696C | 44255777 | 44255777 | | | | |
| DI | c.1696G | 44255777 | 44255777 | | | | |
| DI | c.1653C | 44255820 | 44255820 | | | | |
| DI | c.1653G | 44255820 | 44255820 | | | | |
| DI | c.1438A | 44257538 | 44257538 | | | | |
| DI | c.1438G | 44257538 | 44257538 | | | | |
| DI | c.1462A | 44257514 | 44257514 | | | | |

To further illustrate the present disclosure, the primer set, the kit, and the method for genotyping multi-RBC blood group system based on NGS provided by the present disclosure are described in detail below in connection with examples, but these examples should not be construed as limiting the claimed scope of the present disclosure.

Example 1

S1. A genomic DNA was extracted separately from 5 whole blood samples (H07951D, H07949D, H07934D, H07936D, H07939D), 5 plasma samples (H07945D, H07942D, H07943D, H07948D, H07938D), and 4 paraffin tissue samples (H07929D, H07940D, H07941D, H07947D) using magnetic beads, the concentration and purity were measured, and then 10 mM Tris-HCl was added to dilute each sample to 200 ng/μL. The quality of each sample was tested using 1.5% agarose gel electrophoresis, and qualified samples were included in the group and labeled separately.

S2. The primer pairs of each pool in Table 2 were used to prepare 3 amplification systems, including: specific primer mix 1 μL (pool1, pool2, and pool3); enzyme mix Pxp-1st-mix 3 μL; genome template 1 μL (200 ng); nuclease-free water 7.5 μL, total volume 12.5 μL. There were 3 tubes of specific primer mixture in total, and 1 sample needed to be divided into 3 tubes for PCR.

A PCR reaction program of the first amplification included: initial denaturation at 98° C. for 20 min; 9 cycles of denaturation at 98° C. for 15 s, annealing at 62° C. for 20 min, extension at 68° C. for 60 s, and extension at 72° C. for 60 s; extension at 72° C. for 5 min; and heat preservation at 10° C.

S3. The PCR amplification products (pre-library products) of each sample were purified using purification magnetic beads. The remaining primers, gDNA and dNTPs were removed from the PCR product, and the amplification products were recovered.

S4. The purified products were further amplified by PCR using universal sequencing adapters (N5XX and A7XX) carrying an index.

A reaction system of the PCR amplification included: enzyme mixture Pxp-2nd-mix 6.5 μL; pre-library product 4 μL; universal adapter N5XX 1 μL, universal adapter A7XX 1 μL, with a total volume of 12.5 μL. The same sample included 3 pre-library products, which were added to 3 tubes of PCR master mix containing the same universal adapter.

The PCR reaction program was preferably: initial denaturation at 98° C. for 2 min; 23 cycles of denaturation at 98° C. for 15 s, extension at 68° C. for 60 s, and extension at 72° C. for 60 s; extension at 72° C. for 10 min; and heat preservation at 4° C.

Figure 2:
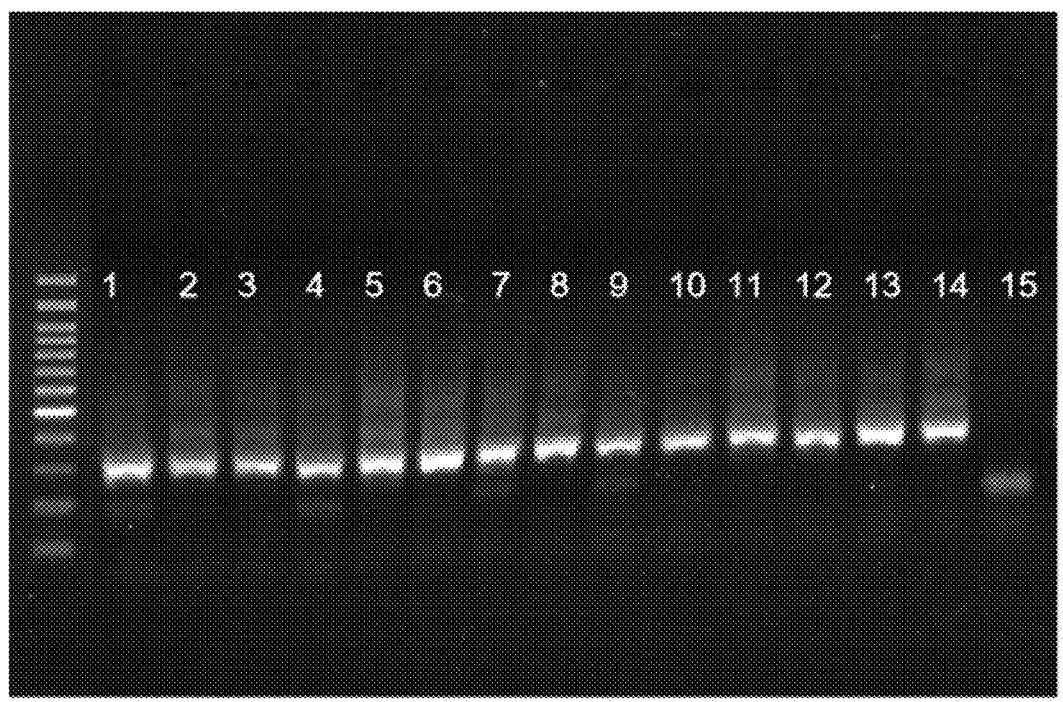
FIG. 2 shows an electrophoresis pattern of primer specificity verification in Example 1.

As shown in FIG. 2, the amplification products of 14 samples all showed clear and bright target bands in the range of 200 bp to 500 bp, which was consistent with the expected design. Moreover, there was an extremely low primer-dimer content, and the size of the primer-dimer was obviously different from that of the amplified target fragment. This indicated that the PCR amplification primers and detection methods could break through the limitation of traditional methods, thus producing a large number of primer dimers to enhance the primer capture efficiency.

Example 2

Using steps S1 to S4 in Example 1, primer detection sensitivity verification was conducted on the genomic samples extracted from 4 whole blood samples (H08215D, H07953D, H07997D, H07951D), 4 plasma samples (H07949D, H07934D, H07936D, H07945D), and 3 tissue samples (H07942D, H07943D, H07948D) that passed the quality inspection. The samples in each case had a starting concentration of 200 ng/μL, and were diluted in 5-fold, 10-fold, and 20-fold concentration gradients. After dilution, the samples had concentrations of 40 ng/μL, 20 ng/μL, and 10 ng/μL, and were labeled with the sample name and concentration, respectively.

Figure 3:
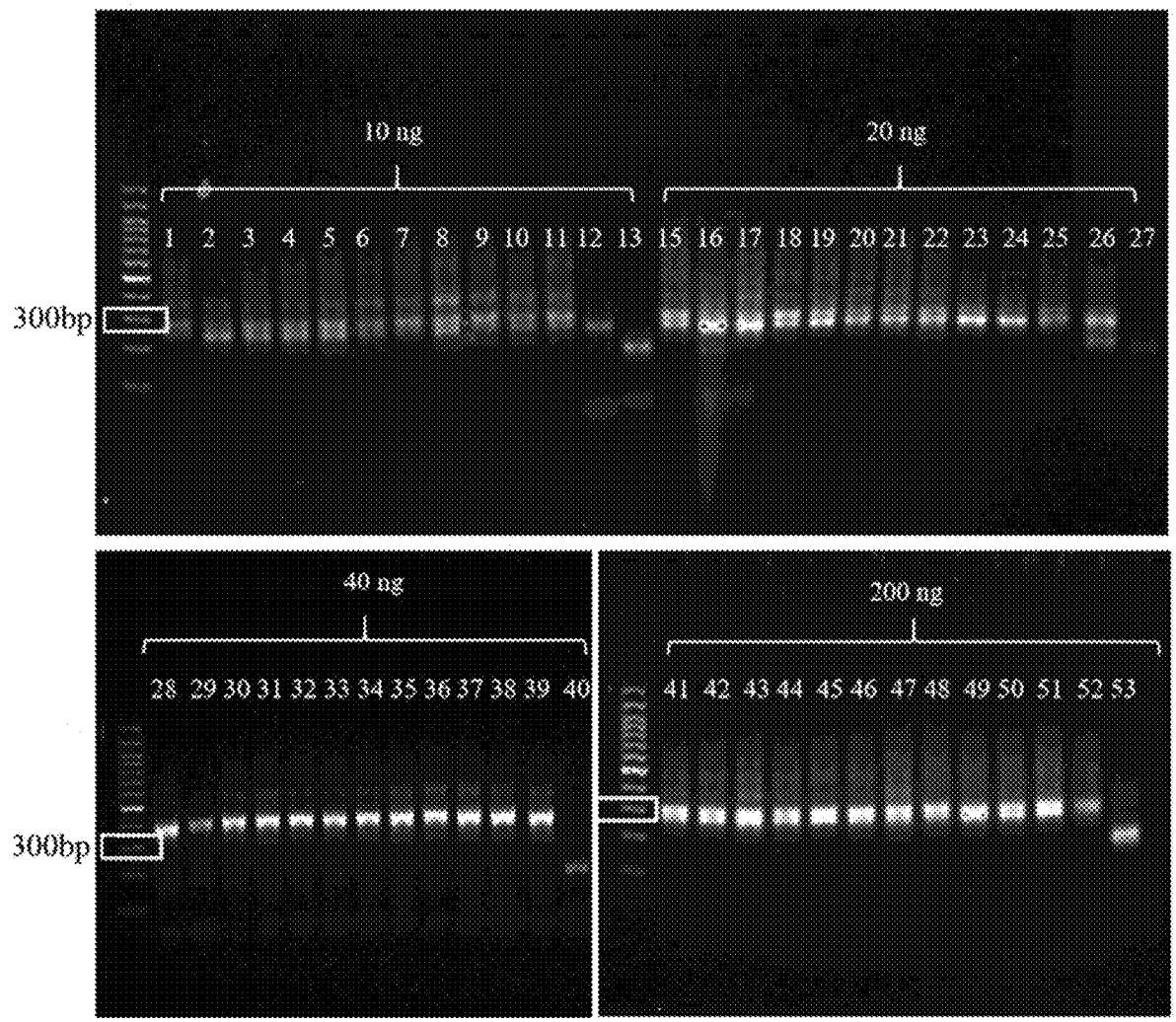
FIG. 3 shows an electrophoresis pattern of primer detection sensitivity verification in Example 2.

As shown in FIG. 3, the amplification products of the 11 samples were mainly concentrated at 200 bp to 500 bp, which was consistent with the expected design. Moreover, there was an extremely low primer-dimer content, and the size of the primer-dimer was obviously different from that of amplified target fragment. All 11 samples had clear and bright target bands at different template usage levels, and the target band could still be successfully amplified even if the template content was as low as 10 ng. This indicated that the PCR amplification primer and detection method of the present disclosure could break through the limitations of traditional methods and improve a detection sensitivity.

Example 3

Using the same method as in Example 1, primer detection repeatability verification was conducted on the genome sample extracted from whole blood samples (H07939D, H07938D), plasma samples (H07929D, H07940D), and paraffin tissue samples (H07941D, H07947D) that passed the quality inspection. Each of the 6 samples was amplified by 2 different operators on 2 different laboratory platforms according to steps S2 to S4 in Example 1, with a sample injection volume of 1 μL. The 6 samples were amplified by different operators in different laboratories using primers specific for a causative gene of large vestibular aqueduct syndrome.

Figure 4:
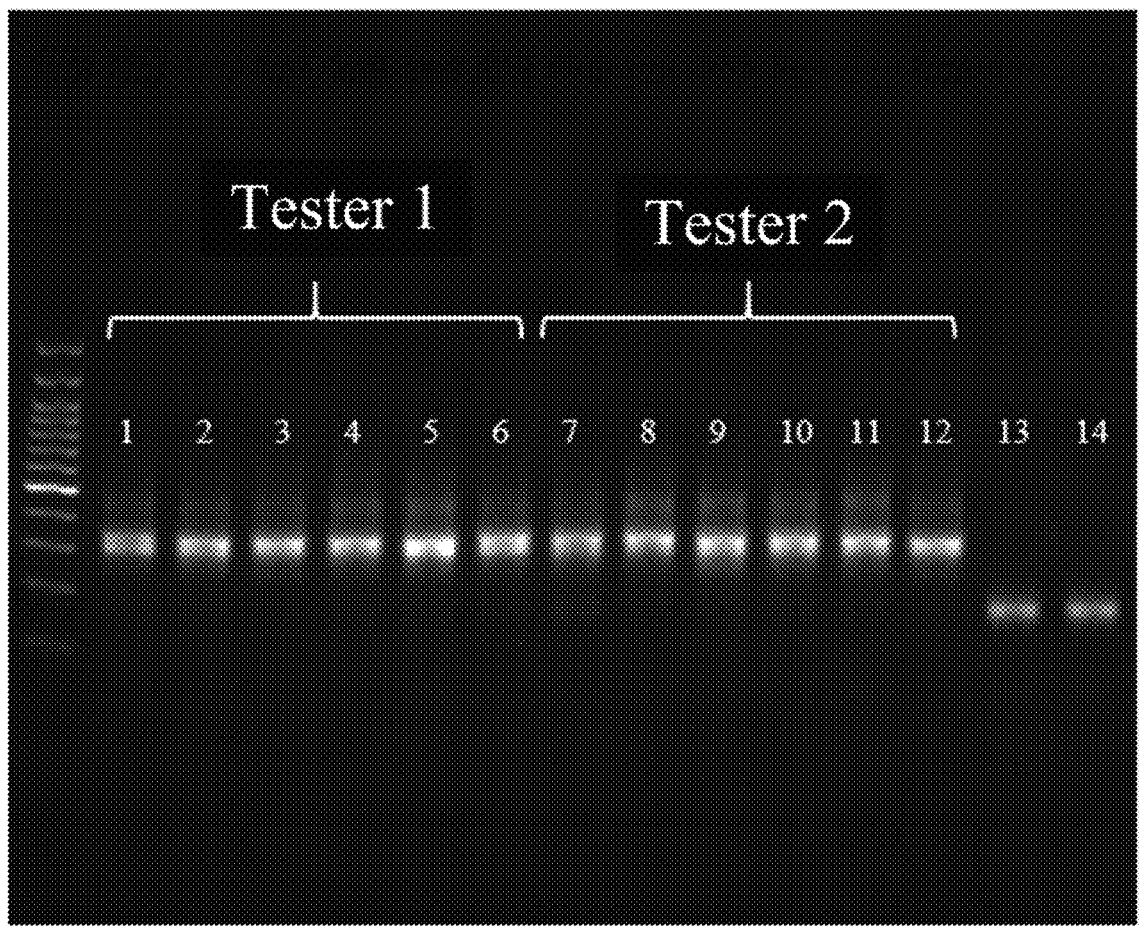
FIG. 4 shows results of the repeatability verification of primer detection in Example 3.

As shown in FIG. 4, a total of 12 amplification products from 6 samples were mainly concentrated at 200 bp to 500 bp and there were no other non-specific bands, which was consistent with the expected design. Moreover, there was an extremely low primer-dimer content, and the size of the primer-dimer was obviously different from that of amplified target fragment. There was no difference in the test results between different operators and different experimental platforms. This showed that the PCR amplification primer and detection method of the present disclosure had desirable repeatability.

Example 4

17-System Blood Group Genotyping and Rare Blood Group Detection Based on Targeted Capture NGS Technology
1. Experimental Material Sources:

From the blood samples of voluntary blood donors tested by the Shenzhen Blood Center Rare Blood Group Bank from 2018 to 2023, 20 different types of rare blood group samples were selected, namely: No. 1 and 2 H−, No. 3 RHnull, No. 4 and 5 D−−, No. 6 CCDEE, No. 7 S+s−, No. 8 S−s−, No. 9 Fy(a−b+), No. 10 Fy(a−b−), No. 11 Le(a+b−), No. 12 Jk(a−b−), No. 13 K+, No. 14 Jr(a−), No. 15 Di(a+b−), No. 16 Di(a−b−), No. 17 InLu, No. 18 p, No. 19 RHD mixed field of view, and No. 20 RHCcEe mixed field of view.

These samples covered four types that were detected by different detection technologies and could not be solved by traditional serology, PCR-SSP, and Sanger, but could only achieve clear results through this technology of the present disclosure:

(1) 13 cases of rare blood group samples detected through blood group serology experiments;
(2) 3 cases of rare blood group samples detected by PCR-SSP genotyping without commercially available serological detection reagents;
(3) 2 cases of rare blood group samples deduced by Sanger without clear results using PCR-SSP genotyping and without commercially available serological detection reagents; and
(4) 2 cases with abnormal blood group serology test results showing mixed fields of view and Sanger showing all double peaks and unable to interpret the results.

2. Experimental Procedure:

(1) When collecting venous blood, a sample of 5 mL/ (person) was retained in an EDTA-Na2 anticoagulant tube and stored at 4° C.
(2) Blood group serological test was conducted within 72 h for 31 key rare blood groups in 17 target blood group systems. Only 11 rare blood groups were suitable for serological technology, while the remaining 20 rare blood groups could not be detected by serological test since there were no commercially available antibody reagents or the detection principle was not applicable.
(3) Genomic DNA was extracted from the 20 samples within 72 h, and genotyping was conducted using PCR-SSP, Sanger, and the technology of the present disclosure in sequence.

3. Experimental Results:

(1) Blood type serological test results: among the 20 samples in Table 4, only 13 cases obtained clear blood group results through serological test, namely: No. 1 and 2 H−, No. 3 RHnull, No. 4 and 5 D−−, No. 6 CCDEE, No. 7 S+s−, No. 8 S−s−, No. 9 Fy(a−b+), No. 10 Fy(a−b−), No. 11 Le(a±b−), No. 12 Jk(a−b−), No. 13 K+. There were 2 cases that could not be interpreted since their serological results showed mixed fields of view, while the other 5 cases were not suitable for serological test.

In 7 samples, genetic testing technologies based on SNP sites, such as PCR-SSP and MassArray nucleic acid mass spectrometry, were able to confirm blood group results; for example, for rare blood group samples No. 14-16 without commercially available serological detection reagents, their rare blood group types obtained through PCR-SSP were: No. 14 Jr(a−), No. 15 was Di(a+b−), and No. 16 Di(a−b−). In the other 13 samples, due to complex and unclear genetic polymorphisms, the primers designed based on SNP sites were off-target and the genotype could not be determined.

Sanger was conducted to sequence the gene coding region, and clear allele types could be directly obtained for 10 pure and mutant samples. Another 7 cases had multiple heterozygous mutation sites, large fragment insertions, and hybrid recombination. In this case, Sanger could not directly differentiate between these different heterozygotes. Because Sanger generally produced mixed signals that were not sufficient to distinguish a relative proportion of multiple alleles, and predictions could only be made based on guesswork. The technology of the present disclosure could solve such problems more accurately. Through SNP detection and haplotype analysis, multiple alleles could be more effectively identified to provide more information to infer haplotypes (allele types). For the No. 17 and No. 18 of rare blood group samples deduced by Sanger without clear results using PCR-SSP genotyping and without commercially available serological detection reagents, their rare blood groups were speculated by Sanger to be: No. 17 InLu, No. 18 p.

There were also 2 cases No. 19 and No. 20 with abnormal blood group serology test results showing mixed fields of view and Sanger showing all double peaks and unable to interpret the results. The Sanger found dual genetic backgrounds that were indistinguishable. The technology of the present disclosure could obtain the blood group chimera

TABLE 4

Serological identification results of 20 rare blood group specimens

| Sample NO | H Anti-H | RH Anti-D | Anti-C | Anti-c | Anti-E | Anti-e | MNS Anti-S | Anti-s | Kidd Anti-Jka | Anti-Jkb | Diego Anti-Dia | Duffy Anti-Fya | Anti-Fyb | Lewis Anti-Lea | Anti-Leb | Kell Anti-K | Anti-k | Results (rare blood group) |
|---|---|---|---|---|---|---|---|---|---|---|---|---|---|---|---|---|---|---|
| 1 | 0 | + | + | + | + | + | 0 | + | + | 0 | + | + | 0 | 0 | + | 0 | + | H− |
| 2 | 0 | + | + | + | + | + | + | + | + | + | + | + | 0 | 0 | + | 0 | + | H− |
| 3 | + | 0 | 0 | 0 | 0 | 0 | 0 | + | + | 0 | + | + | + | 0 | + | 0 | + | RHnull |
| 4 | + | + | 0 | + | 0 | 0 | 0 | + | + | + | 0 | + | + | 0 | + | 0 | + | D−− |
| 5 | + | + | 0 | 0 | 0 | 0 | + | 0 | + | + | + | + | 0 | 0 | + | 0 | + | D−− |
| 6 | + | + | + | 0 | + | 0 | 0 | + | + | + | 0 | + | 0 | 0 | + | 0 | + | CCDEE |
| 7 | + | + | + | + | + | + | + | 0 | + | + | + | + | + | 0 | + | 0 | + | S + s− |
| 8 | + | + | + | + | + | + | 0 | 0 | 0 | + | + | + | 0 | 0 | + | 0 | + | S − s− |
| 9 | + | + | + | + | + | + | 0 | + | 0 | + | + | 0 | + | 0 | + | 0 | + | Fy(a − b+) |
| 10 | + | + | + | + | + | + | + | + | + | 0 | + | 0 | 0 | 0 | + | 0 | + | Fy(a − b−) |
| 11 | + | + | + | + | + | + | 0 | + | + | + | + | + | 0 | ± | 0 | 0 | + | Le(a + b−) |
| 12 | + | + | + | + | + | + | 0 | + | 0 | 0 | + | + | 0 | 0 | + | 0 | + | Jk(a − b−) |
| 13 | + | + | + | + | + | + | 0 | + | + | + | + | + | 0 | 0 | + | + | + | K+ |
| 14 | + | + | + | + | + | + | + | + | + | + | 0 | + | 0 | 0 | + | 0 | + | Unknown |
| 15 | + | + | + | + | + | + | 0 | + | + | + | + | + | 0 | 0 | + | 0 | + | Unknown |
| 16 | + | + | + | + | + | + | 0 | + | + | + | 0 | + | 0 | 0 | + | 0 | + | Unknown |
| 17 | + | + | + | + | + | + | 0 | + | 0 | + | + | + | + | 0 | + | 0 | + | Unknown |
| 18 | + | + | + | + | + | + | 0 | + | 0 | + | + | + | 0 | 0 | + | 0 | + | Unknown |
| 19 | + | mf | + | + | + | + | 0 | + | + | 0 | + | + | + | 0 | + | 0 | + | Unknown |
| 20 | + | + | mf | mf | mf | mf | 0 | + | + | 0 | 0 | + | + | 0 | + | 0 | + | Unknown |

(2) Genotyping results: three different genetic testing technologies were used to conduct genotyping of 20 rare blood group specimens. The results were detailed in Table 5.

allele types by analyzing the relative proportions of SNPs, which were: No. 19 RHD*01 (70%)/RHD*01N.01 (30%), No. 20 RHCE*Ce (20%)/RHCE*cE(80%).

TABLE 5

Comparison of genotyping results of 20 rare blood group specimens using three different types of genetic testing technologies

| | PCR-SSP and MassArray nucleic acid mass spectrometry (detection technology based on SNP sites) | | | Sanger | | | Technology of the present disclosure | | | | |
|---|---|---|---|---|---|---|---|---|---|---|---|
| Sample NO | Experimental results | Whether blood group could be confirmed? | Analysis of reason | Experimental results | Whether blood group could be confirmed? | Analysis of reason | Experimental results | Whether blood group could be confirmed? | Analysis of reason | Confirmed rare blood group types | Was it consistent with serology results? |
| 1 | c.881_882delTT | Yes | / | c.881_882delTT | Yes | / | c.881_882delTT | Yes | / | H– | Yes |
| 2 | Amplification failure | No | Complex gene polymorphism, primer off-target | c.360-400del/c.551_552delAG | Speculated | The sequencing result was heterozygous and the allele type could not be directly obtained | c.360-400del FUT1*01/FUT1*01N.06 | Yes | Allelic types could be obtained by analyzing the relative proportions of SNPs | H– | Yes |
| 3 | Amplification failure | No | Whole gene deletion, primer off-target | RHD + RhCE deletion | Yes | / | RHD + RhCE deletion | Yes | / | RHnull | Yes |
| 4 | Amplification failure | No | Whole gene deletion, primer off-target | RHD deletion | Yes | / | RHD deletion | Yes | / | D–– | Yes |
| 5 | Amplification failure | No | Large fragment recombination, primer off-target | / | Speculated | Large segment heterozygous recombination, unable to obtain allele type | CE exons 3-9/CE exons 2-7 | Yes | Allelic types could be obtained by analyzing the relative proportions of SNPs | D–– | Yes |
| 6 | Amplification failure | No | Complex gene polymorphism, primer off-target | c.48G/C, c.150C/T, c.178C/A, c.201A/GA c.203A/G, c.307C/T, c.676G/C, c.722C/T | Speculated | The sequencing result was multiple heterozygotes and the allele type could not be directly obtained | RHCE*CE/RHCE*CE.01 | Yes | Allelic types could be obtained by analyzing the relative proportions of SNPs | CCDEE | Yes |
| 7 | c.251GG | Yes | / | c.251C > G in GYPB*S/c.251C > G in GYPB*S | Yes | Conventional homozygous mutations, allelic types could be obtained | c.251C > G in GYPB*S/c.251C > G in GYPB*S | Yes | / | S– | Yes |

TABLE 5-continued

Comparison of genotyping results of 20 rare blood group specimens using three different types of genetic testing technologies

| | PCR-SSP and MassArray nucleic acid mass spectrometry (detection technology based on SNP sites) | | | Sanger | | | Technology of the present disclosure | | | | |
|---|---|---|---|---|---|---|---|---|---|---|---|
| Sample NO | Experimental results | Whether blood group could be confirmed? | Analysis of reason | Experimental results | Whether blood group could be confirmed? | Analysis of reason | Experimental results | Whether blood group could be confirmed? | Analysis of reason | Confirmed rare blood group types | Was it consistent with serology results? |
| 8 | Amplification failure | No | Large fragment inserted, primer off-target | c.143C/T, c.251GG, GYP(B1-136-B?137-204-A205-229-B230-366) | Speculated | There was a large insertion before the key SNP site, resulting in frame shift, and it was a heterozygous mutation, the allelic type could not be obtained | GYP*Mur/ GYP*Mur | Yes | Serology test misjudgment discovered! It was due to limitations of the binding sites of commercially available antibodies | JENU | No (actually a variant, easily missed) |
| 9 | c.125AA | Yes | / | c.125AA | Yes | Conventional homozygous mutations, allelic types could be obtained | FY*B/FY*B | Yes | / | Fy (a − b+) | Yes |
| 10 | Amplification failure | No | Complex gene polymorphism, primer off-target | c.287G > A/c.287G > A | Yes | Unconventional, homozygous mutations could result in allelic types | FY*01N.04/ FY*01N.04 | Yes | / | Fy (a − b+) | Yes |
| 11 | Amplification failure | No | Complex gene polymorphism, primer off-target | c.13G > A, c.59T > G, c.202T > CA c.314C > TA c.484G > A. c.508G > A | Speculated | The sequencing result was multiple heterozygotes and the allele type could not be directly obtained | FUT3* 01N.01.05/ FUT3* 01N.03.03 | Yes | Allelic types could be obtained by analyzing the relative proportions of SNPs | Le (a − b−) | No (blood group antigens were adsorbed and difficult to accurately identify) |
| 12 | Amplification failure | No | Complex gene polymorphism, primer off-target | c.956C > Tc.516 530del | Speculated | Single-base mutations superimpose fragment deletions, unable to directly obtain allelic types | JK*01N.04/ JK*01N.12 | Yes | Allelic types could be obtained by analyzing the relative proportions of SNPs | Jk (a − b−) | Yes |
| 13 | c.578TT | Yes | / | c.578TT | Yes | Conventional homozygous mutations, allelic types could be obtained | KEL*01.01/ KEL*01.01 | Yes | / | K+ | Yes |

TABLE 5-continued

Comparison of genotyping results of 20 rare blood group specimens using three different types of genetic testing technologies

| | PCR-SSP and MassArray nucleic acid mass spectrometry (detection technology based on SNP sites) | | | Sanger | | | Technology of the present disclosure | | | | |
|---|---|---|---|---|---|---|---|---|---|---|---|
| Sample NO | Experi-mental results | Whether blood group could be con-firmed? | Analysis of reason | Experi-mental results | Whether blood group could be con-firmed? | Analysis of reason | Experi-mental results | Whether blood group could be con-firmed? | Analysis of reason | Con-firmed rare blood group types | Was it consistent with serology results? |
| 14 | c.376TT | Yes | / | c.376TT | Yes | Conventional homozygous mutations, allelic types could be obtained | ABCG2* 01N.01/ ABCG2* 01N.01 | Yes | / | Jr(a−) | Serologically unidentifiable (no commercially available antibodies) |
| 15 | c.2561TT | Yes | / | c.2561TT | Yes | Conventional homozygous mutations, allelic ypes could be obtained | DI*A/DI*A | Yes | / | Di (a + b−) | Serologically unidentifiable (no commercially available antibodies) |
| 16 | c.1462AA | Yes | / | c.1462AA | Yes | Conventional homozygous mutations, allelic types could be obtained | DI*02N.01/ DI*02N.01 | Yes | / | Di (a − b−) | Serologically unidentifiable (no commercially available antibodies) |
| 17 | Ampli-fication failure | No | Genetic background different from that of Caucasian people, primer off-target | c.304T > C c.1021T > C | Spe-culated | The sequencing result was multiple heterozygotes and the allele type could not be directly obtained | c. 1021T > C in KLF1* BGM12/ KLF1* BGM12 | Yes | Allelic types could be obtained by analyzing the relative proportions of SNPs | InLu | Yes |
| 18 | Ampli-fication failure | No | Complex gene poly-morphism, primer off-target | c.100G > A, c.343A > T, c.418 428delins | Spe-culated | There was a short insertion before the key SNP site, resulting in frame shift, it was superposition of multiple heterozygous mutations, the allelic type could not be directly obtained | c. 343A > T in A4GALT* P1.01/ c.100G > A in A4GALT* 02N.25 | Yes | Allelic types could be obtained by analyzing the relative proportions of SNPs | p | Serologically unidentifiable (no commercially available antibodies) |

TABLE 5-continued

Comparison of genotyping results of 20 rare blood group specimens using three different types of genetic testing technologies

| | PCR-SSP and MassArray nucleic acid mass spectrometry (detection technology based on SNP sites) | | | Sanger | | | Technology of the present disclosure | | | | |
|---|---|---|---|---|---|---|---|---|---|---|---|
| Sample NO | Experimental results | Whether blood group could be confirmed? | Analysis of reason | Experimental results | Whether blood group could be confirmed? | Analysis of reason | Experimental results | Whether blood group could be confirmed? | Analysis of reason | Confirmed rare blood group types | Was it consistent with serology results? |
| 19 | Ambiguous | No | Blood group mosaicism led to dual genetic backgrounds that were indistinguishable | Ambiguous | No | Blood group mosaicism led to dual genetic backgrounds that were indistinguishable | RHD*01(70%)/ RHD*01-N.01(30%) | Yes | Allelic types and proportions of two chimeric genes could be obtained by analyzing the relative proportions of SNPs | Chimera | Serologically unidentifiable (mixed fields of view, undeterminable) |
| 20 | Ambiguous | No | Blood group mosaicism led to dual genetic backgrounds that were indistinguishable | Ambiguous | No | Blood group mosaicism led to dual genetic backgrounds that were indistinguishable | RHCE*Ce(20%)/ RHCE*cE(80%) | Yes | Allelic types and proportions of two chimeric genes could be obtained by analyzing the relative proportions of SNPs | Chimera | Serologically unidentifiable (mixed fields of view, undeterminable) |

TABLE 6

Quality control results of sequencing 20 rare blood group specimens

| Sample NO | Total Reads | ReadMapped Genome | ReadMap Target | Uniformity | Specificity | Average depth | >=20x | >=30x |
|---|---|---|---|---|---|---|---|---|
| 1 | 1123474 | 852942 | 784878 | 96.01% | 92.01% | 2845 | 97.62% | 94.62% |
| 2 | 1418628 | 891892 | 779782 | 90.97% | 87.42% | 2760 | 95.98% | 92.98% |
| 3 | 1075343 | 820595 | 748465 | 95.68% | 91.20% | 2636 | 96.34% | 92.34% |
| 4 | 1403989 | 1104238 | 954835 | 94.12% | 86.46% | 3404 | 97.76% | 92.76% |
| 5 | 1225134 | 881239 | 814157 | 88.73% | 92.38% | 2952 | 97.01% | 92.01% |
| 6 | 1325877 | 1027290 | 913159 | 90.56% | 88.88% | 3283 | 96.57% | 93.57% |
| 7 | 975678 | 638289 | 598483 | 85.56% | 93.75% | 2142 | 99.18% | 96.18% |
| 8 | 1478933 | 1045310 | 930013 | 96.63% | 88.96% | 3357 | 98.43% | 95.43% |
| 9 | 1373990 | 978968 | 910049 | 90.08% | 92.95% | 3255 | 95.89% | 94.89% |
| 10 | 925554 | 724617 | 672155 | 92.86% | 92.71% | 2425 | 96.74% | 93.74% |
| 11 | 819891 | 513006 | 449650 | 94.27% | 87.63% | 1578 | 98.91% | 93.91% |
| 12 | 1345798 | 866560 | 788917 | 87.42% | 91.03% | 2854 | 97.12% | 96.12% |
| 13 | 1190323 | 929881 | 901651 | 92.74% | 96.95% | 3267 | 99.45% | 98.45% |
| 14 | 1289037 | 793274 | 689141 | 95.39% | 86.87% | 2467 | 95.23% | 94.23% |
| 15 | 1432468 | 1063321 | 979000 | 97.72% | 92.05% | 3515 | 97.07% | 95.07% |
| 16 | 845192 | 674548 | 592861 | 89.16% | 87.87% | 2145 | 99.31% | 96.31% |
| 17 | 1420141 | 866002 | 799689 | 87.31% | 92.33% | 2872 | 97.83% | 93.83% |
| 18 | 1497523 | 1035088 | 939032 | 88.62% | 90.70% | 3325 | 98.27% | 95.27% |
| 19 | 804517 | 635247 | 595731 | 95.05% | 93.77% | 2155 | 98.82% | 96.82% |
| 20 | 1156893 | 796753 | 712979 | 94.28% | 89.48% | 2527 | 97.65% | 94.65% |

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A method for simultaneously detecting genotyping of 17 RBC blood group systems, comprising the following steps:
   (1) subjecting three capture and amplification systems to first amplification separately to obtain three first amplification products;
   (2) purifying the three first amplification products separately, and subjecting three resulting purified first amplification products to second amplification with a sequencing universal adapter carrying an index separately to obtain three second amplification products; and
   (3) purifying and mixing the three second amplification products to allow sequencing to obtain the genotyping of the RBC blood group systems;
   wherein the three capture and amplification systems are prepared by using a nucleic acid extracted from a sample as a template and a primer set; and wherein the primer set comprises a first primer set having the nucleotide sequences as set forth in SEQ ID NO: 1 to SEQ ID NO: 108, a second primer set having the nucleotide sequences as set forth in SEQ ID NO: 109 to SEQ ID NO: 222, and a third primer set having the nucleotide sequences as set forth in SEQ ID NO: 223 to SEQ ID NO: 336, respectively.

2. The method according to claim 1, wherein the sample in step (1) is selected from the group consisting of a whole blood sample, a plasma sample, and a paraffin tissue sample.

3. The method according to claim 1, wherein the three capture and amplification systems in step (1) each have a volume of 25 µL, and comprise 1 µL of a mixture of the first primer set or the second primer set or the third primer set, 3 µL of an enzyme mixture Pxp-1st-mix, 1 µL of the template, and nuclease-free water as a balance.

4. The method according to claim 1, wherein a PCR reaction program of the first amplification in step (1) comprises: initial denaturation at 98° C. for 20 min; 9 cycles of denaturation at 98° C. for 15 s, annealing at 62° C. for 20 min, extension at 68° C. for 60 s, and extension at 72° C. for 60 s; extension at 72° C. for 5 min; and heat preservation at 10° C.

5. The method according to claim 1, wherein a system of the second amplification in step (2) has a volume of 12.5 µL, and comprises 6.5 µL of an enzyme mixture Pxp-2nd-mix, 4 µL for one of the three purified first amplification products, 1 µL of a universal adapter N5XX, and 1 µL of a universal adapter A7XX.

6. The method according to claim 1, wherein a PCR reaction program of the second amplification in step (2) comprises: initial denaturation at 98° C. for 2 min; 23 cycles of denaturation at 98° C. for 15 s, extension at 68° C. for 60 s, and extension at 72° C. for 60 s; extension at 72° C. for 10 min; and heat preservation at 4° C.

7. The method according to claim 3, wherein a PCR reaction program of the first amplification in step (1) comprises: initial denaturation at 98° C. for 20 min; 9 cycles of denaturation at 98° C. for 15 s, annealing at 62° C. for 20 min, extension at 68° C. for 60 s, and extension at 72° C. for 60 s; extension at 72° C. for 5 min; and heat preservation at 10° C.

8. The method according to claim 5, wherein a PCR reaction program of the second amplification in step (2) comprises: initial denaturation at 98° C. for 2 min; 23 cycles of denaturation at 98° C. for 15 s, extension at 68° C. for 60 s, and extension at 72° C. for 60 s; extension at 72° C. for 10 min; and heat preservation at 4° C.

* * * * *

```
                             SEQUENCE LISTING

Sequence total quantity: 336
SEQ ID NO: 1            moltype = DNA   length = 20
FEATURE                 Location/Qualifiers
source                  1..20
                        mol_type = other DNA
                        note = Sequence of forward primer for RhD-1
                        organism = synthetic construct
SEQUENCE: 1
gccctcaagt aggtgttgga                                                    20

SEQ ID NO: 2            moltype = DNA   length = 21
FEATURE                 Location/Qualifiers
source                  1..21
                        mol_type = other DNA
                        note = Sequence of reverse primer for RhD-1
                        organism = synthetic construct
SEQUENCE: 2
ccctgctatt tgctcctgtg a                                                  21

SEQ ID NO: 3            moltype = DNA   length = 20
FEATURE                 Location/Qualifiers
source                  1..20
                        mol_type = other DNA
                        note = Sequence of forward primer for RhD-6
                        organism = synthetic construct
SEQUENCE: 3
gacctttgga gcaggagtgt                                                    20

SEQ ID NO: 4            moltype = DNA   length = 21
FEATURE                 Location/Qualifiers
source                  1..21
                        mol_type = other DNA
                        note = Sequence of reverse primer for RhD-6
                        organism = synthetic construct
SEQUENCE: 4
gtcctgttag acccaagtgc t                                                  21

SEQ ID NO: 5            moltype = DNA   length = 20
FEATURE                 Location/Qualifiers
source                  1..20
                        mol_type = other DNA
                        note = Sequence of forward primer for RhD-9
                        organism = synthetic construct
SEQUENCE: 5
gtctcacctg ccaatctgct                                                    20

SEQ ID NO: 6            moltype = DNA   length = 20
FEATURE                 Location/Qualifiers
source                  1..20
                        mol_type = other DNA
                        note = Sequence of reverse primer for RhD-9
                        organism = synthetic construct
SEQUENCE: 6
cccagctaag gactctgcac                                                    20

SEQ ID NO: 7            moltype = DNA   length = 22
FEATURE                 Location/Qualifiers
source                  1..22
                        mol_type = other DNA
                        note = Sequence of forward primer for RhD-12
                        organism = synthetic construct
SEQUENCE: 7
ggctgtttca agagatcaag cc                                                 22

SEQ ID NO: 8            moltype = DNA   length = 20
FEATURE                 Location/Qualifiers
source                  1..20
                        mol_type = other DNA
                        note = Sequence of reverse primer for RhD-12
                        organism = synthetic construct
SEQUENCE: 8
ttctctgact ccagtgcctg                                                    20
```

-continued

```
SEQ ID NO: 9            moltype = DNA   length = 20
FEATURE                 Location/Qualifiers
source                  1..20
                        mol_type = other DNA
                        note = Sequence of forward primer for RhCE-15
                        organism = synthetic construct
SEQUENCE: 9
cccagctaag gactctgcac                                                 20

SEQ ID NO: 10           moltype = DNA   length = 20
FEATURE                 Location/Qualifiers
source                  1..20
                        mol_type = other DNA
                        note = Sequence of reverse primer for RhCE-15
                        organism = synthetic construct
SEQUENCE: 10
gtctcacctg ccaatctgct                                                 20

SEQ ID NO: 11           moltype = DNA   length = 20
FEATURE                 Location/Qualifiers
source                  1..20
                        mol_type = other DNA
                        note = Sequence of forward primer for RhCE-17
                        organism = synthetic construct
SEQUENCE: 11
ttagacccaa gtgctgccca                                                 20

SEQ ID NO: 12           moltype = DNA   length = 20
FEATURE                 Location/Qualifiers
source                  1..20
                        mol_type = other DNA
                        note = Sequence of reverse primer for RhCE-17
                        organism = synthetic construct
SEQUENCE: 12
ctcgaggctc agacctttgg                                                 20

SEQ ID NO: 13           moltype = DNA   length = 20
FEATURE                 Location/Qualifiers
source                  1..20
                        mol_type = other DNA
                        note = Sequence of forward primer for RhCE-20
                        organism = synthetic construct
SEQUENCE: 13
gaacctgtcc tttcggggtc                                                 20

SEQ ID NO: 14           moltype = DNA   length = 20
FEATURE                 Location/Qualifiers
source                  1..20
                        mol_type = other DNA
                        note = Sequence of reverse primer for RhCE-20
                        organism = synthetic construct
SEQUENCE: 14
aagatctgac cgtgatggcg                                                 20

SEQ ID NO: 15           moltype = DNA   length = 20
FEATURE                 Location/Qualifiers
source                  1..20
                        mol_type = other DNA
                        note = Sequence of forward primer for RhCE-22
                        organism = synthetic construct
SEQUENCE: 15
cctgctattt gctcctgtga                                                 20

SEQ ID NO: 16           moltype = DNA   length = 21
FEATURE                 Location/Qualifiers
source                  1..21
                        mol_type = other DNA
                        note = Sequence of reverse primer for RhCE-22
                        organism = synthetic construct
SEQUENCE: 16
ctcaagccct caagtaggtg t                                               21

SEQ ID NO: 17           moltype = DNA   length = 20
FEATURE                 Location/Qualifiers
source                  1..20
                        mol_type = other DNA
                        note = Sequence of forward primer for FY-6
                        organism = synthetic construct
SEQUENCE: 17
```

```
ttgtcaacat gtctggccca                                                    20

SEQ ID NO: 18         moltype = DNA   length = 20
FEATURE               Location/Qualifiers
source                1..20
                      mol_type = other DNA
                      note = Sequence of reverse primer for FY-6
                      organism = synthetic construct
SEQUENCE: 18
aagaaaccac ccgcttcaca                                                    20

SEQ ID NO: 19         moltype = DNA   length = 20
FEATURE               Location/Qualifiers
source                1..20
                      mol_type = other DNA
                      note = Sequence of forward primer for SLC35C1-2
                      organism = synthetic construct
SEQUENCE: 19
gagggccgca atactcagtc                                                    20

SEQ ID NO: 20         moltype = DNA   length = 20
FEATURE               Location/Qualifiers
source                1..20
                      mol_type = other DNA
                      note = Sequence of reverse primer for SLC35C1-2
                      organism = synthetic construct
SEQUENCE: 20
ttcgtggtgt agatggcgtt                                                    20

SEQ ID NO: 21         moltype = DNA   length = 21
FEATURE               Location/Qualifiers
source                1..21
                      mol_type = other DNA
                      note = Sequence of forward primer for DI-1
                      organism = synthetic construct
SEQUENCE: 21
gccactcaca cactgaagct c                                                  21

SEQ ID NO: 22         moltype = DNA   length = 21
FEATURE               Location/Qualifiers
source                1..21
                      mol_type = other DNA
                      note = Sequence of reverse primer for DI-1
                      organism = synthetic construct
SEQUENCE: 22
tggggtgtga taggcactga c                                                  21

SEQ ID NO: 23         moltype = DNA   length = 20
FEATURE               Location/Qualifiers
source                1..20
                      mol_type = other DNA
                      note = Sequence of forward primer for DI-3
                      organism = synthetic construct
SEQUENCE: 23
gctgttcttg aacttgcgca                                                    20

SEQ ID NO: 24         moltype = DNA   length = 20
FEATURE               Location/Qualifiers
source                1..20
                      mol_type = other DNA
                      note = Sequence of reverse primer for DI-3
                      organism = synthetic construct
SEQUENCE: 24
ggtattttcc agcccaagcc                                                    20

SEQ ID NO: 25         moltype = DNA   length = 20
FEATURE               Location/Qualifiers
source                1..20
                      mol_type = other DNA
                      note = Sequence of forward primer for DI-5
                      organism = synthetic construct
SEQUENCE: 25
tgcactgcag tggagatcag                                                    20

SEQ ID NO: 26         moltype = DNA   length = 20
FEATURE               Location/Qualifiers
source                1..20
                      mol_type = other DNA
                      note = Sequence of reverse primer for DI-5
```

```
                                      -continued organism = synthetic construct
SEQUENCE: 26
actcttgcct ctgaccctct                                              20

SEQ ID NO: 27           moltype = DNA   length = 20
FEATURE                 Location/Qualifiers
source                  1..20
                        mol_type = other DNA
                        note = Sequence of forward primer for JK-3
                        organism = synthetic construct
SEQUENCE: 27
gcaagtgcaa ccaaagctca                                              20

SEQ ID NO: 28           moltype = DNA   length = 25
FEATURE                 Location/Qualifiers
source                  1..25
                        mol_type = other DNA
                        note = Sequence of reverse primer for JK-3
                        organism = synthetic construct
SEQUENCE: 28
ggcattttga aaaccaattg taact                                        25

SEQ ID NO: 29           moltype = DNA   length = 20
FEATURE                 Location/Qualifiers
source                  1..20
                        mol_type = other DNA
                        note = Sequence of forward primer for JK-6
                        organism = synthetic construct
SEQUENCE: 29
cctgagttct gacccctcct                                              20

SEQ ID NO: 30           moltype = DNA   length = 20
FEATURE                 Location/Qualifiers
source                  1..20
                        mol_type = other DNA
                        note = Sequence of reverse primer for JK-6
                        organism = synthetic construct
SEQUENCE: 30
cagaaccctg gccctgattt                                              20

SEQ ID NO: 31           moltype = DNA   length = 20
FEATURE                 Location/Qualifiers
source                  1..20
                        mol_type = other DNA
                        note = Sequence of forward primer for FUT6-1
                        organism = synthetic construct
SEQUENCE: 31
gcgtgtctgg tacctggatt                                              20

SEQ ID NO: 32           moltype = DNA   length = 20
FEATURE                 Location/Qualifiers
source                  1..20
                        mol_type = other DNA
                        note = Sequence of reverse primer for FUT6-1
                        organism = synthetic construct
SEQUENCE: 32
cccagcagaa gcaactacga                                              20

SEQ ID NO: 33           moltype = DNA   length = 20
FEATURE                 Location/Qualifiers
source                  1..20
                        mol_type = other DNA
                        note = Sequence of forward primer for FUT3-1
                        organism = synthetic construct
SEQUENCE: 33
gagagagggt tggccacaaa                                              20

SEQ ID NO: 34           moltype = DNA   length = 19
FEATURE                 Location/Qualifiers
source                  1..19
                        mol_type = other DNA
                        note = Sequence of reverse primer for FUT3-1
                        organism = synthetic construct
SEQUENCE: 34
aggagctgga caaggacca                                               19

SEQ ID NO: 35           moltype = DNA   length = 20
FEATURE                 Location/Qualifiers
source                  1..20
```

```
                                    mol_type = other DNA
                                    note = Sequence of forward primer for FUT3-3
                                    organism = synthetic construct
SEQUENCE: 35
acagcgtctc catcatggtc                                                    20

SEQ ID NO: 36           moltype = DNA   length = 20
FEATURE                 Location/Qualifiers
source                  1..20
                        mol_type = other DNA
                        note = Sequence of reverse primer for FUT3-3
                        organism = synthetic construct
SEQUENCE: 36
cagcgactcc gacatcttca                                                    20

SEQ ID NO: 37           moltype = DNA   length = 20
FEATURE                 Location/Qualifiers
source                  1..20
                        mol_type = other DNA
                        note = Sequence of forward primer for FUT3-5
                        organism = synthetic construct
SEQUENCE: 37
gcgtgactta gggttggaca                                                    20

SEQ ID NO: 38           moltype = DNA   length = 20
FEATURE                 Location/Qualifiers
source                  1..20
                        mol_type = other DNA
                        note = Sequence of reverse primer for FUT3-5
                        organism = synthetic construct
SEQUENCE: 38
ttctcctacc tgcgtgtgtc                                                    20

SEQ ID NO: 39           moltype = DNA   length = 20
FEATURE                 Location/Qualifiers
source                  1..20
                        mol_type = other DNA
                        note = Sequence of forward primer for KLF1-3
                        organism = synthetic construct
SEQUENCE: 39
tctcggctat cacacctgga                                                    20

SEQ ID NO: 40           moltype = DNA   length = 20
FEATURE                 Location/Qualifiers
source                  1..20
                        mol_type = other DNA
                        note = Sequence of reverse primer for KLF1-3
                        organism = synthetic construct
SEQUENCE: 40
gctcctcggg tggctacttc                                                    20

SEQ ID NO: 41           moltype = DNA   length = 21
FEATURE                 Location/Qualifiers
source                  1..21
                        mol_type = other DNA
                        note = Sequence of forward primer for KLF1-8
                        organism = synthetic construct
SEQUENCE: 41
ccccaagatc tgtgactgtg g                                                  21

SEQ ID NO: 42           moltype = DNA   length = 20
FEATURE                 Location/Qualifiers
source                  1..20
                        mol_type = other DNA
                        note = Sequence of reverse primer for KLF1-8
                        organism = synthetic construct
SEQUENCE: 42
ccctcgaagg ggctatcaca                                                    20

SEQ ID NO: 43           moltype = DNA   length = 20
FEATURE                 Location/Qualifiers
source                  1..20
                        mol_type = other DNA
                        note = Sequence of forward primer for LU-2
                        organism = synthetic construct
SEQUENCE: 43
agctgcagag agaaaggacc                                                    20

SEQ ID NO: 44           moltype = DNA   length = 20
```

```
FEATURE                 Location/Qualifiers
source                  1..20
                        mol_type = other DNA
                        note = Sequence of reverse primer for LU-2
                        organism = synthetic construct
SEQUENCE: 44
cacacgtagt ctcgctcgtc                                               20

SEQ ID NO: 45           moltype = DNA  length = 21
FEATURE                 Location/Qualifiers
source                  1..21
                        mol_type = other DNA
                        note = Sequence of forward primer for LU-4
                        organism = synthetic construct
SEQUENCE: 45
cgtgtttggt aagtgtcctc g                                             21

SEQ ID NO: 46           moltype = DNA  length = 19
FEATURE                 Location/Qualifiers
source                  1..19
                        mol_type = other DNA
                        note = Sequence of reverse primer for LU-4
                        organism = synthetic construct
SEQUENCE: 46
ctgtcccctc ctcctccag                                                19

SEQ ID NO: 47           moltype = DNA  length = 20
FEATURE                 Location/Qualifiers
source                  1..20
                        mol_type = other DNA
                        note = Sequence of forward primer for LU-6
                        organism = synthetic construct
SEQUENCE: 47
cgatctctcc cagagggcta                                               20

SEQ ID NO: 48           moltype = DNA  length = 20
FEATURE                 Location/Qualifiers
source                  1..20
                        mol_type = other DNA
                        note = Sequence of reverse primer for LU-6
                        organism = synthetic construct
SEQUENCE: 48
ctcatgaggt gtggagcctg                                               20

SEQ ID NO: 49           moltype = DNA  length = 20
FEATURE                 Location/Qualifiers
source                  1..20
                        mol_type = other DNA
                        note = Sequence of forward primer for FUT2-5
                        organism = synthetic construct
SEQUENCE: 49
tcgtggtcac cagtaatggc                                               20

SEQ ID NO: 50           moltype = DNA  length = 20
FEATURE                 Location/Qualifiers
source                  1..20
                        mol_type = other DNA
                        note = Sequence of reverse primer for FUT2-5
                        organism = synthetic construct
SEQUENCE: 50
gtcggggagg gtgtaattgg                                               20

SEQ ID NO: 51           moltype = DNA  length = 20
FEATURE                 Location/Qualifiers
source                  1..20
                        mol_type = other DNA
                        note = Sequence of forward primer for FUT1-3
                        organism = synthetic construct
SEQUENCE: 51
gtgtagcctc ctgtccatcg                                               20

SEQ ID NO: 52           moltype = DNA  length = 20
FEATURE                 Location/Qualifiers
source                  1..20
                        mol_type = other DNA
                        note = Sequence of reverse primer for FUT1-3
                        organism = synthetic construct
SEQUENCE: 52
gtggggacta tctgcaggtt                                               20
```

-continued

```
SEQ ID NO: 53            moltype = DNA   length = 20
FEATURE                  Location/Qualifiers
source                   1..20
                         mol_type = other DNA
                         note = Sequence of forward primer for A4GALT-2
                         organism = synthetic construct
SEQUENCE: 53
atggggtaga aggcctcagg                                                 20

SEQ ID NO: 54            moltype = DNA   length = 20
FEATURE                  Location/Qualifiers
source                   1..20
                         mol_type = other DNA
                         note = Sequence of reverse primer for A4GALT-2
                         organism = synthetic construct
SEQUENCE: 54
tctcaagaac ctgcggaacc                                                 20

SEQ ID NO: 55            moltype = DNA   length = 20
FEATURE                  Location/Qualifiers
source                   1..20
                         mol_type = other DNA
                         note = Sequence of forward primer for A4GALT-6
                         organism = synthetic construct
SEQUENCE: 55
cccacaacgt gccagtagat                                                 20

SEQ ID NO: 56            moltype = DNA   length = 20
FEATURE                  Location/Qualifiers
source                   1..20
                         mol_type = other DNA
                         note = Sequence of reverse primer for A4GALT-6
                         organism = synthetic construct
SEQUENCE: 56
ttggctctgg ctgatgttca                                                 20

SEQ ID NO: 57            moltype = DNA   length = 20
FEATURE                  Location/Qualifiers
source                   1..20
                         mol_type = other DNA
                         note = Sequence of forward primer for B3GALNT1-1
                         organism = synthetic construct
SEQUENCE: 57
gtaagccagc acactgacct                                                 20

SEQ ID NO: 58            moltype = DNA   length = 20
FEATURE                  Location/Qualifiers
source                   1..20
                         mol_type = other DNA
                         note = Sequence of reverse primer for B3GALNT1-1
                         organism = synthetic construct
SEQUENCE: 58
gcagcccatg gcttttcttc                                                 20

SEQ ID NO: 59            moltype = DNA   length = 21
FEATURE                  Location/Qualifiers
source                   1..21
                         mol_type = other DNA
                         note = Sequence of forward primer for B3GALNT1-3
                         organism = synthetic construct
SEQUENCE: 59
tccttggcac caaatctctg g                                               21

SEQ ID NO: 60            moltype = DNA   length = 20
FEATURE                  Location/Qualifiers
source                   1..20
                         mol_type = other DNA
                         note = Sequence of reverse primer for B3GALNT1-3
                         organism = synthetic construct
SEQUENCE: 60
gccccaatgc caagtacgta                                                 20

SEQ ID NO: 61            moltype = DNA   length = 20
FEATURE                  Location/Qualifiers
source                   1..20
                         mol_type = other DNA
                         note = Sequence of forward primer for B3GALNT1-6
                         organism = synthetic construct
```

-continued

```
SEQUENCE: 61
atctgaaggg tgggaggtca                                              20

SEQ ID NO: 62           moltype = DNA  length = 20
FEATURE                 Location/Qualifiers
source                  1..20
                        mol_type = other DNA
                        note = Sequence of reverse primer for B3GALNT1-6
                        organism = synthetic construct
SEQUENCE: 62
tctctggact gtccttccga                                              20

SEQ ID NO: 63           moltype = DNA  length = 23
FEATURE                 Location/Qualifiers
source                  1..23
                        mol_type = other DNA
                        note = Sequence of forward primer for GYPA-3
                        organism = synthetic construct
SEQUENCE: 63
aggcatttga aacaagcaat gga                                          23

SEQ ID NO: 64           moltype = DNA  length = 20
FEATURE                 Location/Qualifiers
source                  1..20
                        mol_type = other DNA
                        note = Sequence of reverse primer for GYPA-3
                        organism = synthetic construct
SEQUENCE: 64
aaggaaaccc gcagaacagt                                              20

SEQ ID NO: 65           moltype = DNA  length = 20
FEATURE                 Location/Qualifiers
source                  1..20
                        mol_type = other DNA
                        note = Sequence of forward primer for YT-1
                        organism = synthetic construct
SEQUENCE: 65
tagacccatg gtggctttcc                                              20

SEQ ID NO: 66           moltype = DNA  length = 20
FEATURE                 Location/Qualifiers
source                  1..20
                        mol_type = other DNA
                        note = Sequence of reverse primer for YT-1
                        organism = synthetic construct
SEQUENCE: 66
ccttcgtgcc tgtggtagat                                              20

SEQ ID NO: 67           moltype = DNA  length = 21
FEATURE                 Location/Qualifiers
source                  1..21
                        mol_type = other DNA
                        note = Sequence of forward primer for KEL-2
                        organism = synthetic construct
SEQUENCE: 67
gggacttcca tgagcttcag t                                            21

SEQ ID NO: 68           moltype = DNA  length = 21
FEATURE                 Location/Qualifiers
source                  1..21
                        mol_type = other DNA
                        note = Sequence of reverse primer for KEL-2
                        organism = synthetic construct
SEQUENCE: 68
gggttttggg tactgtgtgg a                                            21

SEQ ID NO: 69           moltype = DNA  length = 20
FEATURE                 Location/Qualifiers
source                  1..20
                        mol_type = other DNA
                        note = Sequence of forward primer for KEL-4
                        organism = synthetic construct
SEQUENCE: 69
ctcccttgtg gtcttccctt                                              20

SEQ ID NO: 70           moltype = DNA  length = 20
FEATURE                 Location/Qualifiers
source                  1..20
                        mol_type = other DNA
```

-continued

```
                        note = Sequence of reverse primer for KEL-4
                        organism = synthetic construct
SEQUENCE: 70
ctcccttgtg gtcttccctt                                                20

SEQ ID NO: 71           moltype = DNA   length = 21
FEATURE                 Location/Qualifiers
source                  1..21
                        mol_type = other DNA
                        note = Sequence of forward primer for KEL-7
                        organism = synthetic construct
SEQUENCE: 71
ggagggtcag agaagtgacg a                                              21

SEQ ID NO: 72           moltype = DNA   length = 20
FEATURE                 Location/Qualifiers
source                  1..20
                        mol_type = other DNA
                        note = Sequence of reverse primer for KEL-7
                        organism = synthetic construct
SEQUENCE: 72
gccactgggc tgtatactca                                                20

SEQ ID NO: 73           moltype = DNA   length = 20
FEATURE                 Location/Qualifiers
source                  1..20
                        mol_type = other DNA
                        note = Sequence of forward primer for KEL-10
                        organism = synthetic construct
SEQUENCE: 73
aatacacccg ctcctctcct                                                20

SEQ ID NO: 74           moltype = DNA   length = 20
FEATURE                 Location/Qualifiers
source                  1..20
                        mol_type = other DNA
                        note = Sequence of reverse primer for KEL-10
                        organism = synthetic construct
SEQUENCE: 74
ggagctgcct tcacgagtat                                                20

SEQ ID NO: 75           moltype = DNA   length = 20
FEATURE                 Location/Qualifiers
source                  1..20
                        mol_type = other DNA
                        note = Sequence of forward primer for KEL-12
                        organism = synthetic construct
SEQUENCE: 75
gagaggaaga tccccatgcc                                                20

SEQ ID NO: 76           moltype = DNA   length = 21
FEATURE                 Location/Qualifiers
source                  1..21
                        mol_type = other DNA
                        note = Sequence of reverse primer for KEL-12
                        organism = synthetic construct
SEQUENCE: 76
ccttcctcca gatctttcgg g                                              21

SEQ ID NO: 77           moltype = DNA   length = 20
FEATURE                 Location/Qualifiers
source                  1..20
                        mol_type = other DNA
                        note = Sequence of forward primer for KEL-14
                        organism = synthetic construct
SEQUENCE: 77
gtccaactgt gtcttcgcca                                                20

SEQ ID NO: 78           moltype = DNA   length = 20
FEATURE                 Location/Qualifiers
source                  1..20
                        mol_type = other DNA
                        note = Sequence of reverse primer for KEL-14
                        organism = synthetic construct
SEQUENCE: 78
agagccgatc cagacaatgg                                                20

SEQ ID NO: 79           moltype = DNA   length = 20
FEATURE                 Location/Qualifiers
```

```
source                   1..20
                         mol_type = other DNA
                         note = Sequence of forward primer for KEL-16
                         organism = synthetic construct
SEQUENCE: 79
ggctgactag gttagggggt                                                 20

SEQ ID NO: 80            moltype = DNA  length = 20
FEATURE                  Location/Qualifiers
source                   1..20
                         mol_type = other DNA
                         note = Sequence of reverse primer for KEL-16
                         organism = synthetic construct
SEQUENCE: 80
tcacctcttg gttcctccca                                                 20

SEQ ID NO: 81            moltype = DNA  length = 20
FEATURE                  Location/Qualifiers
source                   1..20
                         mol_type = other DNA
                         note = Sequence of forward primer for GATA1-1
                         organism = synthetic construct
SEQUENCE: 81
cctttccctg gacccctact                                                 20

SEQ ID NO: 82            moltype = DNA  length = 22
FEATURE                  Location/Qualifiers
source                   1..22
                         mol_type = other DNA
                         note = Sequence of reverse primer for GATA1-1
                         organism = synthetic construct
SEQUENCE: 82
acacacccac aatttcagga ct                                              22

SEQ ID NO: 83            moltype = DNA  length = 20
FEATURE                  Location/Qualifiers
source                   1..20
                         mol_type = other DNA
                         note = Sequence of forward primer for ERMAP-3
                         organism = synthetic construct
SEQUENCE: 83
ggatgggaag gaccaggatg                                                 20

SEQ ID NO: 84            moltype = DNA  length = 20
FEATURE                  Location/Qualifiers
source                   1..20
                         mol_type = other DNA
                         note = Sequence of reverse primer for ERMAP-3
                         organism = synthetic construct
SEQUENCE: 84
ttgccacaaa tgaccctggg                                                 20

SEQ ID NO: 85            moltype = DNA  length = 22
FEATURE                  Location/Qualifiers
source                   1..22
                         mol_type = other DNA
                         note = Sequence of forward primer for ART4-4
                         organism = synthetic construct
SEQUENCE: 85
ggccatggct ctagtaaagt ca                                              22

SEQ ID NO: 86            moltype = DNA  length = 19
FEATURE                  Location/Qualifiers
source                   1..19
                         mol_type = other DNA
                         note = Sequence of reverse primer for ART4-4
                         organism = synthetic construct
SEQUENCE: 86
tcgacttcga cttcgcacc                                                  19

SEQ ID NO: 87            moltype = DNA  length = 20
FEATURE                  Location/Qualifiers
source                   1..20
                         mol_type = other DNA
                         note = Sequence of forward primer for ART4-7
                         organism = synthetic construct
SEQUENCE: 87
tcagtctcat ccgtaaccgt                                                 20
```

-continued

```
SEQ ID NO: 88              moltype = DNA   length = 20
FEATURE                    Location/Qualifiers
source                     1..20
                           mol_type = other DNA
                           note = Sequence of reverse primer for ART4-7
                           organism = synthetic construct
SEQUENCE: 88
gacttcggca ttcccctgaa                                                 20

SEQ ID NO: 89              moltype = DNA   length = 20
FEATURE                    Location/Qualifiers
source                     1..20
                           mol_type = other DNA
                           note = Sequence of forward primer for ABCG2-2
                           organism = synthetic construct
SEQUENCE: 89
cggcctccca aagtactagg                                                 20

SEQ ID NO: 90              moltype = DNA   length = 20
FEATURE                    Location/Qualifiers
source                     1..20
                           mol_type = other DNA
                           note = Sequence of reverse primer for ABCG2-2
                           organism = synthetic construct
SEQUENCE: 90
cgagcaaaag gggaaaagcc                                                 20

SEQ ID NO: 91              moltype = DNA   length = 20
FEATURE                    Location/Qualifiers
source                     1..20
                           mol_type = other DNA
                           note = Sequence of forward primer for ABCG2-4
                           organism = synthetic construct
SEQUENCE: 91
gctcaggatc tcaggatgcg                                                 20

SEQ ID NO: 92              moltype = DNA   length = 20
FEATURE                    Location/Qualifiers
source                     1..20
                           mol_type = other DNA
                           note = Sequence of reverse primer for ABCG2-4
                           organism = synthetic construct
SEQUENCE: 92
gtgctgtgcc cactcaaaag                                                 20

SEQ ID NO: 93              moltype = DNA   length = 20
FEATURE                    Location/Qualifiers
source                     1..20
                           mol_type = other DNA
                           note = Sequence of forward primer for ABCG2-7
                           organism = synthetic construct
SEQUENCE: 93
tggcagtgca ggtttctctc                                                 20

SEQ ID NO: 94              moltype = DNA   length = 20
FEATURE                    Location/Qualifiers
source                     1..20
                           mol_type = other DNA
                           note = Sequence of reverse primer for ABCG2-7
                           organism = synthetic construct
SEQUENCE: 94
gtttcatgtt ggccaggctg                                                 20

SEQ ID NO: 95              moltype = DNA   length = 20
FEATURE                    Location/Qualifiers
source                     1..20
                           mol_type = other DNA
                           note = Sequence of forward primer for ABCG2-11
                           organism = synthetic construct
SEQUENCE: 95
aggccacgtg attcttccac                                                 20

SEQ ID NO: 96              moltype = DNA   length = 22
FEATURE                    Location/Qualifiers
source                     1..22
                           mol_type = other DNA
                           note = Sequence of reverse primer for ABCG2-11
                           organism = synthetic construct
SEQUENCE: 96
```

```
aggctccttt aaggaacagt gg                                                22

SEQ ID NO: 97           moltype = DNA   length = 20
FEATURE                 Location/Qualifiers
source                  1..20
                        mol_type = other DNA
                        note = Sequence of forward primer for ABCG2-13
                        organism = synthetic construct
SEQUENCE: 97
agcttgggaa tgcagtcaca                                                   20

SEQ ID NO: 98           moltype = DNA   length = 21
FEATURE                 Location/Qualifiers
source                  1..21
                        mol_type = other DNA
                        note = Sequence of reverse primer for ABCG2-13
                        organism = synthetic construct
SEQUENCE: 98
tggtagggac ttgaagaggg t                                                 21

SEQ ID NO: 99           moltype = DNA   length = 20
FEATURE                 Location/Qualifiers
source                  1..20
                        mol_type = other DNA
                        note = Sequence of forward primer for ABCG2-15
                        organism = synthetic construct
SEQUENCE: 99
ctctgacctg ctgctatggc                                                   20

SEQ ID NO: 100          moltype = DNA   length = 20
FEATURE                 Location/Qualifiers
source                  1..20
                        mol_type = other DNA
                        note = Sequence of reverse primer for ABCG2-15
                        organism = synthetic construct
SEQUENCE: 100
acaacattgg agaccgaggg                                                   20

SEQ ID NO: 101          moltype = DNA   length = 20
FEATURE                 Location/Qualifiers
source                  1..20
                        mol_type = other DNA
                        note = Sequence of forward primer for ABCG2-18
                        organism = synthetic construct
SEQUENCE: 101
agccaccaca ttgctaaact                                                   20

SEQ ID NO: 102          moltype = DNA   length = 20
FEATURE                 Location/Qualifiers
source                  1..20
                        mol_type = other DNA
                        note = Sequence of reverse primer for ABCG2-18
                        organism = synthetic construct
SEQUENCE: 102
tagccttacc tccctcaccc                                                   20

SEQ ID NO: 103          moltype = DNA   length = 22
FEATURE                 Location/Qualifiers
source                  1..22
                        mol_type = other DNA
                        note = Sequence of forward primer for ABCG2-25
                        organism = synthetic construct
SEQUENCE: 103
gccagtttct tggaaatagc ca                                                22

SEQ ID NO: 104          moltype = DNA   length = 20
FEATURE                 Location/Qualifiers
source                  1..20
                        mol_type = other DNA
                        note = Sequence of reverse primer for ABCG2-25
                        organism = synthetic construct
SEQUENCE: 104
ggaaacacca atggcttccc                                                   20

SEQ ID NO: 105          moltype = DNA   length = 20
FEATURE                 Location/Qualifiers
source                  1..20
                        mol_type = other DNA
                        note = Sequence of forward primer for AQP1-1
```

```
                                  organism = synthetic construct
SEQUENCE: 105
ccggccctat aaataggccc                                                    20

SEQ ID NO: 106          moltype = DNA   length = 20
FEATURE                 Location/Qualifiers
source                  1..20
                        mol_type = other DNA
                        note = Sequence of reverse primer for AQP1-1
                        organism = synthetic construct
SEQUENCE: 106
cgacaccttc acgttgtcct                                                    20

SEQ ID NO: 107          moltype = DNA   length = 20
FEATURE                 Location/Qualifiers
source                  1..20
                        mol_type = other DNA
                        note = Sequence of forward primer for AQP1-3
                        organism = synthetic construct
SEQUENCE: 107
ccgtgccctc atgtacatca                                                    20

SEQ ID NO: 108          moltype = DNA   length = 20
FEATURE                 Location/Qualifiers
source                  1..20
                        mol_type = other DNA
                        note = Sequence of reverse primer for AQP1-3
                        organism = synthetic construct
SEQUENCE: 108
tctctacgtg acctccagca                                                    20

SEQ ID NO: 109          moltype = DNA   length = 20
FEATURE                 Location/Qualifiers
source                  1..20
                        mol_type = other DNA
                        note = Sequence of forward primer for RhD-3
                        organism = synthetic construct
SEQUENCE: 109
aagatctgac cgtgatggcg                                                    20

SEQ ID NO: 110          moltype = DNA   length = 20
FEATURE                 Location/Qualifiers
source                  1..20
                        mol_type = other DNA
                        note = Sequence of reverse primer for RhD-3
                        organism = synthetic construct
SEQUENCE: 110
gaacctgtcc tttcggggtc                                                    20

SEQ ID NO: 111          moltype = DNA   length = 21
FEATURE                 Location/Qualifiers
source                  1..21
                        mol_type = other DNA
                        note = Sequence of forward primer for RhD-4
                        organism = synthetic construct
SEQUENCE: 111
ttctcagtcg tcctggctct c                                                  21

SEQ ID NO: 112          moltype = DNA   length = 21
FEATURE                 Location/Qualifiers
source                  1..21
                        mol_type = other DNA
                        note = Sequence of reverse primer for RhD-4
                        organism = synthetic construct
SEQUENCE: 112
ttcaaaaccc tggaaacccc a                                                  21

SEQ ID NO: 113          moltype = DNA   length = 20
FEATURE                 Location/Qualifiers
source                  1..20
                        mol_type = other DNA
                        note = Sequence of forward primer for RhD-5
                        organism = synthetic construct
SEQUENCE: 113
gaggatgccg acactcactg                                                    20

SEQ ID NO: 114          moltype = DNA   length = 20
FEATURE                 Location/Qualifiers
source                  1..20
```

```
                            mol_type = other DNA
                            note = Sequence of reverse primer for RhD-5
                            organism = synthetic construct
SEQUENCE: 114
tcagcccaag taggagacca                                                    20

SEQ ID NO: 115              moltype = DNA   length = 20
FEATURE                     Location/Qualifiers
source                      1..20
                            mol_type = other DNA
                            note = Sequence of forward primer for RhD-8
                            organism = synthetic construct
SEQUENCE: 115
gcttccttta cccacacgct                                                    20

SEQ ID NO: 116              moltype = DNA   length = 20
FEATURE                     Location/Qualifiers
source                      1..20
                            mol_type = other DNA
                            note = Sequence of reverse primer for RhD-8
                            organism = synthetic construct
SEQUENCE: 116
ccttcagcca aagcagagga                                                    20

SEQ ID NO: 117              moltype = DNA   length = 20
FEATURE                     Location/Qualifiers
source                      1..20
                            mol_type = other DNA
                            note = Sequence of forward primer for RhD-10
                            organism = synthetic construct
SEQUENCE: 117
ctgatgccca agtgaccacc                                                    20

SEQ ID NO: 118              moltype = DNA   length = 20
FEATURE                     Location/Qualifiers
source                      1..20
                            mol_type = other DNA
                            note = Sequence of reverse primer for RhD-10
                            organism = synthetic construct
SEQUENCE: 118
aggagatggg gcacatagac                                                    20

SEQ ID NO: 119              moltype = DNA   length = 20
FEATURE                     Location/Qualifiers
source                      1..20
                            mol_type = other DNA
                            note = Sequence of forward primer for RhCE-14
                            organism = synthetic construct
SEQUENCE: 119
gaaaggtggc ctcacactga                                                    20

SEQ ID NO: 120              moltype = DNA   length = 20
FEATURE                     Location/Qualifiers
source                      1..20
                            mol_type = other DNA
                            note = Sequence of reverse primer for RhCE-14
                            organism = synthetic construct
SEQUENCE: 120
cctggcaatg gcactactga                                                    20

SEQ ID NO: 121              moltype = DNA   length = 21
FEATURE                     Location/Qualifiers
source                      1..21
                            mol_type = other DNA
                            note = Sequence of forward primer for RhCE-18
                            organism = synthetic construct
SEQUENCE: 121
ctcagcccaa gtatgagacc a                                                  21

SEQ ID NO: 122              moltype = DNA   length = 21
FEATURE                     Location/Qualifiers
source                      1..21
                            mol_type = other DNA
                            note = Sequence of reverse primer for RhCE-18
                            organism = synthetic construct
SEQUENCE: 122
tttctccaag gaccatcagg g                                                  21

SEQ ID NO: 123              moltype = DNA   length = 20
```

```
FEATURE                    Location/Qualifiers
source                     1..20
                           mol_type = other DNA
                           note = Sequence of forward primer for FY-1
                           organism = synthetic construct
SEQUENCE: 123
ccatcctggt ctcttggtgc                                                    20

SEQ ID NO: 124             moltype = DNA   length = 20
FEATURE                    Location/Qualifiers
source                     1..20
                           mol_type = other DNA
                           note = Sequence of reverse primer for FY-1
                           organism = synthetic construct
SEQUENCE: 124
aggccatcag agttacaccg                                                    20

SEQ ID NO: 125             moltype = DNA   length = 20
FEATURE                    Location/Qualifiers
source                     1..20
                           mol_type = other DNA
                           note = Sequence of forward primer for FY-3
                           organism = synthetic construct
SEQUENCE: 125
gcactgccct tcttcatcct                                                    20

SEQ ID NO: 126             moltype = DNA   length = 20
FEATURE                    Location/Qualifiers
source                     1..20
                           mol_type = other DNA
                           note = Sequence of reverse primer for FY-3
                           organism = synthetic construct
SEQUENCE: 126
gctgagccat accagacaca                                                    20

SEQ ID NO: 127             moltype = DNA   length = 20
FEATURE                    Location/Qualifiers
source                     1..20
                           mol_type = other DNA
                           note = Sequence of forward primer for FY-5
                           organism = synthetic construct
SEQUENCE: 127
cactgtagcc tgtcttgcca                                                    20

SEQ ID NO: 128             moltype = DNA   length = 20
FEATURE                    Location/Qualifiers
source                     1..20
                           mol_type = other DNA
                           note = Sequence of reverse primer for FY-5
                           organism = synthetic construct
SEQUENCE: 128
aaaattgcca gggcttctgc                                                    20

SEQ ID NO: 129             moltype = DNA   length = 21
FEATURE                    Location/Qualifiers
source                     1..21
                           mol_type = other DNA
                           note = Sequence of forward primer for SLC35C1-1
                           organism = synthetic construct
SEQUENCE: 129
aacctctgcc tcaagtacgt c                                                  21

SEQ ID NO: 130             moltype = DNA   length = 20
FEATURE                    Location/Qualifiers
source                     1..20
                           mol_type = other DNA
                           note = Sequence of reverse primer for SLC35C1-1
                           organism = synthetic construct
SEQUENCE: 130
tgaccactct atcccccgtg                                                    20

SEQ ID NO: 131             moltype = DNA   length = 20
FEATURE                    Location/Qualifiers
source                     1..20
                           mol_type = other DNA
                           note = Sequence of forward primer for DI-2
                           organism = synthetic construct
SEQUENCE: 131
atgaagacca gcagagcagg                                                    20
```

```
SEQ ID NO: 132          moltype = DNA   length = 20
FEATURE                 Location/Qualifiers
source                  1..20
                        mol_type = other DNA
                        note = Sequence of reverse primer for DI-2
                        organism = synthetic construct
SEQUENCE: 132
agttcccaag tgcctccaac                                                   20

SEQ ID NO: 133          moltype = DNA   length = 20
FEATURE                 Location/Qualifiers
source                  1..20
                        mol_type = other DNA
                        note = Sequence of forward primer for JK-1
                        organism = synthetic construct
SEQUENCE: 133
tggctaatct ggagggctct                                                   20

SEQ ID NO: 134          moltype = DNA   length = 21
FEATURE                 Location/Qualifiers
source                  1..21
                        mol_type = other DNA
                        note = Sequence of reverse primer for JK-1
                        organism = synthetic construct
SEQUENCE: 134
acctttaagc tggttggcaa g                                                 21

SEQ ID NO: 135          moltype = DNA   length = 20
FEATURE                 Location/Qualifiers
source                  1..20
                        mol_type = other DNA
                        note = Sequence of forward primer for JK-4
                        organism = synthetic construct
SEQUENCE: 135
cagcctgctt tgtcacatgc                                                   20

SEQ ID NO: 136          moltype = DNA   length = 20
FEATURE                 Location/Qualifiers
source                  1..20
                        mol_type = other DNA
                        note = Sequence of reverse primer for JK-4
                        organism = synthetic construct
SEQUENCE: 136
gcgaatgtga gaagccagtg                                                   20

SEQ ID NO: 137          moltype = DNA   length = 22
FEATURE                 Location/Qualifiers
source                  1..22
                        mol_type = other DNA
                        note = Sequence of forward primer for JK-7
                        organism = synthetic construct
SEQUENCE: 137
gtaatcaggg cactgtgcat tc                                                22

SEQ ID NO: 138          moltype = DNA   length = 21
FEATURE                 Location/Qualifiers
source                  1..21
                        mol_type = other DNA
                        note = Sequence of reverse primer for JK-7
                        organism = synthetic construct
SEQUENCE: 138
tggacttcag gagcatttcc c                                                 21

SEQ ID NO: 139          moltype = DNA   length = 20
FEATURE                 Location/Qualifiers
source                  1..20
                        mol_type = other DNA
                        note = Sequence of forward primer for FUT6-2
                        organism = synthetic construct
SEQUENCE: 139
tcgtagttgc ttctgctggg                                                   20

SEQ ID NO: 140          moltype = DNA   length = 20
FEATURE                 Location/Qualifiers
source                  1..20
                        mol_type = other DNA
                        note = Sequence of reverse primer for FUT6-2
                        organism = synthetic construct
```

```
SEQUENCE: 140
ggaaccatga tggagacgct                                              20

SEQ ID NO: 141         moltype = DNA  length = 20
FEATURE                Location/Qualifiers
source                 1..20
                       mol_type = other DNA
                       note = Sequence of forward primer for FUT6-3
                       organism = synthetic construct
SEQUENCE: 141
gtcttggccg agaggttgag                                              20

SEQ ID NO: 142         moltype = DNA  length = 20
FEATURE                Location/Qualifiers
source                 1..20
                       mol_type = other DNA
                       note = Sequence of reverse primer for FUT6-3
                       organism = synthetic construct
SEQUENCE: 142
tcatgtacaa ccccagtgcc                                              20

SEQ ID NO: 143         moltype = DNA  length = 22
FEATURE                Location/Qualifiers
source                 1..22
                       mol_type = other DNA
                       note = Sequence of forward primer for FUT6-5
                       organism = synthetic construct
SEQUENCE: 143
atgggtttgt taaaaggcca cg                                           22

SEQ ID NO: 144         moltype = DNA  length = 21
FEATURE                Location/Qualifiers
source                 1..21
                       mol_type = other DNA
                       note = Sequence of reverse primer for FUT6-5
                       organism = synthetic construct
SEQUENCE: 144
tctccccact tcccagatac t                                            21

SEQ ID NO: 145         moltype = DNA  length = 19
FEATURE                Location/Qualifiers
source                 1..19
                       mol_type = other DNA
                       note = Sequence of forward primer for FUT3-2
                       organism = synthetic construct
SEQUENCE: 145
tggtccttgt ccagctcct                                               19

SEQ ID NO: 146         moltype = DNA  length = 20
FEATURE                Location/Qualifiers
source                 1..20
                       mol_type = other DNA
                       note = Sequence of reverse primer for FUT3-2
                       organism = synthetic construct
SEQUENCE: 146
ccaaggggac catgatggag                                              20

SEQ ID NO: 147         moltype = DNA  length = 20
FEATURE                Location/Qualifiers
source                 1..20
                       mol_type = other DNA
                       note = Sequence of forward primer for FUT3-4
                       organism = synthetic construct
SEQUENCE: 147
ctgagtccgg cttccagttg                                              20

SEQ ID NO: 148         moltype = DNA  length = 20
FEATURE                Location/Qualifiers
source                 1..20
                       mol_type = other DNA
                       note = Sequence of reverse primer for FUT3-4
                       organism = synthetic construct
SEQUENCE: 148
ccaaccctaa gtcacgcctc                                              20

SEQ ID NO: 149         moltype = DNA  length = 20
FEATURE                Location/Qualifiers
source                 1..20
                       mol_type = other DNA
```

```
                    note = Sequence of forward primer for FUT3-6
                    organism = synthetic construct
SEQUENCE: 149
tggaaaggcc atgtccgtag                                              20

SEQ ID NO: 150      moltype = DNA  length = 20
FEATURE             Location/Qualifiers
source              1..20
                    mol_type = other DNA
                    note = Sequence of reverse primer for FUT3-6
                    organism = synthetic construct
SEQUENCE: 150
actctgaccc atggatcccc                                              20

SEQ ID NO: 151      moltype = DNA  length = 20
FEATURE             Location/Qualifiers
source              1..20
                    mol_type = other DNA
                    note = Sequence of forward primer for KLF1-2
                    organism = synthetic construct
SEQUENCE: 151
cctctgcaac ccttcttccc                                              20

SEQ ID NO: 152      moltype = DNA  length = 20
FEATURE             Location/Qualifiers
source              1..20
                    mol_type = other DNA
                    note = Sequence of reverse primer for KLF1-2
                    organism = synthetic construct
SEQUENCE: 152
gactgcagag gatccaggtg                                              20

SEQ ID NO: 153      moltype = DNA  length = 20
FEATURE             Location/Qualifiers
source              1..20
                    mol_type = other DNA
                    note = Sequence of forward primer for KLF1-5
                    organism = synthetic construct
SEQUENCE: 153
ggaagtagcc acccgaggag                                              20

SEQ ID NO: 154      moltype = DNA  length = 20
FEATURE             Location/Qualifiers
source              1..20
                    mol_type = other DNA
                    note = Sequence of reverse primer for KLF1-5
                    organism = synthetic construct
SEQUENCE: 154
cgagactctg ggcgcatatg                                              20

SEQ ID NO: 155      moltype = DNA  length = 20
FEATURE             Location/Qualifiers
source              1..20
                    mol_type = other DNA
                    note = Sequence of forward primer for KLF1-7
                    organism = synthetic construct
SEQUENCE: 155
gaggagatcc aggtcccagg                                              20

SEQ ID NO: 156      moltype = DNA  length = 20
FEATURE             Location/Qualifiers
source              1..20
                    mol_type = other DNA
                    note = Sequence of reverse primer for KLF1-7
                    organism = synthetic construct
SEQUENCE: 156
gacaggcaaa caagacccct                                              20

SEQ ID NO: 157      moltype = DNA  length = 20
FEATURE             Location/Qualifiers
source              1..20
                    mol_type = other DNA
                    note = Sequence of forward primer for LU-1
                    organism = synthetic construct
SEQUENCE: 157
agctcagttg ctctcttgca                                              20

SEQ ID NO: 158      moltype = DNA  length = 20
FEATURE             Location/Qualifiers
```

| | | |
|---|---|---|
| source | 1..20<br>mol_type = other DNA<br>note = Sequence of reverse primer for LU-1<br>organism = synthetic construct | |
| SEQUENCE: 158<br>aacaaggagt gtggcttggt | | 20 |
| SEQ ID NO: 159<br>FEATURE<br>source | moltype = DNA  length = 20<br>Location/Qualifiers<br>1..20<br>mol_type = other DNA<br>note = Sequence of forward primer for LU-5<br>organism = synthetic construct | |
| SEQUENCE: 159<br>cgacttcaga gtcccagctc | | 20 |
| SEQ ID NO: 160<br>FEATURE<br>source | moltype = DNA  length = 19<br>Location/Qualifiers<br>1..19<br>mol_type = other DNA<br>note = Sequence of reverse primer for LU-5<br>organism = synthetic construct | |
| SEQUENCE: 160<br>gctgctcacc tgggttcat | | 19 |
| SEQ ID NO: 161<br>FEATURE<br>source | moltype = DNA  length = 20<br>Location/Qualifiers<br>1..20<br>mol_type = other DNA<br>note = Sequence of forward primer for LU-8<br>organism = synthetic construct | |
| SEQUENCE: 161<br>ccatgctgtc gctcagttct | | 20 |
| SEQ ID NO: 162<br>FEATURE<br>source | moltype = DNA  length = 20<br>Location/Qualifiers<br>1..20<br>mol_type = other DNA<br>note = Sequence of reverse primer for LU-8<br>organism = synthetic construct | |
| SEQUENCE: 162<br>cgagcagaag atggagtccc | | 20 |
| SEQ ID NO: 163<br>FEATURE<br>source | moltype = DNA  length = 20<br>Location/Qualifiers<br>1..20<br>mol_type = other DNA<br>note = Sequence of forward primer for LU-10<br>organism = synthetic construct | |
| SEQUENCE: 163<br>ctgatcggag cctccatagc | | 20 |
| SEQ ID NO: 164<br>FEATURE<br>source | moltype = DNA  length = 20<br>Location/Qualifiers<br>1..20<br>mol_type = other DNA<br>note = Sequence of reverse primer for LU-10<br>organism = synthetic construct | |
| SEQUENCE: 164<br>ctcactgcag ggacaggatg | | 20 |
| SEQ ID NO: 165<br>FEATURE<br>source | moltype = DNA  length = 20<br>Location/Qualifiers<br>1..20<br>mol_type = other DNA<br>note = Sequence of forward primer for FUT2-2<br>organism = synthetic construct | |
| SEQUENCE: 165<br>cgatcaatgc aataggccgc | | 20 |
| SEQ ID NO: 166<br>FEATURE<br>source | moltype = DNA  length = 20<br>Location/Qualifiers<br>1..20<br>mol_type = other DNA<br>note = Sequence of reverse primer for FUT2-2<br>organism = synthetic construct | |
| SEQUENCE: 166<br>gggatgtggc ggtattcctc | | 20 |

-continued

```
SEQ ID NO: 167             moltype = DNA  length = 20
FEATURE                    Location/Qualifiers
source                     1..20
                           mol_type = other DNA
                           note = Sequence of forward primer for FUT2-4
                           organism = synthetic construct
SEQUENCE: 167
gaggaggccc agaagttcct                                                  20

SEQ ID NO: 168             moltype = DNA  length = 20
FEATURE                    Location/Qualifiers
source                     1..20
                           mol_type = other DNA
                           note = Sequence of reverse primer for FUT2-4
                           organism = synthetic construct
SEQUENCE: 168
cagcaaacac cacatcaccg                                                  20

SEQ ID NO: 169             moltype = DNA  length = 20
FEATURE                    Location/Qualifiers
source                     1..20
                           mol_type = other DNA
                           note = Sequence of forward primer for FUT1-2
                           organism = synthetic construct
SEQUENCE: 169
cagagtctgg cagggtgaag                                                  20

SEQ ID NO: 170             moltype = DNA  length = 20
FEATURE                    Location/Qualifiers
source                     1..20
                           mol_type = other DNA
                           note = Sequence of reverse primer for FUT1-2
                           organism = synthetic construct
SEQUENCE: 170
ttttcgtggt caccagcaac                                                  20

SEQ ID NO: 171             moltype = DNA  length = 19
FEATURE                    Location/Qualifiers
source                     1..19
                           mol_type = other DNA
                           note = Sequence of forward primer for FUT1-5
                           organism = synthetic construct
SEQUENCE: 171
cacactctgc gcctcttcc                                                   19

SEQ ID NO: 172             moltype = DNA  length = 20
FEATURE                    Location/Qualifiers
source                     1..20
                           mol_type = other DNA
                           note = Sequence of reverse primer for FUT1-5
                           organism = synthetic construct
SEQUENCE: 172
tttatcctgc ctgccatgca                                                  20

SEQ ID NO: 173             moltype = DNA  length = 20
FEATURE                    Location/Qualifiers
source                     1..20
                           mol_type = other DNA
                           note = Sequence of forward primer for FUT1-7
                           organism = synthetic construct
SEQUENCE: 173
cgtggcatac tgtcccatct                                                  20

SEQ ID NO: 174             moltype = DNA  length = 20
FEATURE                    Location/Qualifiers
source                     1..20
                           mol_type = other DNA
                           note = Sequence of reverse primer for FUT1-7
                           organism = synthetic construct
SEQUENCE: 174
ctggccttcc tgctagtctg                                                  20

SEQ ID NO: 175             moltype = DNA  length = 20
FEATURE                    Location/Qualifiers
source                     1..20
                           mol_type = other DNA
                           note = Sequence of forward primer for A4GALT-4
                           organism = synthetic construct
SEQUENCE: 175
```

```
catgagtgcg atcctggagg                                          20

SEQ ID NO: 176        moltype = DNA  length = 20
FEATURE               Location/Qualifiers
source                1..20
                      mol_type = other DNA
                      note = Sequence of reverse primer for A4GALT-4
                      organism = synthetic construct
SEQUENCE: 176
ttcatgtgct cggtggagtc                                          20

SEQ ID NO: 177        moltype = DNA  length = 18
FEATURE               Location/Qualifiers
source                1..18
                      mol_type = other DNA
                      note = Sequence of forward primer for A4GALT-7
                      organism = synthetic construct
SEQUENCE: 177
cctcctcccc actgcgag                                            18

SEQ ID NO: 178        moltype = DNA  length = 18
FEATURE               Location/Qualifiers
source                1..18
                      mol_type = other DNA
                      note = Sequence of reverse primer for A4GALT-7
                      organism = synthetic construct
SEQUENCE: 178
cgcaagggct ctggggac                                            18

SEQ ID NO: 179        moltype = DNA  length = 22
FEATURE               Location/Qualifiers
source                1..22
                      mol_type = other DNA
                      note = Sequence of forward primer for B3GALNT1-4
                      organism = synthetic construct
SEQUENCE: 179
tcagtgtctg tcttcattac gt                                       22

SEQ ID NO: 180        moltype = DNA  length = 20
FEATURE               Location/Qualifiers
source                1..20
                      mol_type = other DNA
                      note = Sequence of reverse primer for B3GALNT1-4
                      organism = synthetic construct
SEQUENCE: 180
ccaggcaggc cattagagtt                                          20

SEQ ID NO: 181        moltype = DNA  length = 22
FEATURE               Location/Qualifiers
source                1..22
                      mol_type = other DNA
                      note = Sequence of forward primer for GYPA-2
                      organism = synthetic construct
SEQUENCE: 181
ctcctagagc tgttcacact gg                                       22

SEQ ID NO: 182        moltype = DNA  length = 22
FEATURE               Location/Qualifiers
source                1..22
                      mol_type = other DNA
                      note = Sequence of reverse primer for GYPA-2
                      organism = synthetic construct
SEQUENCE: 182
aggcaaggtg atgttatgct ga                                       22

SEQ ID NO: 183        moltype = DNA  length = 20
FEATURE               Location/Qualifiers
source                1..20
                      mol_type = other DNA
                      note = Sequence of forward primer for GYPA-4
                      organism = synthetic construct
SEQUENCE: 183
gcagtgacag gtcccctaaa                                          20

SEQ ID NO: 184        moltype = DNA  length = 20
FEATURE               Location/Qualifiers
source                1..20
                      mol_type = other DNA
                      note = Sequence of reverse primer for GYPA-4
```

```
                              organism = synthetic construct
SEQUENCE: 184
ctgctcagtc acctcgttct                                                 20

SEQ ID NO: 185        moltype = DNA  length = 20
FEATURE               Location/Qualifiers
source                1..20
                      mol_type = other DNA
                      note = Sequence of forward primer for GYPA-6
                      organism = synthetic construct
SEQUENCE: 185
gcagtgacag gtcccctaaa                                                 20

SEQ ID NO: 186        moltype = DNA  length = 20
FEATURE               Location/Qualifiers
source                1..20
                      mol_type = other DNA
                      note = Sequence of reverse primer for GYPA-6
                      organism = synthetic construct
SEQUENCE: 186
ttatggtccg ctcagtcacc                                                 20

SEQ ID NO: 187        moltype = DNA  length = 21
FEATURE               Location/Qualifiers
source                1..21
                      mol_type = other DNA
                      note = Sequence of forward primer for YT-2
                      organism = synthetic construct
SEQUENCE: 187
acactctgga aggttgtagc g                                               21

SEQ ID NO: 188        moltype = DNA  length = 20
FEATURE               Location/Qualifiers
source                1..20
                      mol_type = other DNA
                      note = Sequence of reverse primer for YT-2
                      organism = synthetic construct
SEQUENCE: 188
tccttctcct cctcctctgg                                                 20

SEQ ID NO: 189        moltype = DNA  length = 20
FEATURE               Location/Qualifiers
source                1..20
                      mol_type = other DNA
                      note = Sequence of forward primer for KEL-6
                      organism = synthetic construct
SEQUENCE: 189
catacctgtg ttgggggtga                                                 20

SEQ ID NO: 190        moltype = DNA  length = 21
FEATURE               Location/Qualifiers
source                1..21
                      mol_type = other DNA
                      note = Sequence of reverse primer for KEL-6
                      organism = synthetic construct
SEQUENCE: 190
tggtcccatt ggtgtttgtc a                                               21

SEQ ID NO: 191        moltype = DNA  length = 20
FEATURE               Location/Qualifiers
source                1..20
                      mol_type = other DNA
                      note = Sequence of forward primer for KEL-9
                      organism = synthetic construct
SEQUENCE: 191
tgcccaattc cccaatcaca                                                 20

SEQ ID NO: 192        moltype = DNA  length = 20
FEATURE               Location/Qualifiers
source                1..20
                      mol_type = other DNA
                      note = Sequence of reverse primer for KEL-9
                      organism = synthetic construct
SEQUENCE: 192
tcctgaacag gagccactca                                                 20

SEQ ID NO: 193        moltype = DNA  length = 20
FEATURE               Location/Qualifiers
source                1..20
```

```
                            mol_type = other DNA
                            note = Sequence of forward primer for KEL-13
                            organism = synthetic construct
SEQUENCE: 193
gtctcctccc agcaaggttc                                                   20

SEQ ID NO: 194              moltype = DNA   length = 20
FEATURE                     Location/Qualifiers
source                      1..20
                            mol_type = other DNA
                            note = Sequence of reverse primer for KEL-13
                            organism = synthetic construct
SEQUENCE: 194
ccagtctctc ttgtgcccag                                                   20

SEQ ID NO: 195              moltype = DNA   length = 20
FEATURE                     Location/Qualifiers
source                      1..20
                            mol_type = other DNA
                            note = Sequence of forward primer for FUT7-7
                            organism = synthetic construct
SEQUENCE: 195
gtgggtgtgg ctaggagact                                                   20

SEQ ID NO: 196              moltype = DNA   length = 20
FEATURE                     Location/Qualifiers
source                      1..20
                            mol_type = other DNA
                            note = Sequence of reverse primer for FUT7-7
                            organism = synthetic construct
SEQUENCE: 196
tcaccatcct tgtctggcac                                                   20

SEQ ID NO: 197              moltype = DNA   length = 20
FEATURE                     Location/Qualifiers
source                      1..20
                            mol_type = other DNA
                            note = Sequence of forward primer for ART4-1
                            organism = synthetic construct
SEQUENCE: 197
tgctcaggtt cccagttgac                                                   20

SEQ ID NO: 198              moltype = DNA   length = 20
FEATURE                     Location/Qualifiers
source                      1..20
                            mol_type = other DNA
                            note = Sequence of reverse primer for ART4-1
                            organism = synthetic construct
SEQUENCE: 198
ctacacaggg gccaccattc                                                   20

SEQ ID NO: 199              moltype = DNA   length = 20
FEATURE                     Location/Qualifiers
source                      1..20
                            mol_type = other DNA
                            note = Sequence of forward primer for ART4-3
                            organism = synthetic construct
SEQUENCE: 199
agctggattg ctgaggtgag                                                   20

SEQ ID NO: 200              moltype = DNA   length = 20
FEATURE                     Location/Qualifiers
source                      1..20
                            mol_type = other DNA
                            note = Sequence of reverse primer for ART4-3
                            organism = synthetic construct
SEQUENCE: 200
aaaagcccac ttagcctggc                                                   20

SEQ ID NO: 201              moltype = DNA   length = 20
FEATURE                     Location/Qualifiers
source                      1..20
                            mol_type = other DNA
                            note = Sequence of forward primer for ART4-6
                            organism = synthetic construct
SEQUENCE: 201
cgggtgaatg ctctgttgga                                                   20

SEQ ID NO: 202              moltype = DNA   length = 20
```

-continued

| FEATURE | Location/Qualifiers |
|---|---|
| source | 1..20<br>mol_type = other DNA<br>note = Sequence of reverse primer for ART4-6<br>organism = synthetic construct |

SEQUENCE: 202
tcaggatgaa gctgcaaggg                                              20

| SEQ ID NO: 203 | moltype = DNA  length = 20 |
|---|---|
| FEATURE | Location/Qualifiers |
| source | 1..20<br>mol_type = other DNA<br>note = Sequence of forward primer for ABCG2-1<br>organism = synthetic construct |

SEQUENCE: 203
cacctgcatt ccttggctct                                              20

| SEQ ID NO: 204 | moltype = DNA  length = 20 |
|---|---|
| FEATURE | Location/Qualifiers |
| source | 1..20<br>mol_type = other DNA<br>note = Sequence of reverse primer for ABCG2-1<br>organism = synthetic construct |

SEQUENCE: 204
ctgacctcgt aatccacccg                                              20

| SEQ ID NO: 205 | moltype = DNA  length = 20 |
|---|---|
| FEATURE | Location/Qualifiers |
| source | 1..20<br>mol_type = other DNA<br>note = Sequence of forward primer for ABCG2-5<br>organism = synthetic construct |

SEQUENCE: 205
gtttgcacca gggcatcatt                                              20

| SEQ ID NO: 206 | moltype = DNA  length = 20 |
|---|---|
| FEATURE | Location/Qualifiers |
| source | 1..20<br>mol_type = other DNA<br>note = Sequence of reverse primer for ABCG2-5<br>organism = synthetic construct |

SEQUENCE: 206
gcctttggtt aagaccgagc                                              20

| SEQ ID NO: 207 | moltype = DNA  length = 20 |
|---|---|
| FEATURE | Location/Qualifiers |
| source | 1..20<br>mol_type = other DNA<br>note = Sequence of forward primer for ABCG2-8<br>organism = synthetic construct |

SEQUENCE: 207
atcttttggc ttccctgggc                                              20

| SEQ ID NO: 208 | moltype = DNA  length = 20 |
|---|---|
| FEATURE | Location/Qualifiers |
| source | 1..20<br>mol_type = other DNA<br>note = Sequence of reverse primer for ABCG2-8<br>organism = synthetic construct |

SEQUENCE: 208
cttgtccaac gtgcatgtgg                                              20

| SEQ ID NO: 209 | moltype = DNA  length = 20 |
|---|---|
| FEATURE | Location/Qualifiers |
| source | 1..20<br>mol_type = other DNA<br>note = Sequence of forward primer for ABCG2-10<br>organism = synthetic construct |

SEQUENCE: 209
cggggaagcc attggtgttt                                              20

| SEQ ID NO: 210 | moltype = DNA  length = 20 |
|---|---|
| FEATURE | Location/Qualifiers |
| source | 1..20<br>mol_type = other DNA<br>note = Sequence of reverse primer for ABCG2-10<br>organism = synthetic construct |

SEQUENCE: 210
agttgtgcct gtcttcccat                                              20

```
SEQ ID NO: 211           moltype = DNA  length = 22
FEATURE                  Location/Qualifiers
source                   1..22
                         mol_type = other DNA
                         note = Sequence of forward primer for ABCG2-14
                         organism = synthetic construct
SEQUENCE: 211
gcaaacacag ttcagactca cc                                              22

SEQ ID NO: 212           moltype = DNA  length = 20
FEATURE                  Location/Qualifiers
source                   1..20
                         mol_type = other DNA
                         note = Sequence of reverse primer for ABCG2-14
                         organism = synthetic construct
SEQUENCE: 212
tcccaaacat acggtgacct                                                 20

SEQ ID NO: 213           moltype = DNA  length = 20
FEATURE                  Location/Qualifiers
source                   1..20
                         mol_type = other DNA
                         note = Sequence of forward primer for ABCG2-16
                         organism = synthetic construct
SEQUENCE: 213
ggtgcaactg acttcaccca                                                 20

SEQ ID NO: 214           moltype = DNA  length = 21
FEATURE                  Location/Qualifiers
source                   1..21
                         mol_type = other DNA
                         note = Sequence of reverse primer for ABCG2-16
                         organism = synthetic construct
SEQUENCE: 214
aacagacaag tctagcctgc c                                               21

SEQ ID NO: 215           moltype = DNA  length = 20
FEATURE                  Location/Qualifiers
source                   1..20
                         mol_type = other DNA
                         note = Sequence of forward primer for ABCG2-19
                         organism = synthetic construct
SEQUENCE: 215
agtatcccaa ggcctcctga                                                 20

SEQ ID NO: 216           moltype = DNA  length = 22
FEATURE                  Location/Qualifiers
source                   1..22
                         mol_type = other DNA
                         note = Sequence of reverse primer for ABCG2-19
                         organism = synthetic construct
SEQUENCE: 216
caaagtcagg ctgaactaga gc                                              22

SEQ ID NO: 217           moltype = DNA  length = 20
FEATURE                  Location/Qualifiers
source                   1..20
                         mol_type = other DNA
                         note = Sequence of forward primer for ABCG2-21
                         organism = synthetic construct
SEQUENCE: 217
accttggagt ctgccacttt                                                 20

SEQ ID NO: 218           moltype = DNA  length = 22
FEATURE                  Location/Qualifiers
source                   1..22
                         mol_type = other DNA
                         note = Sequence of reverse primer for ABCG2-21
                         organism = synthetic construct
SEQUENCE: 218
aaggatgatg ttgtgatggg ca                                              22

SEQ ID NO: 219           moltype = DNA  length = 20
FEATURE                  Location/Qualifiers
source                   1..20
                         mol_type = other DNA
                         note = Sequence of forward primer for ABCG2-23
                         organism = synthetic construct
```

-continued

```
SEQUENCE: 219
tcagccaaag cacttaccca                                            20

SEQ ID NO: 220          moltype = DNA  length = 22
FEATURE                 Location/Qualifiers
source                  1..22
                        mol_type = other DNA
                        note = Sequence of reverse primer for ABCG2-23
                        organism = synthetic construct
SEQUENCE: 220
tatagcatgt gttggaggga aa                                         22

SEQ ID NO: 221          moltype = DNA  length = 20
FEATURE                 Location/Qualifiers
source                  1..20
                        mol_type = other DNA
                        note = Sequence of forward primer for AQP1-4
                        organism = synthetic construct
SEQUENCE: 221
ttctccctcc aacctctccc                                            20

SEQ ID NO: 222          moltype = DNA  length = 20
FEATURE                 Location/Qualifiers
source                  1..20
                        mol_type = other DNA
                        note = Sequence of reverse primer for AQP1-4
                        organism = synthetic construct
SEQUENCE: 222
ggtcaggctt accatgggac                                            20

SEQ ID NO: 223          moltype = DNA  length = 20
FEATURE                 Location/Qualifiers
source                  1..20
                        mol_type = other DNA
                        note = Sequence of forward primer for RhD-2
                        organism = synthetic construct
SEQUENCE: 223
aaatctcgtc tgcttccccc                                            20

SEQ ID NO: 224          moltype = DNA  length = 20
FEATURE                 Location/Qualifiers
source                  1..20
                        mol_type = other DNA
                        note = Sequence of reverse primer for RhD-2
                        organism = synthetic construct
SEQUENCE: 224
gatccagcca ccatcccaat                                            20

SEQ ID NO: 225          moltype = DNA  length = 20
FEATURE                 Location/Qualifiers
source                  1..20
                        mol_type = other DNA
                        note = Sequence of forward primer for RhD-7
                        organism = synthetic construct
SEQUENCE: 225
ctcgaggctc agacctttgg                                            20

SEQ ID NO: 226          moltype = DNA  length = 20
FEATURE                 Location/Qualifiers
source                  1..20
                        mol_type = other DNA
                        note = Sequence of reverse primer for RhD-7
                        organism = synthetic construct
SEQUENCE: 226
ttagacccaa gtgctgccca                                            20

SEQ ID NO: 227          moltype = DNA  length = 24
FEATURE                 Location/Qualifiers
source                  1..24
                        mol_type = other DNA
                        note = Sequence of forward primer for RhD-11
                        organism = synthetic construct
SEQUENCE: 227
tgagattaaa aatcctgtgc tcca                                       24

SEQ ID NO: 228          moltype = DNA  length = 20
FEATURE                 Location/Qualifiers
source                  1..20
                        mol_type = other DNA
```

-continued

```
                        note = Sequence of reverse primer for RhD-11
                        organism = synthetic construct
SEQUENCE: 228
gttcctcctg caatgctcct                                                    20

SEQ ID NO: 229          moltype = DNA   length = 22
FEATURE                 Location/Qualifiers
source                  1..22
                        mol_type = other DNA
                        note = Sequence of forward primer for RhCE-13
                        organism = synthetic construct
SEQUENCE: 229
tctgtctctg accttgtttc at                                                 22

SEQ ID NO: 230          moltype = DNA   length = 22
FEATURE                 Location/Qualifiers
source                  1..22
                        mol_type = other DNA
                        note = Sequence of reverse primer for RhCE-13
                        organism = synthetic construct
SEQUENCE: 230
ggctgtttca agagatcaag cc                                                 22

SEQ ID NO: 231          moltype = DNA   length = 20
FEATURE                 Location/Qualifiers
source                  1..20
                        mol_type = other DNA
                        note = Sequence of forward primer for RhCE-16
                        organism = synthetic construct
SEQUENCE: 231
cttcagccaa agcagagagc                                                    20

SEQ ID NO: 232          moltype = DNA   length = 20
FEATURE                 Location/Qualifiers
source                  1..20
                        mol_type = other DNA
                        note = Sequence of reverse primer for RhCE-16
                        organism = synthetic construct
SEQUENCE: 232
gctggtcact tgcagcaaga                                                    20

SEQ ID NO: 233          moltype = DNA   length = 22
FEATURE                 Location/Qualifiers
source                  1..22
                        mol_type = other DNA
                        note = Sequence of forward primer for RhCE-19
                        organism = synthetic construct
SEQUENCE: 233
aatggagctt ttggccctttt tc                                                22

SEQ ID NO: 234          moltype = DNA   length = 22
FEATURE                 Location/Qualifiers
source                  1..22
                        mol_type = other DNA
                        note = Sequence of reverse primer for RhCE-19
                        organism = synthetic construct
SEQUENCE: 234
tcagtcatcc tggctctcct tc                                                 22

SEQ ID NO: 235          moltype = DNA   length = 20
FEATURE                 Location/Qualifiers
source                  1..20
                        mol_type = other DNA
                        note = Sequence of forward primer for RhCE-21
                        organism = synthetic construct
SEQUENCE: 235
gatccagcca ccatcccaat                                                    20

SEQ ID NO: 236          moltype = DNA   length = 20
FEATURE                 Location/Qualifiers
source                  1..20
                        mol_type = other DNA
                        note = Sequence of reverse primer for RhCE-21
                        organism = synthetic construct
SEQUENCE: 236
aaatctcgtc tgcttccccc                                                    20

SEQ ID NO: 237          moltype = DNA   length = 20
FEATURE                 Location/Qualifiers
```

```
source                  1..20
                        mol_type = other DNA
                        note = Sequence of forward primer for FY-2
                        organism = synthetic construct
SEQUENCE: 237
atggcctcct ctgggtatgt                                                    20

SEQ ID NO: 238          moltype = DNA  length = 20
FEATURE                 Location/Qualifiers
source                  1..20
                        mol_type = other DNA
                        note = Sequence of reverse primer for FY-2
                        organism = synthetic construct
SEQUENCE: 238
agcatgaaga ggacagtgct                                                    20

SEQ ID NO: 239          moltype = DNA  length = 18
FEATURE                 Location/Qualifiers
source                  1..18
                        mol_type = other DNA
                        note = Sequence of forward primer for FY-4
                        organism = synthetic construct
SEQUENCE: 239
tcttccgctg gcagctct                                                      18

SEQ ID NO: 240          moltype = DNA  length = 20
FEATURE                 Location/Qualifiers
source                  1..20
                        mol_type = other DNA
                        note = Sequence of reverse primer for FY-4
                        organism = synthetic construct
SEQUENCE: 240
ccactcccca aattcccaca                                                    20

SEQ ID NO: 241          moltype = DNA  length = 20
FEATURE                 Location/Qualifiers
source                  1..20
                        mol_type = other DNA
                        note = Sequence of forward primer for SLC35C1-3
                        organism = synthetic construct
SEQUENCE: 241
catcggctac gtgacaggac                                                    20

SEQ ID NO: 242          moltype = DNA  length = 20
FEATURE                 Location/Qualifiers
source                  1..20
                        mol_type = other DNA
                        note = Sequence of reverse primer for SLC35C1-3
                        organism = synthetic construct
SEQUENCE: 242
tcttctcgct gtctttgggg                                                    20

SEQ ID NO: 243          moltype = DNA  length = 20
FEATURE                 Location/Qualifiers
source                  1..20
                        mol_type = other DNA
                        note = Sequence of forward primer for DI-4
                        organism = synthetic construct
SEQUENCE: 243
caacaccacc agcaggatga                                                    20

SEQ ID NO: 244          moltype = DNA  length = 20
FEATURE                 Location/Qualifiers
source                  1..20
                        mol_type = other DNA
                        note = Sequence of reverse primer for DI-4
                        organism = synthetic construct
SEQUENCE: 244
ccctgctggt gtttgaggaa                                                    20

SEQ ID NO: 245          moltype = DNA  length = 20
FEATURE                 Location/Qualifiers
source                  1..20
                        mol_type = other DNA
                        note = Sequence of forward primer for JK-2
                        organism = synthetic construct
SEQUENCE: 245
cttccagaca aacccgtggt                                                    20
```

```
SEQ ID NO: 246          moltype = DNA   length = 20
FEATURE                 Location/Qualifiers
source                  1..20
                        mol_type = other DNA
                        note = Sequence of reverse primer for JK-2
                        organism = synthetic construct
SEQUENCE: 246
tgcccacagt aactggtcag                                                  20

SEQ ID NO: 247          moltype = DNA   length = 20
FEATURE                 Location/Qualifiers
source                  1..20
                        mol_type = other DNA
                        note = Sequence of forward primer for JK-5
                        organism = synthetic construct
SEQUENCE: 247
accagtggga gttggtcaga                                                  20

SEQ ID NO: 248          moltype = DNA   length = 20
FEATURE                 Location/Qualifiers
source                  1..20
                        mol_type = other DNA
                        note = Sequence of reverse primer for JK-5
                        organism = synthetic construct
SEQUENCE: 248
cccattggtc cctaggaagc                                                  20

SEQ ID NO: 249          moltype = DNA   length = 20
FEATURE                 Location/Qualifiers
source                  1..20
                        mol_type = other DNA
                        note = Sequence of forward primer for FUT6-4
                        organism = synthetic construct
SEQUENCE: 249
ttggggactc catgctgaac                                                  20

SEQ ID NO: 250          moltype = DNA   length = 20
FEATURE                 Location/Qualifiers
source                  1..20
                        mol_type = other DNA
                        note = Sequence of reverse primer for FUT6-4
                        organism = synthetic construct
SEQUENCE: 250
acaaacccat agctctgccc                                                  20

SEQ ID NO: 251          moltype = DNA   length = 20
FEATURE                 Location/Qualifiers
source                  1..20
                        mol_type = other DNA
                        note = Sequence of forward primer for KLF1-1
                        organism = synthetic construct
SEQUENCE: 251
cccatcccca gtcactagga                                                  20

SEQ ID NO: 252          moltype = DNA   length = 20
FEATURE                 Location/Qualifiers
source                  1..20
                        mol_type = other DNA
                        note = Sequence of reverse primer for KLF1-1
                        organism = synthetic construct
SEQUENCE: 252
ggacatgact gggcagacag                                                  20

SEQ ID NO: 253          moltype = DNA   length = 20
FEATURE                 Location/Qualifiers
source                  1..20
                        mol_type = other DNA
                        note = Sequence of forward primer for KLF1-4
                        organism = synthetic construct
SEQUENCE: 253
tacccggaca gtagcccgta                                                  20

SEQ ID NO: 254          moltype = DNA   length = 20
FEATURE                 Location/Qualifiers
source                  1..20
                        mol_type = other DNA
                        note = Sequence of reverse primer for KLF1-4
                        organism = synthetic construct
SEQUENCE: 254
```
ggcttttggg ttcggaggat                                                   20

SEQ ID NO: 255          moltype = DNA   length = 20
FEATURE                 Location/Qualifiers
source                  1..20
                        mol_type = other DNA
                        note = Sequence of forward primer for KLF1-6
                        organism = synthetic construct
SEQUENCE: 255
atcctccgaa cccaaaagcc                                                   20

SEQ ID NO: 256          moltype = DNA   length = 20
FEATURE                 Location/Qualifiers
source                  1..20
                        mol_type = other DNA
                        note = Sequence of reverse primer for KLF1-6
                        organism = synthetic construct
SEQUENCE: 256
ccctccacgt gaagtctgag                                                   20

SEQ ID NO: 257          moltype = DNA   length = 20
FEATURE                 Location/Qualifiers
source                  1..20
                        mol_type = other DNA
                        note = Sequence of forward primer for KLF1-9
                        organism = synthetic construct
SEQUENCE: 257
ggtccaggtg ctgggtaaaa                                                   20

SEQ ID NO: 258          moltype = DNA   length = 20
FEATURE                 Location/Qualifiers
source                  1..20
                        mol_type = other DNA
                        note = Sequence of reverse primer for KLF1-9
                        organism = synthetic construct
SEQUENCE: 258
tgatagcagc ctccaacgtc                                                   20

SEQ ID NO: 259          moltype = DNA   length = 20
FEATURE                 Location/Qualifiers
source                  1..20
                        mol_type = other DNA
                        note = Sequence of forward primer for LU-3
                        organism = synthetic construct
SEQUENCE: 259
ctgagatgca gggctctgag                                                   20

SEQ ID NO: 260          moltype = DNA   length = 20
FEATURE                 Location/Qualifiers
source                  1..20
                        mol_type = other DNA
                        note = Sequence of reverse primer for LU-3
                        organism = synthetic construct
SEQUENCE: 260
ggatgcccga ggacacttac                                                   20

SEQ ID NO: 261          moltype = DNA   length = 20
FEATURE                 Location/Qualifiers
source                  1..20
                        mol_type = other DNA
                        note = Sequence of forward primer for LU-7
                        organism = synthetic construct
SEQUENCE: 261
ccttagatcc cacggagcac                                                   20

SEQ ID NO: 262          moltype = DNA   length = 20
FEATURE                 Location/Qualifiers
source                  1..20
                        mol_type = other DNA
                        note = Sequence of reverse primer for LU-7
                        organism = synthetic construct
SEQUENCE: 262
cagatcaggt ggctgcctaa                                                   20

SEQ ID NO: 263          moltype = DNA   length = 21
FEATURE                 Location/Qualifiers
source                  1..21
                        mol_type = other DNA
                        note = Sequence of forward primer for LU-9

-continued

```
                       organism = synthetic construct
SEQUENCE: 263
ctggacaaac aggacgagtt c                                              21

SEQ ID NO: 264         moltype = DNA  length = 20
FEATURE                Location/Qualifiers
source                 1..20
                       mol_type = other DNA
                       note = Sequence of reverse primer for LU-9
                       organism = synthetic construct
SEQUENCE: 264
ctccagctga gtttggggtc                                                20

SEQ ID NO: 265         moltype = DNA  length = 19
FEATURE                Location/Qualifiers
source                 1..19
                       mol_type = other DNA
                       note = Sequence of forward primer for LU-11
                       organism = synthetic construct
SEQUENCE: 265
gcaccggtga gtgactgag                                                 19

SEQ ID NO: 266         moltype = DNA  length = 21
FEATURE                Location/Qualifiers
source                 1..21
                       mol_type = other DNA
                       note = Sequence of reverse primer for LU-11
                       organism = synthetic construct
SEQUENCE: 266
tcattgcaga tagcaggcca c                                              21

SEQ ID NO: 267         moltype = DNA  length = 20
FEATURE                Location/Qualifiers
source                 1..20
                       mol_type = other DNA
                       note = Sequence of forward primer for FUT2-1
                       organism = synthetic construct
SEQUENCE: 267
gcctccatct cccagctaac                                                20

SEQ ID NO: 268         moltype = DNA  length = 20
FEATURE                Location/Qualifiers
source                 1..20
                       mol_type = other DNA
                       note = Sequence of reverse primer for FUT2-1
                       organism = synthetic construct
SEQUENCE: 268
aggcggccta ttgcattgat                                                20

SEQ ID NO: 269         moltype = DNA  length = 20
FEATURE                Location/Qualifiers
source                 1..20
                       mol_type = other DNA
                       note = Sequence of forward primer for FUT2-3
                       organism = synthetic construct
SEQUENCE: 269
cctggcagaa ctaccacctg                                                20

SEQ ID NO: 270         moltype = DNA  length = 20
FEATURE                Location/Qualifiers
source                 1..20
                       mol_type = other DNA
                       note = Sequence of reverse primer for FUT2-3
                       organism = synthetic construct
SEQUENCE: 270
atagtcccct cggcgaacat                                                20

SEQ ID NO: 271         moltype = DNA  length = 20
FEATURE                Location/Qualifiers
source                 1..20
                       mol_type = other DNA
                       note = Sequence of forward primer for FUT2-6
                       organism = synthetic construct
SEQUENCE: 271
gcggagacac catctacctg                                                20

SEQ ID NO: 272         moltype = DNA  length = 20
FEATURE                Location/Qualifiers
source                 1..20
```

```
                            mol_type = other DNA
                            note = Sequence of reverse primer for FUT2-6
                            organism = synthetic construct
SEQUENCE: 272
gagggaggca gagaaggaga                                                   20

SEQ ID NO: 273              moltype = DNA   length = 20
FEATURE                     Location/Qualifiers
source                      1..20
                            mol_type = other DNA
                            note = Sequence of forward primer for FUT1-1
                            organism = synthetic construct
SEQUENCE: 273
agtctccctg gctctcaagg                                                   20

SEQ ID NO: 274              moltype = DNA   length = 20
FEATURE                     Location/Qualifiers
source                      1..20
                            mol_type = other DNA
                            note = Sequence of reverse primer for FUT1-1
                            organism = synthetic construct
SEQUENCE: 274
cgatggacag gaggctacac                                                   20

SEQ ID NO: 275              moltype = DNA   length = 20
FEATURE                     Location/Qualifiers
source                      1..20
                            mol_type = other DNA
                            note = Sequence of forward primer for FUT1-4
                            organism = synthetic construct
SEQUENCE: 275
ttgctggtga ccacgaaaac                                                   20

SEQ ID NO: 276              moltype = DNA   length = 20
FEATURE                     Location/Qualifiers
source                      1..20
                            mol_type = other DNA
                            note = Sequence of reverse primer for FUT1-4
                            organism = synthetic construct
SEQUENCE: 276
cttccaccat ctccgggaac                                                   20

SEQ ID NO: 277              moltype = DNA   length = 20
FEATURE                     Location/Qualifiers
source                      1..20
                            mol_type = other DNA
                            note = Sequence of forward primer for FUT1-6
                            organism = synthetic construct
SEQUENCE: 277
ctcaagtccg cgtactcctc                                                   20

SEQ ID NO: 278              moltype = DNA   length = 20
FEATURE                     Location/Qualifiers
source                      1..20
                            mol_type = other DNA
                            note = Sequence of reverse primer for FUT1-6
                            organism = synthetic construct
SEQUENCE: 278
cacctggact gtctacccca                                                   20

SEQ ID NO: 279              moltype = DNA   length = 19
FEATURE                     Location/Qualifiers
source                      1..19
                            mol_type = other DNA
                            note = Sequence of forward primer for FUT1-8
                            organism = synthetic construct
SEQUENCE: 279
cggtctggac acaggatcg                                                    19

SEQ ID NO: 280              moltype = DNA   length = 20
FEATURE                     Location/Qualifiers
source                      1..20
                            mol_type = other DNA
                            note = Sequence of reverse primer for FUT1-8
                            organism = synthetic construct
SEQUENCE: 280
cctgggacta aggagtgctg                                                   20

SEQ ID NO: 281              moltype = DNA   length = 20
```

| | |
|---|---|
| FEATURE | Location/Qualifiers |
| source | 1..20<br>mol_type = other DNA<br>note = Sequence of forward primer for A4GALT-1<br>organism = synthetic construct |

SEQUENCE: 281
gggcccctca caagtacatt                                              20

| | |
|---|---|
| SEQ ID NO: 282 | moltype = DNA  length = 20 |
| FEATURE | Location/Qualifiers |
| source | 1..20<br>mol_type = other DNA<br>note = Sequence of reverse primer for A4GALT-1<br>organism = synthetic construct |

SEQUENCE: 282
ctgaggcctt ctacccatc                                               20

| | |
|---|---|
| SEQ ID NO: 283 | moltype = DNA  length = 20 |
| FEATURE | Location/Qualifiers |
| source | 1..20<br>mol_type = other DNA<br>note = Sequence of forward primer for A4GALT-3<br>organism = synthetic construct |

SEQUENCE: 283
ccgttgtagt ggtccacgaa                                              20

| | |
|---|---|
| SEQ ID NO: 284 | moltype = DNA  length = 18 |
| FEATURE | Location/Qualifiers |
| source | 1..18<br>mol_type = other DNA<br>note = Sequence of reverse primer for A4GALT-3<br>organism = synthetic construct |

SEQUENCE: 284
ctgggagccc tacctgct                                                18

| | |
|---|---|
| SEQ ID NO: 285 | moltype = DNA  length = 20 |
| FEATURE | Location/Qualifiers |
| source | 1..20<br>mol_type = other DNA<br>note = Sequence of forward primer for A4GALT-5<br>organism = synthetic construct |

SEQUENCE: 285
cggaagccct ttcatcagga                                              20

| | |
|---|---|
| SEQ ID NO: 286 | moltype = DNA  length = 20 |
| FEATURE | Location/Qualifiers |
| source | 1..20<br>mol_type = other DNA<br>note = Sequence of reverse primer for A4GALT-5<br>organism = synthetic construct |

SEQUENCE: 286
atctactggc acgttgtggg                                              20

| | |
|---|---|
| SEQ ID NO: 287 | moltype = DNA  length = 20 |
| FEATURE | Location/Qualifiers |
| source | 1..20<br>mol_type = other DNA<br>note = Sequence of forward primer for B3GALNT1-2<br>organism = synthetic construct |

SEQUENCE: 287
gggctgcaat cacacgtctc                                              20

| | |
|---|---|
| SEQ ID NO: 288 | moltype = DNA  length = 21 |
| FEATURE | Location/Qualifiers |
| source | 1..21<br>mol_type = other DNA<br>note = Sequence of reverse primer for B3GALNT1-2<br>organism = synthetic construct |

SEQUENCE: 288
tcctttcaag gtgttccctc c                                            21

| | |
|---|---|
| SEQ ID NO: 289 | moltype = DNA  length = 20 |
| FEATURE | Location/Qualifiers |
| source | 1..20<br>mol_type = other DNA<br>note = Sequence of forward primer for B3GALNT1-5<br>organism = synthetic construct |

SEQUENCE: 289
ggcattgggg caaaactcag                                              20

-continued

```
SEQ ID NO: 290         moltype = DNA  length = 20
FEATURE                Location/Qualifiers
source                 1..20
                       mol_type = other DNA
                       note = Sequence of reverse primer for B3GALNT1-5
                       organism = synthetic construct
SEQUENCE: 290
tgacctccca cccttcagat                                              20

SEQ ID NO: 291         moltype = DNA  length = 23
FEATURE                Location/Qualifiers
source                 1..23
                       mol_type = other DNA
                       note = Sequence of forward primer for GYPA-1
                       organism = synthetic construct
SEQUENCE: 291
tggtgtacaa catgatggtt tga                                          23

SEQ ID NO: 292         moltype = DNA  length = 22
FEATURE                Location/Qualifiers
source                 1..22
                       mol_type = other DNA
                       note = Sequence of reverse primer for GYPA-1
                       organism = synthetic construct
SEQUENCE: 292
tgtacaacag ggtgaatgga gt                                           22

SEQ ID NO: 293         moltype = DNA  length = 22
FEATURE                Location/Qualifiers
source                 1..22
                       mol_type = other DNA
                       note = Sequence of forward primer for GYPA-5
                       organism = synthetic construct
SEQUENCE: 293
tgtcacgaaa gcttgagaac tg                                           22

SEQ ID NO: 294         moltype = DNA  length = 20
FEATURE                Location/Qualifiers
source                 1..20
                       mol_type = other DNA
                       note = Sequence of reverse primer for GYPA-5
                       organism = synthetic construct
SEQUENCE: 294
gctctatgtc cacgcagtca                                              20

SEQ ID NO: 295         moltype = DNA  length = 20
FEATURE                Location/Qualifiers
source                 1..20
                       mol_type = other DNA
                       note = Sequence of forward primer for KEL-1
                       organism = synthetic construct
SEQUENCE: 295
acagcggaaa tacctggcaa                                              20

SEQ ID NO: 296         moltype = DNA  length = 20
FEATURE                Location/Qualifiers
source                 1..20
                       mol_type = other DNA
                       note = Sequence of reverse primer for KEL-1
                       organism = synthetic construct
SEQUENCE: 296
cacttgatcc cctggttccc                                              20

SEQ ID NO: 297         moltype = DNA  length = 21
FEATURE                Location/Qualifiers
source                 1..21
                       mol_type = other DNA
                       note = Sequence of forward primer for KEL-3
                       organism = synthetic construct
SEQUENCE: 297
ccaacgtctg cagcattctc t                                            21

SEQ ID NO: 298         moltype = DNA  length = 20
FEATURE                Location/Qualifiers
source                 1..20
                       mol_type = other DNA
                       note = Sequence of reverse primer for KEL-3
                       organism = synthetic construct
```

```
SEQUENCE: 298
atgctcctgg gagctgattc                                               20

SEQ ID NO: 299          moltype = DNA  length = 20
FEATURE                 Location/Qualifiers
source                  1..20
                        mol_type = other DNA
                        note = Sequence of forward primer for KEL-5
                        organism = synthetic construct
SEQUENCE: 299
atcataacac ctgtcggccc                                               20

SEQ ID NO: 300          moltype = DNA  length = 20
FEATURE                 Location/Qualifiers
source                  1..20
                        mol_type = other DNA
                        note = Sequence of reverse primer for KEL-5
                        organism = synthetic construct
SEQUENCE: 300
gggagggact gtgtaggtct                                               20

SEQ ID NO: 301          moltype = DNA  length = 20
FEATURE                 Location/Qualifiers
source                  1..20
                        mol_type = other DNA
                        note = Sequence of forward primer for KEL-8
                        organism = synthetic construct
SEQUENCE: 301
atccccatct cgcttgttcc                                               20

SEQ ID NO: 302          moltype = DNA  length = 20
FEATURE                 Location/Qualifiers
source                  1..20
                        mol_type = other DNA
                        note = Sequence of reverse primer for KEL-8
                        organism = synthetic construct
SEQUENCE: 302
agcccttttc caagggtcag                                               20

SEQ ID NO: 303          moltype = DNA  length = 20
FEATURE                 Location/Qualifiers
source                  1..20
                        mol_type = other DNA
                        note = Sequence of forward primer for KEL-11
                        organism = synthetic construct
SEQUENCE: 303
gcggcgaacc tctgctttag                                               20

SEQ ID NO: 304          moltype = DNA  length = 19
FEATURE                 Location/Qualifiers
source                  1..19
                        mol_type = other DNA
                        note = Sequence of reverse primer for KEL-11
                        organism = synthetic construct
SEQUENCE: 304
atccccctccc ccagttagc                                               19

SEQ ID NO: 305          moltype = DNA  length = 20
FEATURE                 Location/Qualifiers
source                  1..20
                        mol_type = other DNA
                        note = Sequence of forward primer for KEL-15
                        organism = synthetic construct
SEQUENCE: 305
agcatcttcc accctgcttt                                               20

SEQ ID NO: 306          moltype = DNA  length = 21
FEATURE                 Location/Qualifiers
source                  1..21
                        mol_type = other DNA
                        note = Sequence of reverse primer for KEL-15
                        organism = synthetic construct
SEQUENCE: 306
agcccttgtc tttttgcctc t                                             21

SEQ ID NO: 307          moltype = DNA  length = 20
FEATURE                 Location/Qualifiers
source                  1..20
                        mol_type = other DNA
```

```
                             -continued note = Sequence of forward primer for ERMAP-1
                       organism = synthetic construct
SEQUENCE: 307
tgcttggcag gcagtatctt                                                 20

SEQ ID NO: 308         moltype = DNA   length = 20
FEATURE                Location/Qualifiers
source                 1..20
                       mol_type = other DNA
                       note = Sequence of reverse primer for ERMAP-1
                       organism = synthetic construct
SEQUENCE: 308
ccctgacagc cttttccagt                                                 20

SEQ ID NO: 309         moltype = DNA   length = 20
FEATURE                Location/Qualifiers
source                 1..20
                       mol_type = other DNA
                       note = Sequence of forward primer for ERMAP-2
                       organism = synthetic construct
SEQUENCE: 309
ctcccagttg gccttgtctc                                                 20

SEQ ID NO: 310         moltype = DNA   length = 20
FEATURE                Location/Qualifiers
source                 1..20
                       mol_type = other DNA
                       note = Sequence of reverse primer for ERMAP-2
                       organism = synthetic construct
SEQUENCE: 310
tctctcacta gcaccgtcct                                                 20

SEQ ID NO: 311         moltype = DNA   length = 20
FEATURE                Location/Qualifiers
source                 1..20
                       mol_type = other DNA
                       note = Sequence of forward primer for ART4-2
                       organism = synthetic construct
SEQUENCE: 311
gaatggtggc ccctgtgtag                                                 20

SEQ ID NO: 312         moltype = DNA   length = 20
FEATURE                Location/Qualifiers
source                 1..20
                       mol_type = other DNA
                       note = Sequence of reverse primer for ART4-2
                       organism = synthetic construct
SEQUENCE: 312
tagagccatg gcctctgttg                                                 20

SEQ ID NO: 313         moltype = DNA   length = 20
FEATURE                Location/Qualifiers
source                 1..20
                       mol_type = other DNA
                       note = Sequence of forward primer for ART4-5
                       organism = synthetic construct
SEQUENCE: 313
ttaagccagg ctaagtgggc                                                 20

SEQ ID NO: 314         moltype = DNA   length = 22
FEATURE                Location/Qualifiers
source                 1..22
                       mol_type = other DNA
                       note = Sequence of reverse primer for ART4-5
                       organism = synthetic construct
SEQUENCE: 314
aaatctgcaa ccacattcac ca                                              22

SEQ ID NO: 315         moltype = DNA   length = 20
FEATURE                Location/Qualifiers
source                 1..20
                       mol_type = other DNA
                       note = Sequence of forward primer for ICAM4-1
                       organism = synthetic construct
SEQUENCE: 315
gctcaattgc agcaacagct                                                 20

SEQ ID NO: 316         moltype = DNA   length = 19
FEATURE                Location/Qualifiers
```

```
                        -continued source                  1..19
                        mol_type = other DNA
                        note = Sequence of reverse primer for ICAM4-1
                        organism = synthetic construct
SEQUENCE: 316
gcccctgtcc ctcactgta                                                  19

SEQ ID NO: 317          moltype = DNA  length = 20
FEATURE                 Location/Qualifiers
source                  1..20
                        mol_type = other DNA
                        note = Sequence of forward primer for ABCG2-3
                        organism = synthetic construct
SEQUENCE: 317
gcgggttcaa gcgattctac                                                 20

SEQ ID NO: 318          moltype = DNA  length = 20
FEATURE                 Location/Qualifiers
source                  1..20
                        mol_type = other DNA
                        note = Sequence of reverse primer for ABCG2-3
                        organism = synthetic construct
SEQUENCE: 318
cctagtactt tgggaggccg                                                 20

SEQ ID NO: 319          moltype = DNA  length = 22
FEATURE                 Location/Qualifiers
source                  1..22
                        mol_type = other DNA
                        note = Sequence of forward primer for ABCG2-6
                        organism = synthetic construct
SEQUENCE: 319
tctctaggac tgagaaggga gt                                              22

SEQ ID NO: 320          moltype = DNA  length = 20
FEATURE                 Location/Qualifiers
source                  1..20
                        mol_type = other DNA
                        note = Sequence of reverse primer for ABCG2-6
                        organism = synthetic construct
SEQUENCE: 320
aacccactga gcacagaagt                                                 20

SEQ ID NO: 321          moltype = DNA  length = 20
FEATURE                 Location/Qualifiers
source                  1..20
                        mol_type = other DNA
                        note = Sequence of forward primer for ABCG2-9
                        organism = synthetic construct
SEQUENCE: 321
tggagttgca ctctacctca                                                 20

SEQ ID NO: 322          moltype = DNA  length = 21
FEATURE                 Location/Qualifiers
source                  1..21
                        mol_type = other DNA
                        note = Sequence of reverse primer for ABCG2-9
                        organism = synthetic construct
SEQUENCE: 322
tgaaagccca tggatcaacc t                                               21

SEQ ID NO: 323          moltype = DNA  length = 20
FEATURE                 Location/Qualifiers
source                  1..20
                        mol_type = other DNA
                        note = Sequence of forward primer for ABCG2-12
                        organism = synthetic construct
SEQUENCE: 323
cattcgcgca caactcactt                                                 20

SEQ ID NO: 324          moltype = DNA  length = 20
FEATURE                 Location/Qualifiers
source                  1..20
                        mol_type = other DNA
                        note = Sequence of reverse primer for ABCG2-12
                        organism = synthetic construct
SEQUENCE: 324
tgtttacctt gccctgctcc                                                 20
```

```
SEQ ID NO: 325          moltype = DNA  length = 20
FEATURE                 Location/Qualifiers
source                  1..20
                        mol_type = other DNA
                        note = Sequence of forward primer for ABCG2-17
                        organism = synthetic construct
SEQUENCE: 325
gagctataga ggcctgggga                                                    20

SEQ ID NO: 326          moltype = DNA  length = 21
FEATURE                 Location/Qualifiers
source                  1..21
                        mol_type = other DNA
                        note = Sequence of reverse primer for ABCG2-17
                        organism = synthetic construct
SEQUENCE: 326
atccactgat tgcaaagcca c                                                  21

SEQ ID NO: 327          moltype = DNA  length = 20
FEATURE                 Location/Qualifiers
source                  1..20
                        mol_type = other DNA
                        note = Sequence of forward primer for ABCG2-20
                        organism = synthetic construct
SEQUENCE: 327
tcaggagcaa aaggacagca                                                    20

SEQ ID NO: 328          moltype = DNA  length = 20
FEATURE                 Location/Qualifiers
source                  1..20
                        mol_type = other DNA
                        note = Sequence of reverse primer for ABCG2-20
                        organism = synthetic construct
SEQUENCE: 328
tcttacagga ctggcacacg                                                    20

SEQ ID NO: 329          moltype = DNA  length = 20
FEATURE                 Location/Qualifiers
source                  1..20
                        mol_type = other DNA
                        note = Sequence of forward primer for ABCG2-22
                        organism = synthetic construct
SEQUENCE: 329
gttgttgcaa gccgaagagc                                                    20

SEQ ID NO: 330          moltype = DNA  length = 22
FEATURE                 Location/Qualifiers
source                  1..22
                        mol_type = other DNA
                        note = Sequence of reverse primer for ABCG2-22
                        organism = synthetic construct
SEQUENCE: 330
caggctttgc agacatctat gg                                                 22

SEQ ID NO: 331          moltype = DNA  length = 20
FEATURE                 Location/Qualifiers
source                  1..20
                        mol_type = other DNA
                        note = Sequence of forward primer for ABCG2-24
                        organism = synthetic construct
SEQUENCE: 331
agaaccagac ctgacatgcg                                                    20

SEQ ID NO: 332          moltype = DNA  length = 21
FEATURE                 Location/Qualifiers
source                  1..21
                        mol_type = other DNA
                        note = Sequence of reverse primer for ABCG2-24
                        organism = synthetic construct
SEQUENCE: 332
catgaaacct ggtctcaacg c                                                  21

SEQ ID NO: 333          moltype = DNA  length = 20
FEATURE                 Location/Qualifiers
source                  1..20
                        mol_type = other DNA
                        note = Sequence of forward primer for ABCG2-26
                        organism = synthetic construct
SEQUENCE: 333
```

```
cggggaagcc attggtgttt                                                    20

SEQ ID NO: 334           moltype = DNA  length = 20
FEATURE                  Location/Qualifiers
source                   1..20
                         mol_type = other DNA
                         note = Sequence of reverse primer for ABCG2-26
                         organism = synthetic construct
SEQUENCE: 334
agttgtgcct gtcttcccat                                                    20

SEQ ID NO: 335           moltype = DNA  length = 20
FEATURE                  Location/Qualifiers
source                   1..20
                         mol_type = other DNA
                         note = Sequence of forward primer for AQP1-2
                         organism = synthetic construct
SEQUENCE: 335
gggcttcaaa tacccggtgg                                                    20

SEQ ID NO: 336           moltype = DNA  length = 20
FEATURE                  Location/Qualifiers
source                   1..20
                         mol_type = other DNA
                         note = Sequence of reverse primer for AQP1-2
                         organism = synthetic construct
SEQUENCE: 336
ggtgatgcct gagaggatgg                                                    20
```